(12) United States Patent
Eigler et al.

(10) Patent No.: US 11,850,138 B2
(45) Date of Patent: *Dec. 26, 2023

(54) SHUNT FOR REDISTRIBUTING ATRIAL BLOOD VOLUME

(71) Applicant: V-Wave Ltd., Caesarea (IL)

(72) Inventors: Neal Eigler, Agoura Hills, CA (US); Nir Nae, Binyamina (IL); Lior Rosen, Zikhron Ya'akov (IL); Werner Hafelfinger, Thousand Oaks, CA (US); Erez Rozenfeld, Shoham (IL); James S. Whiting, Los Angeles, CA (US); Menashe Yacoby, Ramat Gan (IL); Yaacov Nitzan, Hertzelia (IL)

(73) Assignee: V-Wave Ltd., Caesarea (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/823,047

(22) Filed: Aug. 29, 2022

(65) Prior Publication Data
US 2022/0409357 A1 Dec. 29, 2022

Related U.S. Application Data

(60) Continuation of application No. 17/175,549, filed on Feb. 12, 2021, which is a continuation-in-part of
(Continued)

(51) Int. Cl.
*A61F 2/01* (2006.01)
*A61F 2/24* (2006.01)
*A61M 27/00* (2006.01)

(52) U.S. Cl.
CPC .............. *A61F 2/01* (2013.01); *A61F 2/2487* (2013.01); *A61M 27/002* (2013.01);
(Continued)

(58) Field of Classification Search
CPC .... A61F 2/01; A61F 2/2487; A61F 2002/249; A61F 2250/0051; A61F 2250/0098; A61M 27/002
See application file for complete search history.

(56) References Cited

U.S. PATENT DOCUMENTS 3,852,334 A 12/1974 Dusza et al.
3,874,388 A 4/1975 King et al.
(Continued)

FOREIGN PATENT DOCUMENTS

AU 2003291117 B2 4/2009
CA 2378920 A1 2/2001
(Continued)

OTHER PUBLICATIONS

Abraham et al., "Hemodynamic Monitoring in Advanced Heart Failure: Results from the LAPTOP-HF Trial," J Card Failure, 22:940 (2016) (Abstract Only).
(Continued)

*Primary Examiner* — Philip R Wiest
(74) *Attorney, Agent, or Firm* — Eversheds Sutherland (US) LLP; Christopher C. Bolten; Nicola A. Pisano

(57) ABSTRACT

Systems and methods for implanting a shunt for regulating blood pressure between a patient's left and right atria are provided. The shunt comprises an anchor having a neck region, first and second end regions, and a conduit affixed with the anchor formed of a biocompatible material that is resistant to transmural and translation tissue ingrowth and that reduces a risk of paradoxical embolism. The shunt may be advanced through the sheath until the first region protrudes from the sheath and self-expands within the left atrium. The shunt and the sheath may then be retracted until the first region contacts the left side of the atrial septum. The sheath may further be retracted until the counterforce exerted by shunt tension on the atrial septum overcomes the
(Continued)

friction of the retained portions of the shunt such that the second region is exposed from the sheath and self-expands within the second atrium.

26 Claims, 11 Drawing Sheets

Related U.S. Application Data application No. 16/130,988, filed on Sep. 13, 2018, now Pat. No. 10,925,706, which is a continuation of application No. 15/449,834, filed on Mar. 3, 2017, now Pat. No. 10,076,403, which is a continuation-in-part of application No. 14/712,801, filed on May 14, 2015, now Pat. No. 9,980,815, which is a division of application No. 13/193,335, filed on Jul. 28, 2011, now Pat. No. 9,034,034, which is a continuation-in-part of application No. PCT/IL2010/000354, filed on May 4, 2010.

(60) Provisional application No. 61/425,792, filed on Dec. 22, 2010, provisional application No. 61/240,667, filed on Sep. 9, 2009, provisional application No. 61/175,073, filed on May 4, 2009.

(52) U.S. Cl.
CPC . *A61F 2002/249* (2013.01); *A61F 2250/0051* (2013.01); *A61F 2250/0098* (2013.01)

(56) References Cited

U.S. PATENT DOCUMENTS

| | | | |
|---|---|---|---|
| 3,952,334 A | 4/1976 | Bokros et al. |
| 4,364,395 A | 12/1982 | Redmond et al. |
| 4,484,955 A | 11/1984 | Hochstein |
| 4,601,309 A | 7/1986 | Chang |
| 4,617,932 A | 10/1986 | Kornberg |
| 4,662,355 A | 5/1987 | Pieronne et al. |
| 4,665,906 A | 5/1987 | Jervis |
| 4,705,507 A | 11/1987 | Boyles |
| 4,836,204 A | 6/1989 | Landymore et al. |
| 4,979,955 A | 12/1990 | Smith |
| 4,988,339 A | 1/1991 | Vadher |
| 4,995,857 A | 2/1991 | Arnold |
| 5,035,702 A | 7/1991 | Taheri |
| 5,035,706 A | 7/1991 | Giantureo et al. |
| 5,037,427 A | 8/1991 | Harada et al. |
| 5,089,005 A | 2/1992 | Harada |
| 5,186,431 A | 2/1993 | Tamari |
| 5,197,978 A | 3/1993 | Hess |
| 5,234,447 A | 8/1993 | Kaster et al. |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,378,239 A | 1/1995 | Termin et al. |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,545,210 A | 8/1996 | Hess et al. |
| 5,556,386 A | 9/1996 | Todd |
| 5,578,008 A | 11/1996 | Hara |
| 5,584,803 A | 12/1996 | Stevens et al. |
| 5,597,377 A | 1/1997 | Aldea |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,741,324 A | 4/1998 | Glastra |
| 5,749,880 A | 5/1998 | Banas et al. |
| 5,779,716 A | 7/1998 | Cano et al. |
| 5,795,307 A | 8/1998 | Krueger |
| 5,810,836 A | 9/1998 | Hussein et al. |
| 5,824,062 A | 10/1998 | Patke et al. |
| 5,824,071 A | 10/1998 | Nelson et al. |
| 5,846,261 A | 12/1998 | Kotula et al. |
| 5,910,144 A | 6/1999 | Hayashi |
| 5,916,193 A | 6/1999 | Stevens et al. |
| 5,941,850 A | 8/1999 | Shah et al. |
| 5,957,949 A | 9/1999 | Leonhardt et al. |
| 5,990,379 A | 11/1999 | Gregory |
| 6,007,544 A | 12/1999 | Kim |
| 6,027,518 A | 2/2000 | Gaber |
| 6,039,755 A | 3/2000 | Edwin et al. |
| 6,039,759 A | 3/2000 | Carpentier et al. |
| 6,086,610 A | 7/2000 | Duerig et al. |
| 6,111,520 A | 8/2000 | Allen et al. |
| 6,117,159 A | 9/2000 | Huebsch et al. |
| 6,120,534 A | 9/2000 | Ruiz |
| 6,124,523 A | 9/2000 | Banas et al. |
| 6,126,686 A | 10/2000 | Badylak et al. |
| 6,165,188 A | 12/2000 | Saadat et al. |
| 6,210,318 B1 | 4/2001 | Lederman |
| 6,214,029 B1 | 4/2001 | Thill et al. |
| 6,214,039 B1 | 4/2001 | Banas et al. |
| 6,217,541 B1 | 4/2001 | Yu |
| 6,221,096 B1 | 4/2001 | Aiba et al. |
| 6,231,587 B1 | 5/2001 | Makower |
| 6,242,762 B1 | 6/2001 | Brown et al. |
| 6,245,099 B1 | 6/2001 | Edwin et al. |
| 6,254,564 B1 | 7/2001 | Wilk et al. |
| 6,260,552 B1 | 7/2001 | Mortier et al. |
| 6,264,684 B1 | 7/2001 | Banas et al. |
| 6,270,515 B1 | 8/2001 | Linden et al. |
| 6,270,526 B1 | 8/2001 | Cox |
| 6,277,078 B1 | 8/2001 | Porat et al. |
| 6,278,379 B1 | 8/2001 | Allen et al. |
| 6,290,728 B1 | 9/2001 | Phelps et al. |
| 6,302,892 B1 | 10/2001 | Wilk |
| 6,306,141 B1 | 10/2001 | Jervis |
| 6,328,699 B1 | 12/2001 | Eigler et al. |
| 6,344,022 B1 | 2/2002 | Jarvik |
| 6,358,277 B1 | 3/2002 | Duran |
| 6,391,036 B1 | 5/2002 | Berg et al. |
| 6,398,803 B1 | 6/2002 | Layne et al. |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,475,136 B1 | 11/2002 | Forsell |
| 6,478,776 B1 | 11/2002 | Rosenman et al. |
| 6,485,507 B1 | 11/2002 | Walak et al. |
| 6,488,702 B1 | 12/2002 | Besselink |
| 6,491,705 B2 | 12/2002 | Gifford, III et al. |
| 6,527,698 B1 | 3/2003 | Kung et al. |
| 6,544,208 B2 | 4/2003 | Ethier et al. |
| 6,547,814 B2 | 4/2003 | Edwin et al. |
| 6,562,066 B1 * | 5/2003 | Martin .................. A61F 2/82 623/1.13 |
| 6,572,652 B2 | 6/2003 | Shaknovich |
| 6,579,314 B1 | 6/2003 | Lombardi et al. |
| 6,589,198 B1 | 7/2003 | Soltanpour et al. |
| 6,616,675 B1 | 9/2003 | Evard et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,652,578 B2 | 11/2003 | Bailey et al. |
| 6,685,664 B2 | 2/2004 | Levin et al. |
| 6,712,836 B1 | 3/2004 | Berg et al. |
| 6,740,115 B2 | 5/2004 | Lombardi et al. |
| 6,758,858 B2 | 7/2004 | McCrea et al. |
| 6,764,507 B2 | 7/2004 | Shanley et al. |
| 6,770,087 B2 | 8/2004 | Layne et al. |
| 6,797,217 B2 | 9/2004 | McCrea et al. |
| 6,890,350 B1 | 5/2005 | Walak |
| 6,923,829 B2 | 8/2005 | Boyle et al. |

(56) References Cited

U.S. PATENT DOCUMENTS

| | | |
|---|---|---|
| 6,970,742 B2 | 11/2005 | Mann et al. |
| 7,001,409 B2 | 2/2006 | Amplatz |
| 7,004,966 B2 | 2/2006 | Edwin et al. |
| 7,025,777 B2 | 4/2006 | Moore |
| 7,060,150 B2 | 6/2006 | Banas et al. |
| 7,083,640 B2 | 8/2006 | Lombardi et al. |
| 7,115,095 B2 | 10/2006 | Eigler et al. |
| 7,118,600 B2 | 10/2006 | Dua et al. |
| 7,137,953 B2 | 11/2006 | Eigler et al. |
| 7,147,604 B1 | 12/2006 | Allen et al. |
| 7,149,587 B2 | 12/2006 | Wardle et al. |
| 7,169,160 B1 | 1/2007 | Middleman et al. |
| 7,169,172 B2 | 1/2007 | Levine et al. |
| 7,195,594 B2 | 3/2007 | Eigler et al. |
| 7,208,010 B2 | 4/2007 | Shanley et al. |
| 7,226,558 B2 | 6/2007 | Nieman et al. |
| 7,245,117 B1 | 7/2007 | Joy et al. |
| 7,294,115 B1 | 11/2007 | Wilk |
| 7,306,756 B2 | 12/2007 | Edwin et al. |
| 7,402,899 B1 | 7/2008 | Whiting et al. |
| 7,439,723 B2 | 10/2008 | Allen et al. |
| 7,468,071 B2 | 12/2008 | Edwin et al. |
| 7,483,743 B2 | 1/2009 | Mann et al. |
| 7,498,799 B2 | 3/2009 | Allen et al. |
| 7,509,169 B2 | 3/2009 | Eigler et al. |
| 7,550,978 B2 | 6/2009 | Joy et al. |
| 7,578,899 B2 | 8/2009 | Edwin et al. |
| 7,590,449 B2 | 9/2009 | Mann et al. |
| 7,615,010 B1 | 11/2009 | Najafi et al. |
| 7,621,879 B2 | 11/2009 | Eigler et al. |
| 7,679,355 B2 | 3/2010 | Allen et al. |
| 7,717,854 B2 | 5/2010 | Mann et al. |
| 7,794,473 B2 | 9/2010 | Tessmer et al. |
| 7,839,153 B2 | 11/2010 | Joy et al. |
| 7,842,083 B2 | 11/2010 | Shanley et al. |
| 7,854,172 B2 | 12/2010 | O'Brien et al. |
| 7,862,513 B2 | 1/2011 | Eigler et al. |
| 7,914,639 B2 | 3/2011 | Layne et al. |
| 7,939,000 B2 | 5/2011 | Edwin et al. |
| 7,988,724 B2 | 8/2011 | Salahieh et al. |
| 7,993,383 B2 | 8/2011 | Hartley et al. |
| 8,012,194 B2 | 9/2011 | Edwin et al. |
| 8,016,877 B2 | 9/2011 | Seguin et al. |
| 8,021,420 B2 | 9/2011 | Dolan |
| 8,025,625 B2 | 9/2011 | Allen |
| 8,025,668 B2 | 9/2011 | McCartney |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,137,605 B2 | 3/2012 | McCrea et al. |
| 8,142,363 B1 | 3/2012 | Eigler et al. |
| 8,147,545 B2 | 4/2012 | Avior |
| 8,157,852 B2 | 4/2012 | Bloom et al. |
| 8,157,860 B2 | 4/2012 | McNamara et al. |
| 8,157,940 B2 | 4/2012 | Edwin et al. |
| 8,158,041 B2 | 4/2012 | Colone |
| 8,187,321 B2 | 5/2012 | Shanley et al. |
| 8,202,313 B2 | 6/2012 | Shanley et al. |
| 8,206,435 B2 | 6/2012 | Shanley et al. |
| 8,216,398 B2 | 7/2012 | Bledsoe et al. |
| 8,235,916 B2 | 8/2012 | Whiting et al. |
| 8,235,933 B2 | 8/2012 | Keren et al. |
| 8,246,677 B2 | 8/2012 | Ryan |
| 8,287,589 B2 | 10/2012 | Otto et al. |
| 8,298,150 B2 | 10/2012 | Mann et al. |
| 8,298,244 B2 | 10/2012 | Garcia et al. |
| 8,303,511 B2 | 11/2012 | Eigler et al. |
| 8,313,524 B2 | 11/2012 | Edwin et al. |
| 8,328,751 B2 | 12/2012 | Keren et al. |
| 8,337,650 B2 | 12/2012 | Edwin et al. |
| 8,348,996 B2 | 1/2013 | Tuval et al. |
| 8,357,193 B2 | 1/2013 | Phan et al. |
| 8,398,708 B2 | 3/2013 | Meiri et al. |
| 8,460,366 B2 | 6/2013 | Rowe |
| 8,468,667 B2 | 6/2013 | Straubinger et al. |
| 8,480,594 B2 | 7/2013 | Eigler et al. |
| 8,579,966 B2 | 11/2013 | Seguin et al. |
| 8,597,225 B2 | 12/2013 | Kapadia |
| 8,617,337 B2 | 12/2013 | Layne et al. |
| 8,617,441 B2 | 12/2013 | Edwin et al. |
| 8,652,284 B2 | 2/2014 | Bogert et al. |
| 8,665,086 B2 | 3/2014 | Miller et al. |
| 8,696,611 B2 | 4/2014 | Nitzan et al. |
| 8,790,241 B2 | 7/2014 | Edwin et al. |
| 8,882,697 B2 | 11/2014 | Celermajer et al. |
| 8,882,798 B2 | 11/2014 | Schwab et al. |
| 8,911,489 B2 | 12/2014 | Ben-Muvhar |
| 9,005,155 B2 | 4/2015 | Sugimoto |
| 9,034,034 B2 | 5/2015 | Nitzan et al. |
| 9,055,917 B2 | 6/2015 | Mann et al. |
| 9,060,696 B2 | 6/2015 | Eigler et al. |
| 9,067,050 B2 | 6/2015 | Gallagher et al. |
| 9,205,236 B2 | 12/2015 | McNamara et al. |
| 9,220,429 B2 | 12/2015 | Nabutovsky et al. |
| 9,358,371 B2 | 6/2016 | McNamara et al. |
| 9,393,115 B2 | 7/2016 | Tabor et al. |
| 9,456,812 B2 | 10/2016 | Finch et al. |
| 9,622,895 B2 | 4/2017 | Cohen et al. |
| 9,629,715 B2 | 4/2017 | Nitzan et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,757,107 B2 | 9/2017 | McNamara et al. |
| 9,789,294 B2 | 10/2017 | Taft et al. |
| 9,918,677 B2 | 3/2018 | Eigler et al. |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,047,421 B2 | 8/2018 | Khan et al. |
| 10,076,403 B1 * | 9/2018 | Eigler .................. A61F 2/2487 |
| 10,105,103 B2 | 10/2018 | Goldshtein et al. |
| 10,111,741 B2 | 10/2018 | Michalak |
| 10,207,087 B2 | 2/2019 | Keren et al. |
| 10,207,807 B2 | 2/2019 | Moran et al. |
| 10,251,740 B2 | 4/2019 | Eigler et al. |
| 10,251,750 B2 | 4/2019 | Alexander et al. |
| 10,265,169 B2 | 4/2019 | Desrosiers et al. |
| 10,299,687 B2 | 5/2019 | Nabutovsky et al. |
| 10,357,320 B2 | 7/2019 | Beira |
| 10,357,357 B2 | 7/2019 | Levi et al. |
| 10,368,981 B2 | 8/2019 | Nitzan et al. |
| 10,463,490 B2 | 11/2019 | Rottenberg et al. |
| 10,478,594 B2 | 11/2019 | Yacoby et al. |
| 10,548,725 B2 | 2/2020 | Alkhatib et al. |
| 10,561,423 B2 | 2/2020 | Sharma |
| 10,583,002 B2 | 3/2020 | Lane et al. |
| 10,639,459 B2 | 5/2020 | Nitzan et al. |
| 10,828,151 B2 | 11/2020 | Nitzan et al. |
| 10,835,394 B2 | 11/2020 | Nae et al. |
| 10,898,698 B1 | 1/2021 | Eigler et al. |
| 10,912,645 B2 | 2/2021 | Rottenberg et al. |
| 10,925,706 B2 | 2/2021 | Eigler et al. |
| 10,940,296 B2 | 3/2021 | Keren |
| 11,109,988 B2 | 9/2021 | Rosen et al. |
| 11,135,054 B2 | 10/2021 | Nitzan et al. |
| 11,234,702 B1 | 2/2022 | Eigler et al. |
| 11,253,353 B2 | 2/2022 | Levi et al. |
| 11,291,807 B2 | 4/2022 | Eigler et al. |
| 11,304,831 B2 | 4/2022 | Nae et al. |
| 2001/0021872 A1 | 9/2001 | Bailey et al. |
| 2002/0099431 A1 | 7/2002 | Armstrong et al. |
| 2002/0120277 A1 | 8/2002 | Hauschild et al. |
| 2002/0165479 A1 | 11/2002 | Wilk |
| 2002/0165606 A1 | 11/2002 | Wolf et al. |
| 2002/0169371 A1 | 11/2002 | Gilderdale |
| 2002/0169377 A1 | 11/2002 | Khairkhahan et al. |
| 2002/0173742 A1 | 11/2002 | Keren et al. |
| 2002/0183628 A1 | 12/2002 | Reich et al. |
| 2003/0028213 A1 | 2/2003 | Thill et al. |
| 2003/0045902 A1 | 3/2003 | Weadock |
| 2003/0100920 A1 | 5/2003 | Akin et al. |
| 2003/0125798 A1 | 7/2003 | Martin |

(56) References Cited

U.S. PATENT DOCUMENTS

| | | |
|---|---|---|
| 2003/0136417 A1 | 7/2003 | Fonseca et al. |
| 2003/0139819 A1 | 7/2003 | Beer et al. |
| 2003/0176914 A1 | 9/2003 | Rabkin et al. |
| 2003/0209835 A1 | 11/2003 | Chun et al. |
| 2003/0216679 A1 | 11/2003 | Wolf et al. |
| 2003/0216803 A1 | 11/2003 | Ledergerber |
| 2004/0010219 A1 | 1/2004 | McCusker et al. |
| 2004/0016514 A1 | 1/2004 | Nien |
| 2004/0073242 A1 | 4/2004 | Chanduszko |
| 2004/0077988 A1 | 4/2004 | Tweden et al. |
| 2004/0088045 A1 | 5/2004 | Cox |
| 2004/0093075 A1 | 5/2004 | Kuehne |
| 2004/0102797 A1 | 5/2004 | Golden et al. |
| 2004/0116999 A1 | 6/2004 | Ledergerber |
| 2004/0138743 A1 | 7/2004 | Myers et al. |
| 2004/0147869 A1 | 7/2004 | Wolf et al. |
| 2004/0147871 A1 | 7/2004 | Burnett |
| 2004/0147886 A1 | 7/2004 | Bonni |
| 2004/0147969 A1 | 7/2004 | Mann et al. |
| 2004/0162514 A1 | 8/2004 | Alferness et al. |
| 2004/0193261 A1 | 9/2004 | Berreklouw |
| 2004/0210190 A1 | 10/2004 | Kohler et al. |
| 2004/0210307 A1 | 10/2004 | Khairkhahan |
| 2004/0225352 A1 | 11/2004 | Osborne et al. |
| 2005/0003327 A1 | 1/2005 | Elian et al. |
| 2005/0033327 A1 | 2/2005 | Gainor et al. |
| 2005/0033351 A1 | 2/2005 | Newton |
| 2005/0065589 A1 | 3/2005 | Schneider et al. |
| 2005/0125032 A1 | 6/2005 | Whisenant et al. |
| 2005/0137682 A1 | 6/2005 | Justino |
| 2005/0148925 A1* | 7/2005 | Rottenberg ......... A61B 5/0215 604/9 |
| 2005/0165344 A1* | 7/2005 | Dobak, III ............ A61F 2/2476 604/8 |
| 2005/0182486 A1 | 8/2005 | Gabbay |
| 2005/0267524 A1 | 12/2005 | Chanduszko |
| 2005/0283231 A1 | 12/2005 | Haug et al. |
| 2005/0288596 A1 | 12/2005 | Eigler et al. |
| 2005/0288706 A1 | 12/2005 | Widomski et al. |
| 2005/0288786 A1 | 12/2005 | Chanduszko |
| 2006/0009800 A1 | 1/2006 | Christianson et al. |
| 2006/0025857 A1 | 2/2006 | Bergheim et al. |
| 2006/0052821 A1 | 3/2006 | Abbott et al. |
| 2006/0111660 A1 | 5/2006 | Wolf et al. |
| 2006/0111704 A1 | 5/2006 | Brenneman et al. |
| 2006/0116710 A1 | 6/2006 | Corcoran et al. |
| 2006/0122522 A1 | 6/2006 | Chavan et al. |
| 2006/0122647 A1 | 6/2006 | Callaghan et al. |
| 2006/0167541 A1 | 7/2006 | Lattouf |
| 2006/0184231 A1 | 8/2006 | Rucker |
| 2006/0212110 A1 | 9/2006 | Osborne et al. |
| 2006/0241745 A1 | 10/2006 | Solem |
| 2006/0256611 A1 | 11/2006 | Bednorz et al. |
| 2006/0282157 A1 | 12/2006 | Hill et al. |
| 2007/0010852 A1 | 1/2007 | Blaeser et al. |
| 2007/0021739 A1 | 1/2007 | Weber |
| 2007/0043435 A1 | 2/2007 | Seguin et al. |
| 2007/0073337 A1 | 3/2007 | Abbott et al. |
| 2007/0129756 A1 | 6/2007 | Abbott et al. |
| 2007/0191863 A1 | 8/2007 | De Juan, Jr. et al. |
| 2007/0213813 A1 | 9/2007 | Von Segesser et al. |
| 2007/0249985 A1 | 10/2007 | Brenneman et al. |
| 2007/0276413 A1 | 11/2007 | Nobles |
| 2007/0276414 A1 | 11/2007 | Nobles |
| 2007/0282157 A1 | 12/2007 | Rottenberg et al. |
| 2007/0299384 A1 | 12/2007 | Faul et al. |
| 2008/0034836 A1 | 2/2008 | Eigler et al. |
| 2008/0086205 A1 | 4/2008 | Gordy et al. |
| 2008/0125861 A1 | 5/2008 | Webler et al. |
| 2008/0171944 A1 | 7/2008 | Brenneman et al. |
| 2008/0177300 A1 | 7/2008 | Mas et al. |
| 2008/0262602 A1 | 10/2008 | Wilk et al. |
| 2008/0319525 A1 | 12/2008 | Tieu et al. |
| 2009/0030499 A1 | 1/2009 | Bebb et al. |
| 2009/0054976 A1 | 2/2009 | Tuval et al. |
| 2009/0125104 A1 | 5/2009 | Hoffman |
| 2009/0149947 A1 | 6/2009 | Frohwitter |
| 2009/0198315 A1 | 8/2009 | Boudjemline |
| 2009/0276040 A1 | 11/2009 | Rowe et al. |
| 2009/0319037 A1 | 12/2009 | Rowe et al. |
| 2010/0004740 A1 | 1/2010 | Seguin et al. |
| 2010/0022940 A1 | 1/2010 | Thompson |
| 2010/0057192 A1 | 3/2010 | Celermajer |
| 2010/0069836 A1 | 3/2010 | Satake |
| 2010/0070022 A1 | 3/2010 | Kuehling |
| 2010/0081867 A1 | 4/2010 | Fishler et al. |
| 2010/0100167 A1 | 4/2010 | Bortlein et al. |
| 2010/0121434 A1 | 5/2010 | Paul et al. |
| 2010/0179590 A1 | 7/2010 | Fortson et al. |
| 2010/0191326 A1 | 7/2010 | Alkhatib |
| 2010/0249909 A1 | 9/2010 | McNamara et al. |
| 2010/0249910 A1 | 9/2010 | McNamara et al. |
| 2010/0249915 A1 | 9/2010 | Zhang |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2010/0324652 A1 | 12/2010 | Aurilia et al. |
| 2011/0022057 A1 | 1/2011 | Eigler et al. |
| 2011/0022157 A1 | 1/2011 | Essinger et al. |
| 2011/0054515 A1 | 3/2011 | Bridgeman et al. |
| 2011/0071623 A1 | 3/2011 | Finch et al. |
| 2011/0071624 A1 | 3/2011 | Finch et al. |
| 2011/0093059 A1 | 4/2011 | Fischell et al. |
| 2011/0106149 A1* | 5/2011 | Ryan ..................... H04M 1/68 606/213 |
| 2011/0152923 A1 | 6/2011 | Fox |
| 2011/0190874 A1 | 8/2011 | Celermajer et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0257723 A1 | 10/2011 | McNamara |
| 2011/0264203 A1 | 10/2011 | Dwork et al. |
| 2011/0276086 A1 | 11/2011 | Al-Qbandi et al. |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1* | 12/2011 | Nitzan ................. A61F 2/2418 604/9 |
| 2011/0319806 A1 | 12/2011 | Wardle |
| 2012/0022507 A1 | 1/2012 | Najafi et al. |
| 2012/0022633 A1 | 1/2012 | Olson et al. |
| 2012/0035590 A1 | 2/2012 | Whiting et al. |
| 2012/0041422 A1 | 2/2012 | Whiting et al. |
| 2012/0046528 A1 | 2/2012 | Eigler et al. |
| 2012/0046739 A1 | 2/2012 | Von Oepen et al. |
| 2012/0053686 A1 | 3/2012 | McNamara et al. |
| 2012/0071918 A1 | 3/2012 | Amin et al. |
| 2012/0130301 A1 | 5/2012 | McNamara et al. |
| 2012/0165928 A1* | 6/2012 | Nitzan ................. A61F 2/2412 623/2.15 |
| 2012/0179172 A1 | 7/2012 | Paul, Jr. et al. |
| 2012/0190991 A1 | 7/2012 | Bornzin et al. |
| 2012/0265296 A1 | 10/2012 | McNamara et al. |
| 2012/0271398 A1 | 10/2012 | Essinger et al. |
| 2012/0289882 A1 | 11/2012 | McNamara et al. |
| 2012/0290062 A1 | 11/2012 | McNamara et al. |
| 2013/0030521 A1* | 1/2013 | Nitzan ................. A61F 2/2412 623/2.13 |
| 2013/0046373 A1 | 2/2013 | Cartledge et al. |
| 2013/0096965 A1 | 4/2013 | Pappas et al. |
| 2013/0138145 A1 | 5/2013 | Von Oepen |
| 2013/0178783 A1* | 7/2013 | McNamara ........... A61F 2/2493 604/9 |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0197423 A1 | 8/2013 | Keren et al. |
| 2013/0197547 A1 | 8/2013 | Fukuoka et al. |
| 2013/0197629 A1 | 8/2013 | Gainor et al. |
| 2013/0204175 A1 | 8/2013 | Sugimoto |
| 2013/0231737 A1 | 9/2013 | McNamara et al. |
| 2013/0261531 A1 | 10/2013 | Gallagher et al. |
| 2013/0281988 A1 | 10/2013 | Magnin et al. |

(56) References Cited

U.S. PATENT DOCUMENTS

| | | |
|---|---|---|
| 2013/0304192 A1 | 11/2013 | Chanduszko |
| 2013/0331864 A1 | 12/2013 | Jelich et al. |
| 2014/0012181 A1 | 1/2014 | Sugimoto et al. |
| 2014/0012303 A1 | 1/2014 | Heipl |
| 2014/0012368 A1 | 1/2014 | Sugimoto et al. |
| 2014/0012369 A1 | 1/2014 | Murry, III et al. |
| 2014/0067037 A1 | 3/2014 | Fargahi |
| 2014/0094904 A1 | 4/2014 | Salahieh et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0194971 A1 | 7/2014 | McNamara |
| 2014/0213959 A1 | 7/2014 | Nitzan et al. |
| 2014/0222144 A1 | 8/2014 | Eberhardt et al. |
| 2014/0249621 A1 | 9/2014 | Eidenschink |
| 2014/0257167 A1 | 9/2014 | Celermajer |
| 2014/0275916 A1 | 9/2014 | Nabutovsky et al. |
| 2014/0277045 A1 | 9/2014 | Fazio et al. |
| 2014/0277054 A1 | 9/2014 | McNamara et al. |
| 2014/0303710 A1 | 10/2014 | Zhang et al. |
| 2014/0350565 A1 | 11/2014 | Yacoby et al. |
| 2014/0350658 A1 | 11/2014 | Benary et al. |
| 2014/0350661 A1 | 11/2014 | Schaeffer |
| 2014/0350669 A1 | 11/2014 | Gillespie et al. |
| 2014/0357946 A1 | 12/2014 | Golden et al. |
| 2015/0005810 A1 | 1/2015 | Center et al. |
| 2015/0034217 A1 | 2/2015 | Vad |
| 2015/0039084 A1 | 2/2015 | Levi et al. |
| 2015/0066140 A1 | 3/2015 | Quadri et al. |
| 2015/0073539 A1 | 3/2015 | Geiger et al. |
| 2015/0112383 A1 | 4/2015 | Sherman et al. |
| 2015/0119796 A1 | 4/2015 | Finch |
| 2015/0127093 A1 | 5/2015 | Hosmer et al. |
| 2015/0142049 A1 | 5/2015 | Delgado et al. |
| 2015/0148731 A1 | 5/2015 | Mcnamara et al. |
| 2015/0148896 A1 | 5/2015 | Karapetian et al. |
| 2015/0157455 A1 | 6/2015 | Hoang et al. |
| 2015/0173897 A1 | 6/2015 | Raanani et al. |
| 2015/0182334 A1 | 7/2015 | Bourang et al. |
| 2015/0190229 A1 | 7/2015 | Seguin |
| 2015/0196383 A1 | 7/2015 | Johnson |
| 2015/0201998 A1 | 7/2015 | Roy et al. |
| 2015/0209143 A1 | 7/2015 | Duffy et al. |
| 2015/0230924 A1 | 8/2015 | Miller et al. |
| 2015/0238314 A1 | 8/2015 | Bortlein et al. |
| 2015/0245908 A1 | 9/2015 | Nitzan et al. |
| 2015/0272731 A1 | 10/2015 | Racchini et al. |
| 2015/0282790 A1 | 10/2015 | Quinn et al. |
| 2015/0282931 A1 | 10/2015 | Brunnett et al. |
| 2015/0294313 A1 | 10/2015 | Kamal et al. |
| 2015/0313599 A1 | 11/2015 | Johnson et al. |
| 2015/0359556 A1 | 12/2015 | Vardi |
| 2016/0007924 A1 | 1/2016 | Eigler et al. |
| 2016/0022423 A1 | 1/2016 | Mcnamara et al. |
| 2016/0022970 A1 | 1/2016 | Forcucci et al. |
| 2016/0073907 A1 | 3/2016 | Nabutovsky et al. |
| 2016/0120550 A1 | 5/2016 | McNamara et al. |
| 2016/0129260 A1 | 5/2016 | Mann et al. |
| 2016/0157862 A1 | 6/2016 | Hernandez et al. |
| 2016/0166381 A1 | 6/2016 | Sugimoto et al. |
| 2016/0184561 A9 | 6/2016 | McNamara et al. |
| 2016/0206423 A1 | 7/2016 | O'Connor et al. |
| 2016/0213467 A1 | 7/2016 | Backus et al. |
| 2016/0220360 A1 | 8/2016 | Lin et al. |
| 2016/0220365 A1 | 8/2016 | Backus et al. |
| 2016/0262878 A1 | 9/2016 | Backus et al. |
| 2016/0262879 A1 | 9/2016 | Meiri et al. |
| 2016/0287386 A1 | 10/2016 | Alon et al. |
| 2016/0296325 A1 | 10/2016 | Edelman et al. |
| 2016/0361167 A1 | 12/2016 | Tuval et al. |
| 2016/0361184 A1 | 12/2016 | Tabor et al. |
| 2017/0035435 A1 | 2/2017 | Amin et al. |
| 2017/0056171 A1 | 3/2017 | Cooper et al. |
| 2017/0113026 A1 | 4/2017 | Finch |
| 2017/0128705 A1 | 5/2017 | Forcucci et al. |
| 2017/0135685 A9 | 5/2017 | McNamara et al. |
| 2017/0165532 A1 | 6/2017 | Khan et al. |
| 2017/0216025 A1 | 8/2017 | Nitzan et al. |
| 2017/0224323 A1 | 8/2017 | Rowe et al. |
| 2017/0224444 A1 | 8/2017 | Viecilli et al. |
| 2017/0231766 A1 | 8/2017 | Hariton et al. |
| 2017/0273790 A1 | 9/2017 | Vettukattil et al. |
| 2017/0281339 A1 | 10/2017 | Levi et al. |
| 2017/0312486 A1 | 11/2017 | Nitzan et al. |
| 2017/0319823 A1 | 11/2017 | Yacoby et al. |
| 2017/0325956 A1 | 11/2017 | Rottenberg et al. |
| 2017/0340460 A1 | 11/2017 | Rosen et al. |
| 2017/0348100 A1 | 12/2017 | Lane et al. |
| 2018/0099128 A9 | 4/2018 | McNamara et al. |
| 2018/0104053 A1 | 4/2018 | Alkhatib et al. |
| 2018/0110609 A1 | 4/2018 | Ehnes et al. |
| 2018/0125630 A1 | 5/2018 | Hynes et al. |
| 2018/0130988 A1 | 5/2018 | Nishikawa et al. |
| 2018/0243071 A1 | 8/2018 | Eigler et al. |
| 2018/0256865 A1 | 9/2018 | Finch et al. |
| 2018/0263766 A1 | 9/2018 | Nitzan et al. |
| 2018/0280667 A1 | 10/2018 | Keren |
| 2018/0344994 A1 | 12/2018 | Karavany et al. |
| 2019/0000327 A1 | 1/2019 | Doan et al. |
| 2019/0008628 A1 | 1/2019 | Eigler et al. |
| 2019/0015103 A1 | 1/2019 | Sharma |
| 2019/0015188 A1 | 1/2019 | Eigler et al. |
| 2019/0021861 A1 | 1/2019 | Finch |
| 2019/0110911 A1 | 4/2019 | Nae et al. |
| 2019/0239754 A1 | 8/2019 | Nabutovsky et al. |
| 2019/0254814 A1 | 8/2019 | Nitzan et al. |
| 2019/0262118 A1 | 8/2019 | Eigler et al. |
| 2019/0328513 A1 | 10/2019 | Levi et al. |
| 2019/0336163 A1 | 11/2019 | McNamara et al. |
| 2020/0060825 A1 | 2/2020 | Rottenberg et al. |
| 2020/0078196 A1 | 3/2020 | Rosen et al. |
| 2020/0078558 A1 | 3/2020 | Yacoby et al. |
| 2020/0085600 A1 | 3/2020 | Schwartz et al. |
| 2020/0197178 A1 | 6/2020 | Vecchio |
| 2020/0261705 A1 | 8/2020 | Nitzan et al. |
| 2020/0315599 A1 | 10/2020 | Nae et al. |
| 2020/0368505 A1 | 11/2020 | Nae et al. |
| 2021/0052378 A1 | 2/2021 | Nitzan et al. |
| 2021/0100665 A1 | 4/2021 | Nae et al. |
| 2021/0121179 A1 | 4/2021 | Ben-David et al. |
| 2022/0008014 A1 | 1/2022 | Rowe et al. |
| 2022/0211361 A1 | 7/2022 | Rolando et al. |
| 2022/0304803 A1 | 9/2022 | Guyenot et al. |

FOREIGN PATENT DOCUMENTS

| | | |
|---|---|---|
| EP | 1987777 A2 | 11/2008 |
| EP | 2238933 A1 | 10/2010 |
| EP | 2305321 A1 | 4/2011 |
| EP | 1965842 B1 | 11/2011 |
| EP | 3400907 A1 | 11/2018 |
| FR | 2827153 A1 | 1/2003 |
| WO | WO-9531945 A1 | 11/1995 |
| WO | WO-9727898 A1 | 8/1997 |
| WO | WO-9960941 A1 | 12/1999 |
| WO | WO-0044311 A2 | 8/2000 |
| WO | WO-0050100 A1 | 8/2000 |
| WO | WO-0110314 A2 | 2/2001 |
| WO | WO-0126585 A1 | 4/2001 |
| WO | WO-0226281 A1 | 4/2002 |
| WO | WO-02071974 A2 | 9/2002 |
| WO | WO-02087473 A1 | 11/2002 |
| WO | WO-03053495 A2 | 7/2003 |
| WO | WO-2005027752 A1 | 3/2005 |
| WO | WO-2005074367 A2 | 8/2005 |
| WO | WO-2006127765 A1 | 11/2006 |
| WO | WO-2007083288 A2 | 7/2007 |
| WO | WO-2008055301 A1 | 5/2008 |
| WO | WO-2008070797 A2 | 6/2008 |
| WO | WO-2009029261 A1 | 3/2009 |
| WO | WO-2010128501 A1 | 11/2010 |
| WO | WO-2010129089 A2 | 11/2010 |
| WO | WO-2010139771 A2 | 12/2010 |
| WO | WO-2011062858 A1 | 5/2011 |

(56) References Cited

FOREIGN PATENT DOCUMENTS

| | | |
|---|---|---|
| WO | WO-2013096965 A1 | 6/2013 |
| WO | WO-2016178171 A1 | 11/2016 |
| WO | WO-2017118920 A1 | 7/2017 |
| WO | WO-2018158747 A1 | 9/2018 |
| WO | WO-2019015617 A1 | 1/2019 |
| WO | WO-2019085841 A1 | 5/2019 |
| WO | WO-2019109013 A1 | 6/2019 |
| WO | WO-2019142152 A1 | 7/2019 |
| WO | WO-2019179447 A1 | 9/2019 |
| WO | WO-2019218072 A1 | 11/2019 |
| WO | WO-2020206062 A1 | 10/2020 |
| WO | WO-2020257530 A1 | 12/2020 |
| WO | WO-2021050589 A1 | 3/2021 |
| WO | WO-2021113670 A1 | 6/2021 |
| WO | WO-2021212011 A2 | 10/2021 |
| WO | WO-2021224736 A1 | 11/2021 |
| WO | WO-2022046921 A1 | 3/2022 |
| WO | WO-2022076601 A1 | 4/2022 |
| WO | WO-2022091018 A1 | 5/2022 |
| WO | WO-2022091019 A1 | 5/2022 |
| WO | WO-2022103973 A1 | 5/2022 |

OTHER PUBLICATIONS

Abraham et al., "Sustained efficacy of pulmonary artery pressure to guide adjustment of chronic heart failure therapy: complete follow-up results from the CHAMPION randomised trial," The Lancet, doi.org/10.1016/S0140-6736(15)00723-0 (2015).
Abraham et al., "Wireless pulmonary artery haemodynamic monitoring in chronic heart failure: a randomised controlled trial," The Lancet, DOI:10.1016/S0140-6736(11)60101-3 (2011).
Abreu et al., "Doppler ultrasonography of the femoropopliteal segment in patients with venous ulcer," J Vasc Bras., 11(4):277-285 (2012).
Adamson et al., "Ongoing Right Ventricular Hemodynamics in Heart Failure Clinical Value of Measurements Derived From an Implantable Monitoring System," J Am Coll Cardiol., 41(4):565-571 (2003).
Adamson et al., "Wireless Pulmonary Artery Pressure Monitoring Guides Management to Reduce Decompensation in Heart Failure With Preserved Ejection Fraction," Circ Heart Fail., 7:935-944 (2014).
Ambrosy et al. "The Global Health and Economic Burden of Hospitalizations for Heart Failure," J Am Coll Cardiol., 63:1123-1133 (2014).
Aminde et al., "Current diagnostic and treatment strategies for Lutembacher syndrome: the pivotal role of echocardiography," Cardiovasc Diagn Ther., 5(2):122-132 (2015).
Anderas E. "Advanced MEMS Pressure Sensors Operating in Fluids," Digital Comprehensive Summaries of Uppsala Dissertation from the Faculty of Science and Technology 933. Uppsala ISBN 978-91-554-8369-2 (2012).
Anderas et al., "Tilted c-axis Thin-Film Bulk Wave Resonant Pressure Sensors with Improved Sensitivity," IEEE Sensors J., 12(8):2653-2654 (2012).
Ando, et al., Left ventricular decompression through a patent foramen ovale in a patient with hypertrophic cardiomyopathy: A case report, Cardiovascular Ultrasound, 2: 1-7 (2004).
Article 34 Amendments dated May 28, 2013 in Int'l PCT Patent Appl. Serial No. PCT/IB2012/001859 (0810).
Article 34 Amendments dated Nov. 27, 2012 in Int'l PCT Patent Appl. Serial No. PCT/IL2011/000958 (0710).
Ataya et al., "A Review of Targeted Pulmonary Arterial Hypertension-Specific Pharmacotherapy," J. Clin. Med., 5(12):114 (2016).
"Atrium Advanta V12, Balloon Expandable Covered Stent, Improving Patient Outcomes with An Endovascular Approach," Brochure, 8 pages, Getinge (2017).
Bannan et al., "Characteristics of Adult Patients with Atrial Septal Defects Presenting with Paradoxical Embolism.," Catheterization and Cardiovascular Interventions, 74:1066-1069 (2009).

Baumgartner et al., "ESC Guidelines for the management of grown-up congenital heart disease (new version 2010)—The Task Force on the Management of Grown-up Congenital Heart Disease of the European Society of Cardiology (ESC)," Eur Heart J., 31:2915-2957 (2010).
Beemath et al., "Pulmonary Embolism as a Cause of Death in Adults Who Died With Heart Failure," Am J Cardiol., 98:1073-1075 (2006).
Benza et al., "Monitoring Pulmonary Arterial Hypertension Using an Implantable Hemodynamic Sensor," CHEST, 156(6):1176-1186 (2019).
Boehm, et al., "Balloon Atrial Septostomy: History and Technique," Images Paeditr. Cardiol., 8(1):8-14 (2006).
Borlaug, et al., Latent Pulmonary Vascular Disease May Alter The Response to Therapeutic Atrial Shunt Device in Heart Failure, Circulation (Mar. 2022).
Braunwald, Heart Disease, Chapter 6, pp. 186.
Bridges, et al., "The Society of Thoracic Surgeons Practice Guideline Series: Transmyocardial Laser Revascularization," Ann Thorac Surg., 77:1494-1502 (2004).
Bristow, et al., "Improvement in cardiac myocite function by biological effects of medical therapy: a new concept in the treatment of heart failure," European Heart Journal, 16 (Suppl.F): 20-31 (1995).
Bruch et al., "Fenestrated Occluders for Treatment of ASD in Elderly Patients with Pulmonary Hypertension and/or Right Heart Failure," J Interven Cardiol., 21(1):44-49 (2008).
Burkhoff et al., "Assessment of systolic and diastolic ventricular properties via pressure-volume analysis: a guide for clinical, translational, and basic researchers," Am J Physiol Heart Circ Physiol., 289:H501-H512 (2005).
Butler et al. "Recognizing Worsening Chronic Heart Failure as an Entity and an End Point in Clinical Trials," JAMA., 312(8):789-790 (2014).
Case, et al., "Relief of High Left-Atrial Pressure in Left-Ventricular Failure," Lancet, (pp. 841-842), Oct. 17, 1964.
Chakko et al., "Clinical, radiographic, and hemodynamic correlations in chronic congestive heart failure: conflicting results may lead to inappropriate care," Am J Medicine, 90:353-359 (1991) (Abstract Only).
Chang et al., "State-of-the-art and recent developments in micro/nanoscale pressure sensors for smart wearable devices and health monitoring systems," Nanotechnology and Precision Engineering, 3:43-52 (2020).
Chen et al., "Continuous wireless pressure monitoring and mapping with ultra-small passive sensors for health monitoring and critical care," Nature Communications, 5(1):1-10 (2014).
Chen et al., "National and Regional Trends in Heart Failure Hospitalization and Mortality Rates for Medicare Beneficiaries, 1998-2008," JAMA, 306(15):1669-1678 (2011).
Chiche et al., "Prevalence of patent foramen ovale and stroke in pulmonary embolism patients," Eur Heart J., 34:P1142 (2013) (Abstract Only).
Chin et al., "The right ventricle in pulmonary hypertension," Coron Artery Dis., 16(1):13-18 (2005) (Abstract Only).
Chun et al., "Lifetime Analysis of Hospitalizations and Survival of Patients Newly Admitted With Heart Failure," Circ Heart Fail., 5:414-421 (2012).
Ciarka et al., "Atrial Septostomy Decreases Sympathetic Overactivity in Pulmonary Arterial Hypertension," Chest, 131(6):P1831-1837 (2007) (Abstract Only).
Cleland et al., "The EuroHeart Failure survey programme—a survey on the quality of care among patients with heart failure in Europe—Part 1: patient characteristics and diagnosis," Eur Heart J., 24:442-463 (2003).
Clowes et al., "Mechanisms of Arterial Graft Healing—Rapid Transmural Capillary Ingrowth Provides a Source of Intimal Endothelium and Smooth Muscle in Porous PTFE Prostheses," Am J Pathol., 123:220-230 (1986).
Coats, et al., "Controlled Trial of Physical Training in Chronic Heart Failure: Exercise Performance, Hemodynamics, Ventilation, and Autonomic Function," Circulation, 85:2119-2131 (1992).

(56) References Cited

OTHER PUBLICATIONS

Davies et al., "Abnormal left heart function after operation for atrial septal defect," British Heart Journal, 32:747-753 (1970).

Davies, et al., "Reduced Contraction and Altered Frequency Response of Isolated Ventricular Myocytes From Patients With Heart Failure, Circulation," 92: 2540-2549 (1995).

Del Trigo et al., "Unidirectional Left-To-Right Interatrial Shunting for Treatment of Patients with Heart Failure with Reduced Ejection Fraction: a Safety and Proof-of-Principle Cohort Study," Lancet, 387:1290-1297 (2016).

Della Lucia et al., "Design, fabrication and characterization of SAW pressure sensors for offshore oil and gas exploration," Sensors and Actuators A: Physical, 222:322-328 (2015).

Drazner et al., "Prognostic Importance of Elevated Jugular Venous Pressure and a Third Heart Sound in Patients with Heart Failure," N Engl J Med., 345(8):574-81 (2001).

Drazner et al., "Relationship between Right and Left-Sided Filling Pressures in 1000 Patients with Advanced Heart Failure," Heart Lung Transplant, 18:1126-1132 (1999).

Drexel, et al., "The Effects of Cold Work and Heat Treatment on the Properties of Nitinol Wire, Proceedings of the International Conference on Shape Memory and Superelastic Technologies, SMST 2006," Pacific Grove, California, USA (pp. 447-454) May 7-11, 2006.

Eigler et al., "Cardiac Unloading with an Implantable Interatrial Shunt in Heart Failure: Serial Observations in an Ovine Model of Ischemic Cardiomyopathy," Structural Heart, 1:40-48 (2017).

Eigler, et al., Implantation and Recovery of Temporary Metallic Stents in Canine Coronary Arteries, JACC, 22(4):1207-1213 (1993).

Ennezat, et al., An unusual case of low-flow, low gradient severe aortic stenosis: Left-to-right shunt due to atrial septal defect, Cardiology, 113(2):146-148, (2009).

Eshaghian et al., "Relation of Loop Diuretic Dose to Mortality in Advanced Heart Failure," Am J Cardiol., 97:1759-1764 (2006).

Ewert, et al., Acute Left Heart Failure After Interventional Occlusion of An Artial Septal Defect, Z Kardiol, 90(5): 362-366 (May 2001).

Ewert, et al., Masked Left Ventricular Restriction in Elderly Patients With Atrial Septal Defects: A Contraindication for Closure?, Catheterization and Cardiovascular Intervention, 52:177-180 (2001).

Extended European Search Report dated Jan. 8, 2015 in EP Patent Appl No. 10772089.8. (0530).

Extended European Search Report dated Mar. 29, 2019 in EP Patent Appl. Serial No. EP16789391 (1830).

Extended European Search Report dated Sep. 19, 2016 in EP Patent Appl. No. 16170281.6 (0731).

Feldman et al., "Transcatheter Interatrial Shunt Device for the Treatment of Heart Failure with Preserved Ejection Fraction (Reduce LAP-HF I [Reduce Elevated Left Atrial Pressure in Patients With Heart Failure]), A Phase 2, Randomized, Sham-Controlled Trial," Circulation, 137:364-375 (2018).

Ferrari et al., "Impact of pulmonary arterial hypertension (PAH) on the lives of patients and carers: results from an international survey," Eur Respir J., 42:26312 (2013) (Abstract Only).

Flachskampf, et al., Influence of Orifice Geometry and Flow Rate on Effective Valve Area: An In Vitro Study, Journal of the American College of Cardiology, 15(5):1173-1180 (Apr. 1990).

Fonarow et al., "Characteristics, Treatments, and Outcomes of Patients With Preserved Systolic Function Hospitalized for Heart Failure," J Am Coll Cardiol., 50(8):768-777 (2007).

Fonarow et al., "Risk Stratification for In-Hospital Mortality in Acutely Decompensated Heart Failure: Classification and Regression Tree Analysis," JAMA, 293(5):572-580 (2005).

Fonarow, G., "The Treatment Targets in Acute Decompensated Heart Failure," Rev Cardiovasc Med., 2:(2):S7-S12 (2001).

Galie et al., "2015 ESC/ERS Guidelines for the diagnosis and treatment of pulmonary hypertension—The Joint Task Force for the Diagnosis and Treatment of Pulmonary Hypertension of the European Society of Cardiology (ESC) and the European Respiratory Society (ERS)," European Heart Journal, 37:67-119 (2016).

Galie et al., "Pulmonary arterial hypertension: from the kingdom of the near-dead to multiple clinical trial meta-analyses," Eur Heart J., 31:2080-2086 (2010).

Galipeau et al., "Surface acoustic wave microsensors and applications," Smart Materials and Structures, 6(6):658-667 (1997) (Abstract Only).

Geiran, et al., Changes in cardiac dynamics by opening an interventricular shunt in dogs, J. Surg. Res. 48(1):6-12 (1990).

Gelernter-Yaniv, et al., Transcatheter ClosureoOf Left-To-Right Interatrial Shunts to Resolve Hypoxemia, Congenit. Heart Dis. 31(1): 47-53 (Jan. 2008).

Geva et al., "Atrial septal defects," Lancet, 383:1921-32 (2014).

Gewillig, et al., Creation with a stent of an unrestrictive lasting atrial communication, Cardio. Young 12(4): 404-407 (2002).

Gheorghiade et al., "Acute Heart Failure Syndromes, Current State and Framework for Future Research," Circulation, 112:3958-3968 (2005).

Gheorghiade et al., "Effects of Tolvaptan, a Vasopressin Antagonist, in Patients Hospitalized With Worsening Heart Failure A Randomized Controlled Trial," JAMA., 291:1963-1971 (2004).

Go et al. "Heart Disease and Stroke Statistics—2014 Update—A Report From the American Heart Association," Circulation, 128:1-267 (2014).

Guillevin et al., "Understanding the impact of pulmonary arterial hypertension on patients' and carers' lives," Eur Respir Rev., 22:535-542 (2013).

Guyton et al., "Effect of Elevated Left Atrial Pressure and Decreased Plasma Protein Concentration on the Development of Pulmonary Edema," Circulation Research, 7:643-657 (1959).

Hasenfub, et al., A Transcatheter Intracardiac Shunt Device for Heart Failure with Preserved Ejection Fraction (Reduce LAP-HF): A Multicentre, Open-Label, Single-Arm, Phase 1 Trial, www.thelancet.com, 387:1298-1304 (2016).

Hoeper et al., "Definitions and Diagnosis of Pulmonary Hypertension," J Am Coll Cardiol., 62(5):D42-D50 (2013).

Hogg et al., "Heart Failure With Preserved Left Ventricular Systolic Function. Epidemiology, Clinical Characteristics, and Prognosis," J Am Coll Cardiol., 43(3):317-327 (2004).

Howell et al., "Congestive heart failure and outpatient risk of venous thromboembolism: A retrospective, case-control study," Journal of Clinical Epidemiology, 54:810-816 (2001).

Huang et al., "Remodeling of the chronic severely failing ischemic sheep heart after coronary microembolization: functional, energetic, structural, and cellular responses," Am J Physiol Heart Circ Physiol., 286:H2141-H2150 (2004).

Humbert et al., "Pulmonary Arterial Hypertension in France—Results from a National Registry," Am J Respir Crit Care Med., 173:1023-1030 (2006).

International Search Report & Written Opinion dated Nov. 7, 2016 in Int'l PCT Patent Appl. Serial No. PCT/IB2016/052561 (1810).

International Search Report & Written Opinion dated May 29, 2018 in Int'l PCT Patent Appl. Serial No. PCT/IB2018/051385 (1310).

International Search Report & Written Opinion dated Feb. 6, 2013 in Int'l PCT Patent Appl. No. PCT/IB2012/001859, 12 pages (0810).

International Search Report & Written Opinion dated Feb. 7, 2020 in Int'l PCT Patent Appl. Serial No. PCT/IB2019/060257 (1410).

International Search Report & Written Opinion dated Feb. 9, 2022 in Int'l PCT Patent Appl. Serial No. PCT/IB2021/060473 (2010).

International Search Report & Written Opinion dated May 13, 2019 in Int'l PCT Patent Appl. No. PCT/IB2019/050452 (1610).

International Search Report & Written Opinion dated May 17, 2022 in Int'l PCT Patent Appl. Serial No. PCT/IB2022/051177 (2310).

International Search Report & Written Opinion dated May 29, 2018 in Int'l PCT Patent Appl. Serial No. PCTIB2018/051355 (1310).

International Search Report & Written Opinion dated Jul. 14, 2020 in Int'l PCT Patent Appl. Serial No. PCT/IB2020/053832 (1210).

International Search Report & Written Opinion dated Jul. 20, 2020 in Int'l PCT Patent Appl. Serial No. PCT/IB2020/054699 (1710).

International Search Report & Written Opinion dated Jul. 23, 2021 in Int'l PCT Patent Appl. Serial No. PCT/IB2021/053594 (1910).

International Search Report & Written Opinion dated Aug. 12, 2020 in Int'l PCT Patent Appl. Serial No. PCT/IB2020/053118 (1010).

(56) References Cited

OTHER PUBLICATIONS

International Search Report & Written Opinion dated Aug. 28, 2012 in Int'l PCT Patent Appl. No. PCT/IL2011/000958 (0710).
International Search Report & Written Opinion dated Sep. 21, 2020 in Int'l PCT Patent Appl. Serial No. PCT/IB2020/054306 (1510).
International Search Report & Written Opinion dated Oct. 11, 2017 in Int'l PCT Patent Appl. Serial No. PCT/IB2017/053188 (1110).
International Search Report & Written Opinion dated Oct. 26, 2007 in Int'l PCT Patent Appl. Serial No. PCT/IB07/50234 (0610).
International Search Report dated Apr. 7, 2008 in Int'l PCT Patent Appl. Serial No. PCT/IL05/00131 (0410).
International Search Report dated Aug. 25, 2010 in Intl PCT Patent Appl. Serial No. PCT/IL2010/000354 (0510).
ISR & Written Opinion dated Feb. 16, 2015 in Int'l PCT Patent Appl. Serial No. PCT/IB2014/001771 (0910).
Jessup et al. "2009Focused Update: ACC/AHA Guidelines for the Diagnosis and Management of Heart Failure in Adults: A Report of the American College of Cardiology Foundation/American Heart Association Task Force on Practice Guidelines: Developed in Collaboration With the International Society for Heart and Lung Transplantation," J. Am. Coll. Cardiol., 53:1343-1382 (2009).
Jiang, G., "Design challenges of implantable pressure monitoring system," Frontiers in Neuroscience, 4(29):1-4 (2010).
Kane et al., "Integration of clinical and hemodynamic parameters in the prediction of long-term survival in patients with pulmonary arterial hypertension," Chest, 139(6):1285-1293 (2011) (Abstract Only).
Kaye et al., "Effects of an Interatrial Shunt on Rest and Exercise Hemodynamics: Results of a Computer Simulation in Heart Failure," Journal of Cardiac Failure, 20(3): 212-221 (2014).
Kaye et al., "One-Year Outcomes After Transcatheter Insertion of an Interatrial Shunt Device for the Management of Heart Failure With Preserved Ejection Fraction," Circulation: Heart Failure, 9(12):e003662 (2016).
Kaye, et al., One-Year Outcomes After Transcatheter Insertion of an Interatrial Shunt Device for the Management of Heart Failure with Preserved Ejection Fraction, Circulation: Heart Failure, 9(12):e003662 (Dec. 2016).
Keogh et al., "Interventional and Surgical Modalities of Treatment in Pulmonary Hypertension," J Am Coll Cardiol., 54:S67-77 (2009).
Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).
Kramer, et al., Controlled Trial of Captopril in Chronic Heart Failure: A Rest and Exercise Hemodynamic Study, Circulation, 67(4): 807-816, 1983.
Kretschmar et al., "Shunt Reduction With a Fenestrated Amplatzer Device," Catheterization and Cardiovascular Interventions, 76:564-571 (2010).
Kropelnicki et al., "CMOS-compatible ruggedized high-temperature Lamb wave pressure sensor," J. Micromech. Microeng., 23:085018 pp. 1-9 (2013).
Krumholz et al., "Patterns of Hospital Performance in Acute Myocardial Infarction and Heart Failure 30-Day Mortality and Readmission," Circ Cardiovasc Qual Outcomes, 2:407-413 (2009).
Kulkarni et al., "Lutembacher's syndrome," J Cardiovasc Did Res., 3(2):179-181 (2012).
Kurzyna et al., "Atrial Septostomy in Treatment of End-Stage Right Heart Failure in Patients With Pulmonary Hypertension," Chest, 131:977-983 (2007).
Lai et al., Bidirectional Shunt Through a Residual Atrial Septal Defect After Percutaneous Transvenous Mitral Commissurotomy, Cadiology, 83(3): 205-207 (1993).
Lammers et al., "Efficacy and Long-Term Patency of Fenerstrated Amplatzer Devices in Children," Catheter Cardiovasc Interv., 70:578-584 (2007).
Lemmer, et al., Surgical Implications of Atrial Septal Defect Complicating Aortic Balloon Valvuloplasty, Ann. thorac. Surg, 48(2):295-297 (Aug. 1989).

Lindenfeld et al. "Executive Summary: HFSA 2010 Comprehensive Heart Failure Practice Guideline," J. Cardiac Failure, 16(6):475-539 (2010).
Luo, Yi, Selective and Regulated RF Heating of Stent Toward Endohyperthermia Treatment of In-Stent Restenosis, A Thesis Submitted in Partial Fulfillment of The Requirements For The Degree of Master of Applied Science in The Faculty of Graduate and Postdoctoral Studies (Electrical and Computer Engineering), The University of British Columbia, Vancouver, Dec. 2014.
Macdonald et al., "Emboli Enter Penetrating Arteries of Monkey Brain in Relation to Their Size," Stroke, 26:1247-1251 (1995).
Maluli et al., "Atrial Septostomy: A Contemporary Review," Clin. Cardiol., 38(6):395-400 (2015).
Maurer et al., "Rationale and Design of the Left Atrial Pressure Monitoring to Optimize Heart Failure Therapy Study (LAPTOP-HF)," Journal of Cardiac Failure., 21(6): 479-488 (2015).
McClean et al., "Noninvasive Calibration of Cardiac Pressure Transducers in Patients With Heart Failure: An Aid to Implantable Hemodynamic Monitoring and Therapeutic Guidance," J Cardiac Failure, 12(7):568-576 (2006).
McLaughlin et al., "Management of Pulmonary Arterial Hypertension," J Am Coll Cardiol., 65(18):1976-1997 (2015).
McLaughlin et al., "Survival in Primary Pulmonary Hypertension—The Impact of Epoprostenol Therapy.," Circulation, 106:1477-1482 (2002).
Merriam-Webster OnLine Dictionary, Definition of "chamber", printed Dec. 20, 2004.
Mu et al., "Dual mode acoustic wave sensor for precise pressure reading," Applied Physics Letters, 105:113507-1-113507-5 (2014).
Nagaraju et al., "A 400µW Differential FBAR Sensor Interface IC with digital readout," IEEE., pp. 218-221 (2015).
Noordegraaf et al., "The role of the right ventricle in pulmonary arterial hypertension," Eur Respir Rev., 20(122):243-253 (2011).
O'Byrne et al., "The effect of atrial septostomy on the concentration of brain-type natriuretic peptide in patients with idiopathic pulmonary arterial hypertension," Cardiology in the Young, 17(5):557-559 (2007) (Abstract Only).
Oktay et al., "The Emerging Epidemic of Heart Failure with Preserved Ejection Fraction," Curr Heart Fail Rep., 10(4):1-17 (2013).
Owan et al., "Trends in Prevalence and Outcome of Heart Failure with Preserved Ejection Fraction," N Engl J Med., 355:251-259 (2006).
Paitazoglou et al., "Title: The AFR-Prelieve Trial: A prospective, non-randomized, pilot study to assess the Atrial Flow Regulator (AFR) in Heart Failure Patients with either preserved or reduced ejection fraction," EuroIntervention, 28:2539-50 (2019).
Park Blade Septostomy Catheter Instructions for Use, Cook Medical, 28 pages, Oct. 2015.
Park, et al., Blade Atrial Septostomy: Collaborative Study, Circulation, 66(2):258-266 (1982).
Partial Supplemental European Search Report dated Dec. 11, 2018 in EP Patent Appl. Serial No. 16789391.6 (1830).
Peters et al., "Self-fabricated fenestrated Amplatzer occluders for transcatheter closure of atrial septal defect in patients with left ventricular restriction: midterm results," Clin Res Cardiol., 95:88-92 (2006).
Ponikowski et al., "2016 ESC Guidelines for the diagnosis and treatment of acute and chronic heart failure. The Task Force for the diagnosis and treatment of acute and chronic heart failure of the European Society of Cardiology (ESC)," Eur Heart J., doi:10.1093/eurheartj/ehw128 (2016).
Potkay, J. A., "Long term, implantable blood pressure monitoring systems," Biomed Microdevices, 10:379-392 (2008).
Pretorious et al., "An Implantable Left Atrial Pressure Sensor Lead Designed for Percutaneous Extraction Using Standard Techniques," PACE, 00:1-8 (2013).
Rajeshkumar et al., "Atrial septostomy with a predefined diameter using a novel occlutech atrial flow regulator improves symptoms and cardiac index in patients with severe pulmonary arterial hypertension," Catheter Cardiovasc Interv., 1-9 (2017).

(56) References Cited

OTHER PUBLICATIONS

Rich et al., "Atrial Septostomy as Palliative Therapy for Refractory Primary Pulmonary Hypertension," Am J Cardiol., 51:1560-1561 (1983).
Ritzema et al., "Direct Left Atrial Pressure Monitoring in Ambulatory Heart Failure Patients—Initial Experience With a New Permanent Implantable Device," Circulation, 116:2952-2959 (2007).
Ritzema et al., "Physician-Directed Patient Self-Management of Left Atrial Pressure in Advanced Chronic Heart Failure," Circulation, 121:1086-1095 (2010).
Roberts et al., "Integrated microscopy techniques for comprehensive pathology evaluation of an implantable left atrial pressure sensor," J Histotechnology, 36(1):17-24 (2013).
Rodes-Cabau et al., "Interatrial Shunting for Heart Failure Early and Late Results From the First-in-Human Experience With the V-Wave System," J Am Coll Cardiol Intv., 11:2300- 2310.doi:10.1016/j.cin.2018.07.001 (2018).
Rosenquist et al., Atrial Septal Thickness and Area in Normal Heart Specimens and in Those With Ostium Secundum Atrial Septal Defects, J. Clin. Ultrasound, 7:345-348 (1979).
Ross et al., "Interatrial Communication and Left Atrial Hypertension - A Cause of Continuous Murmur," Circulation, 28:853-860 (1963).
Rossignol, et al., Left-to-Right Atrial Shunting: New Hope for Heart Failure, www.thelancet.com, 387:1253-1255 (2016).
Roven, Effect of Compromising Right Ventricular Function in Left Ventricular Failure by Means of Interatrial and Other Shunts 24:209-219 (Aug. 1969).
Salehian, et al., Improvements in Cardiac Form and Function After Transcatheter Closure of Secundum Atrial Septal Defects, Journal of the American College of Cardiology, 45(4):499-504 (2005).
Sandoval et al., "Effect of atrial septostomy on the survival of patients with severe pulmonary arterial hypertension," Eur Respir J., 38:1343-1348 (2011).
Sandoval et al., "Graded Balloon Dilation Atrial Septostomy in Severe Primary Pulmonary Hypertension—A Therapeutic Alternative for Patients Nonresponsive to Vasodilator Treatment," JACC, 32(2):297-304 (1998).
Schiff et al., "Decompensated heart failure: symptoms, patterns of onset, and contributing factors," Am J. Med., 114(8):625-630 (2003) (Abstract Only).
Schmitto, et al., Chronic Heart Failure Induced by Multiple Sequential Coronary Microembolization in sheep, The International Journal of Artificial Organs, 31(4):348-353 (2008).
Schneider et al., "Fate of a Modified Fenestration of Atrial Septal Occluder Device after Transcatheter Closure of Atrial Septal Defects in Elderly Patients," J Interven Cardiol., 24:485-490 (2011).
Scholl et al., "Surface Acoustic Wave Devices for Sensor Applications," Phys Status Solidi Appl Res., 185(1):47-58 (2001) (Abstract Only).
Schubert, et al., Left ventricular Conditioning in the Elderly Patient to Prevent Congestive Heart Failure After Transcatheter Closure of the Atrial Septal Defect, Catheterization and Cardiovascular Interventions, 64(3): 333-337 (2005).
Setoguchi et al., "Repeated hospitalizations predict mortality in the community population with heart failure," Am Heart J., 154:260-266 (2007).
Shah, et al., Atrial Shunt Device For Heart Failure With Preserved And Mildly Reduced Ejection Fraction (Reduce LAP-HF II): A Randomised, Multicentre, Blinded, Sham-Controlled Trial, The Lancet, 399(10330):1130-1140 (Mar. 2022).
Shah et al., "Heart Failure With Preserved, Borderline, and Reduced Ejection Fraction—5-Year Outcomes," J Am Coll Cardiol., https://doi.org/10.1016/j.jacc.2017.08.074 (2017).
Shah et al., "One-Year Safety and Clinical Outcomes of a Transcatheter Interatrial Shunt Device for the Treatment of Heart Failure With Preserved Ejection Fraction in the Reduce Elevated Left Atrial Pressure in Patients With Heart Failure (Reduce LAP-HF I) Trial—A Randomized Clinical Trial," JAMA Cardiol. doi:10.1001/jamacardio.2018.2936 (2018).
Sitbon et al., "Selexipag for the Treatment of Pulmonary Arterial Hypertension.," N Engl J Med., 373(26):2522-2533 (2015).
Sitbon et al., "Epoprostenol and pulmonary arterial hypertension: 20 years of clinical experience," Eur Respir Rev., 26:160055:1-14 (2017).
Steimle et al., "Sustained Hemodynamic Efficacy of Therapy Tailored to Reduce Filling Pressures in Survivors With Advanced Heart Failure," Circulation, 96:1165-1172 (1997).
Stevenson et al., "The Limited Reliability of Physical Signs for Estimating Hemodynamics in Chronic Heart Failure," JAMA, 261(6):884-888 (1989) (Abstract Only).
Stormer, et al., Comparative Study of in Vitro Flow Characteristics Between a Human Aortic Valve and a Designed Aortic Valve and Six Corresponding Types of Prosthetic Heart Valves, European Surgical Research 8(2):117-131 (1976).
Stumper, et al., Modified Technique of Stent Fenestration of the Atrial Septum, Heart, 89:1227-1230, (2003).
Su et al., "A film bulk acoustic resonator pressure sensor based on lateral field excitation," International Journal of Distributed Sensor Networks, 14(11):1-8 (2018).
Supplementary European Search Report dated Nov. 13, 2009 in EP Patent Appl. Serial No. 05703174.2 (0430).
Thenappan et al., "Evolving Epidemiology of Pulmonary Arterial Hypertension," Am J Resp Critical Care Med., 186:707-709 (2012).
Tomai et al., "Acute Left Ventricular Failure After Transcatheter Closure of a Secundum Atrial Septal Defect in a Patient With Coronary Artery Disease: A Critical Reappraisal," Catheterization and Cardiovascular Interventions, 55:97-99 (2002).
Torbicki et al., "Atrial Septostomy," The Right Heart, 305-316 (2014).
Trainor, et al., Comparative Pathology of an Implantable Left Atrial Pressure Sensor, ASAIO Journal, Clinical Cardiovascular/Cardiopulmonary Bypass, 59(5):486-492 (2013).
Troost et al., "A Modified Technique of Stent Fenestration of the Interatrial Septum Improves Patients With Pulmonary Hypertension," Catheterization and Cardiovascular Interventions, 73:173179 (2009).
Troughton et al., "Direct Left Atrial Pressure Monitoring in Severe Heart Failure: Long-Term Sensor Performance," J. of Cardiovasc. Trans. Res., 4:3-13 (2011).
Vank-Noordegraaf et al., "Right Heart Adaptation to Pulmonary Arterial Hypertension—Physiology and Pathobiology," J Am Coll Cardiol., 62(25): D22-33 (2013).
Verel et al., "Comparison of left atrial pressure and wedge pulmonary capillary pressure—Pressure gradients between left atrium and left ventricle," British Heart J., 32:99-102 (1970).
Viaene et al., "Pulmonary oedema after percutaneous ASD-closure," Acta Cardiol., 65(2):257-260 (2010).
Wang et al., "A Low Temperature Drifting Acoustic Wave Pressure Sensor with an Integrated Vacuum Cavity for Absolute Pressure Sensing," Sensors, 20(1788):1-13 (2020).
Warnes et al., "ACC/AHA 2008 Guidelines for the Management of Adults With Congenital Heart Disease—A Report of the American College of Cardiology/American Heart Association Task Force on Practice Guidelines (Writing Committee to Develop Guidelines on the Management of Adults With Congenital Heart Disease)," JACC, 52(23):e143-e263 (2008).
Webb et al., "Atrial Septal Defects in the Adult Recent Progress and Overview," Circulation, 114:1645-1653 (2006).
Wiedemann, H.R., "Earliest description by Johann Friedrich Meckel, Senior (1750) of what is known today as Lutembacher syndrome (1916)," Am J Med Genet., 53(1):59-64 (1994) (Abstract Only).
Written Opinion of the International Searching Authority dated Apr. 7, 2008 in Int'l PCT Patent Appl. Serial No. PCT/IL05/00131 (0410).
Yantchev et al., "Thin Film Lamb Wave Resonators in Frequency Control and Sensing Applications: A Review," Journal of Micromechanics and Microengineering, 23(4):043001 (2013).
Zhang et al., "Acute left ventricular failure after transcatheter closure of a secundum atrial septal defect in a patient with hypertrophic cardiomyopathy," Chin Med J., 124(4):618-621 (2011).

(56) References Cited

OTHER PUBLICATIONS

Zhang et al., "Film bulk acoustic resonator-based high-performance pressure sensor integrated with temperature control system," J Micromech Microeng., 27(4):1-10 (2017).
Zhou, et al., Unidirectional Valve Patch for Repair of Cardiac Septal Defects with Pulmonary Hypertension, Annals of Thoracic Surgeons, 60:1245-1249, (1995).
U.S. Appl. No. 09/839,643 / U.S. Pat. No. 8,091,556 filed Apr. 20, 2001 / Jan. 10, 2012.
U.S. Appl. No. 10/597,666 / U.S. Pat. No. 8,070,708 filed Jun. 20, 2007 / Dec. 6, 2011.
U.S. Appl. No. 12/223,080 / U.S. Pat. No. 9,681,948 filed Jul. 16, 2014 / Jun. 20, 2017.
U.S. Appl. No. 13/107,832 / U.S. Pat. No. 8,235,933 filed May 13, 2011 / Aug. 7, 2012.
U.S. Appl. No. 13/107,843 / U.S. Pat. No. 8,328,751 filed May 13, 2011 / Dec. 11, 2012.
U.S. Appl. No. 13/108,672 / U.S. Pat. No. 9,724,499 filed May 16, 2011 / Aug. 8, 2017.
U.S. Appl. No. 13/108,698, filed Jun. 16, 2011.
U.S. Appl. No. 13/108,850, filed May 16, 2011.
U.S. Appl. No. 13/108,880 / U.S. Pat. No. 8,696,611 filed May 16, 2011 / Apr. 15, 2014.
U.S. Appl. No. 13/193,309 / U.S. Pat. No. 9,629,715 filed Jul. 28, 2011 / Apr. 25, 2017.
U.S. Appl. No. 13/193,335 / U.S. Pat. No. 9,034,034 filed Jul. 28, 2011 / May 19, 2015.
U.S. Appl. No. 13/708,794 / U.S. Pat. No. 9,943,670 filed Dec. 7, 2012 / Apr. 17, 2018.
U.S. Appl. No. 14/154,080 / U.S. Pat. No. 10,207,807 filed Jan. 13, 2014 / Feb. 19, 2019.
U.S. Appl. No. 14/154,088, filed Jan. 13, 2014.
U.S. Appl. No. 14/154,093, filed Jan. 13, 2014.
U.S. Appl. No. 14/227,982 / U.S. Pat. No. 9,707,382 filed Mar. 27, 2014 / Jul. 18, 2017.
U.S. Appl. No. 14/282,615 / U.S. Pat. No. 9,713,696 filed May 20, 2014 / Jul. 25, 2017.
U.S. Appl. No. 14/712,801 / U.S. Pat. No. 9,980,815 filed May 14, 2015 / May 29, 2018.
U.S. Appl. No. 15/449,834 / U.S. Pat. No. 10,076,403 filed Mar. 3, 2017 / Sep. 18, 2018.
U.S. Appl. No. 15/492,852 / U.S. Pat. No. 10,368,981 filed Apr. 20, 2017 / Aug. 6, 2019.
U.S. Appl. No. 15/570,752 / U.S. Pat. No. 10,368,981 filed Oct. 21, 2017 / Mar. 9, 2021.
U.S. Appl. No. 15/608,948, filed May 30, 2017.
U.S. Appl. No. 15/624,314 / U.S. Pat. No. 10,357,357 filed Jun. 15, 2017 / Jul. 23, 2019.
U.S. Appl. No. 15/650,783 / U.S. Pat. No. 10,639,459 filed Jul. 14, 2017 / May 5, 2020.
U.S. Appl. No. 15/656,936 / U.S. Pat. No. 10,478,594 filed Jul. 21, 2017 / Nov. 19, 2019.
U.S. Appl. No. 15/668,622 / U.S. Pat. No. 10,463,490 filed Aug. 3, 2017 / Nov. 5, 2019.
U.S. Appl. No. 15/798,250 / U.S. Pat. No. 11,109,988 filed Oct. 30, 2017 / Sep. 7, 2021.
U.S. Appl. No. 15/988,888 / U.S. Pat. No. 10,828,151 filed May 24, 2018 / Nov. 10, 2020.
U.S. Appl. No. 16/130,978 / U.S. Pat. No. 10,251,740 filed Sep. 13, 2018 / Apr. 9, 2019.
U.S. Appl. No. 16/130,988 / U.S. Pat. No. 10,925,706 filed Sep. 13, 2018 / Feb. 23, 2021.
U.S. Appl. No. 16/205,213 / U.S. Pat. No. 10,835,394 filed Nov. 29, 2018 / Nov. 17, 2020.
U.S. Appl. No. 16/374,698, filed Apr. 3, 2019.
U.S. Appl. No. 16/395,209 / U.S. Pat. No. 11,135,054 filed Apr. 25, 2019 / Oct. 5, 2021.
U.S. Appl. No. 16/408,419 / U.S. Pat. No. 11,291,807 filed May 9, 2019 / Apr. 5, 2022.
U.S. Appl. No. 16/505,624 / U.S. Pat. No. 11,253,353 filed Jul. 8, 2019 / Feb. 22, 2022.
U.S. Appl. No. 16/672,420 / U.S. Pat. No. 11,266,501 filed Nov. 1, 2019 / Mar. 8, 2022.
U.S. Appl. No. 16/686,013, filed Nov. 15, 2019.
U.S. Appl. No. 16/866,377, filed May 4, 2020.
U.S. Appl. No. 16/875,652 / U.S. Pat. No. 10,898,698, filed May 15, 2020 / Jan. 26, 2021.
U.S. Appl. No. 16/876,640, filed May 18, 2020.
U.S. Appl. No. 16/878,228 / U.S. Pat. No. 10,912,645, filed May 19, 2020 / Feb. 9, 2021.
U.S. Appl. No. 16/963,139, filed Jul. 17, 2020.
U.S. Appl. No. 17/092,063, filed Nov. 6, 2020.
U.S. Appl. No. 17/092,081, filed Nov. 6, 2020.
U.S. Appl. No. 17/095,615 / U.S. Pat. No. 11,304,831, filed Nov. 11, 2020 / Apr. 19, 2022.
U.S. Appl. No. 17/098,251 / U.S. Pat. No. 11,234,702, filed Nov. 13, 2020 / Feb. 1, 2022.
U.S. Appl. No. 17/166,771, filed Feb. 3, 2021.
U.S. Appl. No. 17/175,549, filed Feb. 12, 2021.
U.S. Appl. No. 17/192,612, filed Mar. 4, 2021.
U.S. Appl. No. 17/465,791, filed Sep. 2, 2021.
U.S. Appl. No. 17/490,510, filed Sep. 30, 2021.
U.S. Appl. No. 17/600,079, filed Sep. 29, 2021.
U.S. Appl. No. 17/649,176, filed Jan. 27, 2022.
U.S. Appl. No. 17/649,331, filed Jan. 28, 2022.
U.S. Appl. No. 17/651,409, filed Feb. 16, 2022.
U.S. Appl. No. 17/653,551 / U.S. Pat. No. 11,382,747, filed Mar. 4, 2022 / Jul. 12, 2022.
U.S. Appl. No. 17/656,521, filed Mar. 25, 2022.
U.S. Appl. No. 17/659,312, filed Apr. 14, 2022.
U.S. Appl. No. 17/660,384, filed Apr. 22, 2022.
U.S. Appl. No. 17/805,001, filed Jun. 1, 2022.
U.S. Appl. No. 17/811,476, filed Jul. 8, 2022.
Clowes, et al., Mechanisms of Arterial Graft Healing—Rapid Transmural Capillary Ingrowth Provides a Source of Intimal Endothelium and Smooth Muscle in Porous PTFE Prostheses, Am. J. Pathol., 123(2):220-230 (May 1986).
Greitz, et al., Pulsatile Brain Movement and Associated Hydrodynamics Studied by Magnetic Resonance Phase Imaging, Diagnostic Neuroradiology, 34(5):370-380 (1992).
International Search Report & Written Opinion dated Feb. 3, 2023 in Int'l PCT Patent Appl. Serial No. PCT/IB2022/060621 (2210).
International Search Report & Written Opinion dated Mar. 29, 2023 in Int'l PCT Patent Appl. Serial No. PCT/IB2023/050743 (2410).

* cited by examiner

Immediately post shunt implantation

After healing

Immediately post shunt implantation

After healing

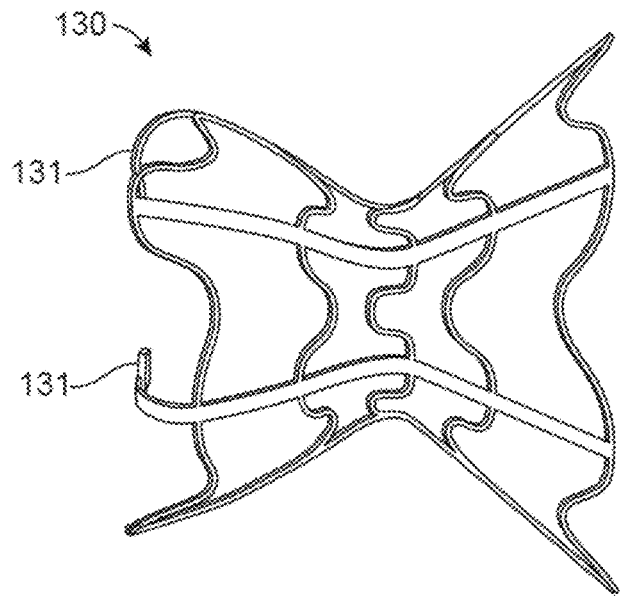
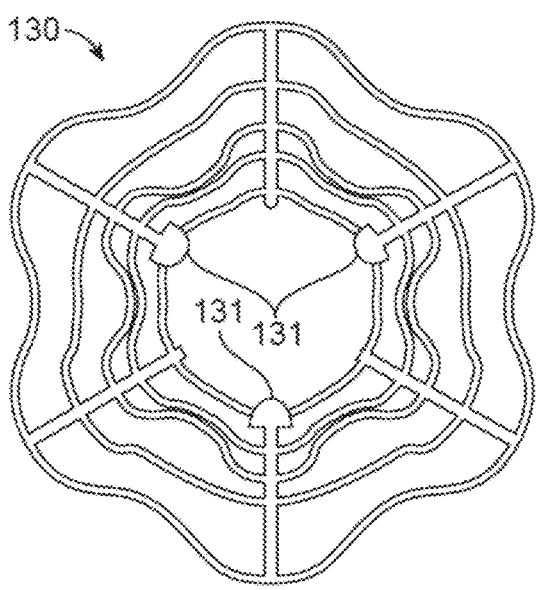
FIG. 16A  FIG. 16B
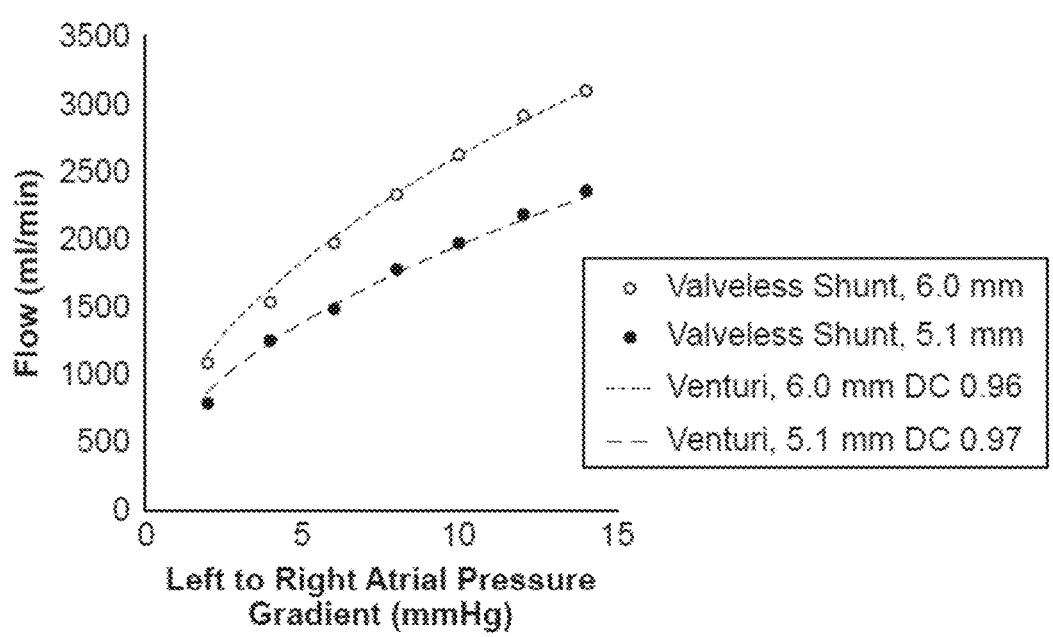
FIG. 17

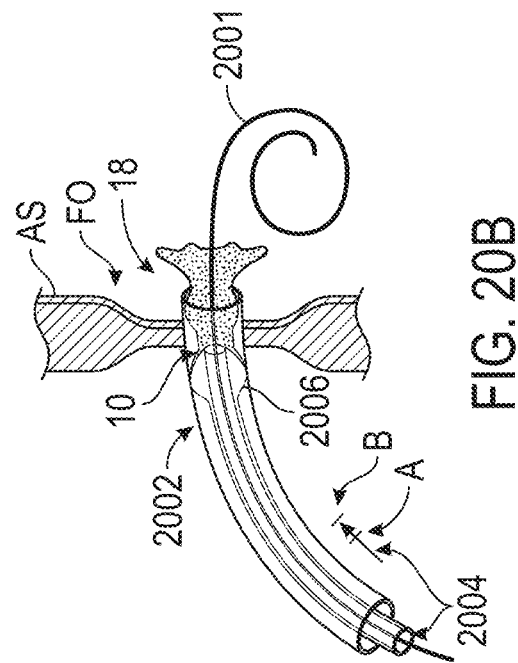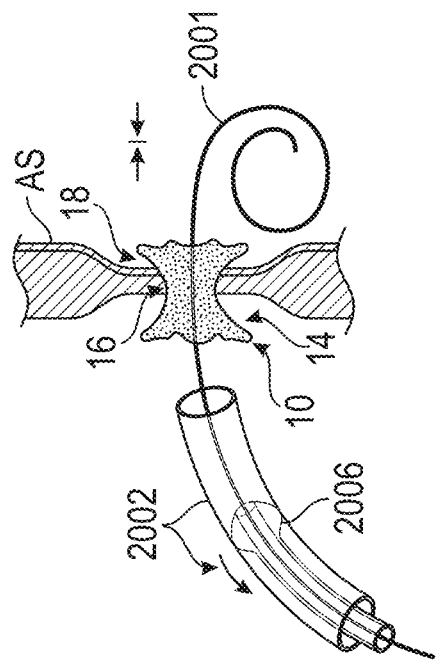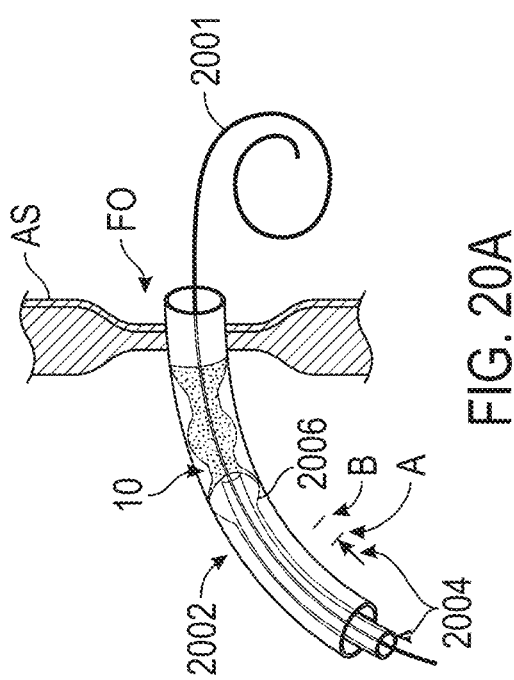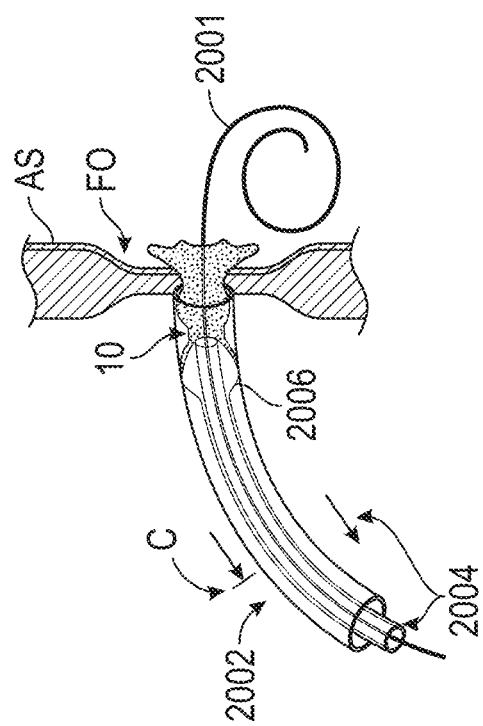

SHUNT FOR REDISTRIBUTING ATRIAL BLOOD VOLUME

CROSS-REFERENCE TO RELATED APPLICATIONS

This application is a continuation of U.S. patent application Ser. No. 17/175,549, filed Feb. 12, 2021, which is a continuation-in-part application of U.S. patent application Ser. No. 16/130,988, filed Sep. 13, 2018, now U.S. Pat. No. 10,925,706, which is a continuation application of U.S. patent application Ser. No. 15/449,834, filed Mar. 3, 2017, now U.S. Pat. No. 10,076,403, which is a continuation-in-part application of U.S. patent application Ser. No. 14/712,801, filed May 14, 2015, now U.S. Pat. No. 9,980,815, which is a divisional application of U.S. patent application Ser. No. 13/193,335, filed Jul. 28, 2011, now U.S. Pat. No. 9,034,034, which claims the benefit of U.S. Prov. patent application Ser. No 61/425,792, filed Dec. 22, 2010, and which is a continuation-in-part application of PCT/IL2010/000354, filed May 4, 2010, which claims the benefit of U.S. Prov. patent application Ser. No. 61/240,667, filed Sep. 9, 2009, and 61/175,073, filed May 4, 2009, the entire contents of each of which are incorporated by reference herein.

FIELD OF USE

This application generally relates to percutaneously placed implants and methods for redistributing blood from one cardiac chamber to another to address pathologies such as heart failure (HF), myocardial infarction (MI) and pulmonary arterial hypertension (PAH).

BACKGROUND

Heart failure is the physiological state in which cardiac output is insufficient to meet the needs of the body or to do so only at a higher filing pressure. There are many underlying causes of HF, including myocardial infarction, coronary artery disease, valvular disease, hypertension, and myocarditis. Chronic heart failure is associated with neurohormonal activation and alterations in autonomic control. Although these compensatory neurohormonal mechanisms provide valuable support for the heart under normal physiological circumstances, they also play a fundamental role in the development and subsequent progression of HF.

For example, one of the body's main compensatory mechanisms for reduced blood flow in HF is to increase the amount of salt and water retained by the kidneys. Retaining salt and water, instead of excreting it via urine, increases the volume of blood in the bloodstream and helps to maintain blood pressure. However, the larger volumes of blood also cause the heart muscle, particularly the ventricles, to become enlarged. As the heart chambers become enlarged, the wall thickness decreases and the heart's contractions weaken, causing a downward spiral in cardiac function. Another compensatory mechanism is vasoconstriction of the arterial system, which raises the blood pressure to help maintain adequate perfusion, thus increasing the load that the heart must pump against.

In low ejection fraction (EF) heart failure, high pressures in the heart result from the body's attempt to maintain the high pressures needed for adequate peripheral perfusion. However, as the heart weakens as a result of such high pressures, the disorder becomes exacerbated. Pressure in the left atrium may exceed 25 mmHg, at which stage, fluids from the blood flowing through the pulmonary circulatory system transudate or flow out of the pulmonary capillaries into the pulmonary interstitial spaces and into the alveoli, causing lung congestion and if untreated the syndrome of acute pulmonary edema and death.

Table 1 lists typical ranges of right atrial pressure (RAP), right ventricular pressure (RVP), left atrial pressure (LAP), left ventricular pressure (LVP), cardiac output (CO), and stroke volume (SV) for a normal heart and for a heart suffering from HF. In a normal heart beating at around 70 beats/minute, the stroke volume needed to maintain normal cardiac output is about 60 to 100 milliliters. When the preload, after-load, and contractility of the heart are normal, the pressures required to achieve normal cardiac output are listed in Table 1. In a heart suffering from HF, the hemodynamic parameters change (as shown in Table 1) to maintain peripheral perfusion.

TABLE 1

| Parameter | Normal Range | HF Range |
|---|---|---|
| RAP (mmHg) | 2-6 | 6-20 |
| RVSP (mmHg) | 15-25 | 20-80 |
| LAP (mmHg) | 6-12 | 15-50 |
| LVEDP (mmHg) | 6-12 | 15-50 |
| CO (liters/minute) | 4-8 | 2-6 |
| SV (milliliters/beat) | 60-100 | 30-80 |

HF is generally classified as either systolic heart failure (SHF) or diastolic heart failure (DHF). In SHF, the pumping action of the heart is reduced or weakened. A common clinical measurement is the ejection fraction, which is a function of the blood ejected out of the left ventricle (stroke volume) divided by the maximum volume in the left ventricle at the end of diastole or relaxation phase. A normal ejection fraction is greater than 50%. Systolic heart failure generally causes a decreased ejection fraction of less than 40%. Such patients have heart failure with reduced ejection fraction (HFrEF). A patient with HFrEF may usually have a larger left ventricle because of a phenomenon called "cardiac remodeling" that occurs secondarily to the higher ventricular pressures.

In DHF, the heart generally contracts normally, with a normal ejection fraction, but is stiffer, or less compliant, than a healthy heart would be when relaxing and filling with blood. Such patients are said to have heart failure with preserved ejection fraction (HFpEF). This stiffness may impede blood from filling the heart and produce backup into the lungs, which may result in pulmonary venous hypertension and lung edema. HFpEF is more common in patients older than 75 years, especially in women with high blood pressure.

Both variants of HF have been treated using pharmacological approaches, which typically involve the use of vasodilators for reducing the workload of the heart by reducing systemic vascular resistance, as well as diuretics, which inhibit fluid accumulation and edema formation, and reduce cardiac filling pressure. No pharmacological therapies have been shown to improve morbidity or mortality in HFpEF whereas several classes of drugs have made an important impact on the management of patients with HFrEF, including renin-angiotensin antagonists, beta blockers, and mineralocorticoid antagonists. Nonetheless, in general, HF remains a progressive disease and most patients have deteriorating cardiac function and symptoms over time. In the U.S., there are over 1 million hospitalizations annually for acutely worsening HF and mortality is higher than for most forms of cancer.

In more severe cases of HFrEF, assist devices such as mechanical pumps are used to reduce the load on the heart by performing all or part of the pumping function normally done by the heart. Chronic left ventricular assist devices (LVAD), and cardiac transplantation, often are used as measures of last resort. However, such assist devices typically are intended to improve the pumping capacity of the heart, to increase cardiac output to levels compatible with normal life, and to sustain the patient until a donor heart for transplantation becomes available. Such mechanical devices enable propulsion of significant volumes of blood (liters/min), but are limited by a need for a power supply, relatively large pumps, and pose a risk of hemolysis, thrombus formation, and infection. Temporary assist devices, intra-aortic balloons, and pacing devices have also been used.

Various devices have been developed using stents to modify blood pressure and flow within a given vessel, or between chambers of the heart. For example, U.S. Pat. No. 6,120,534 to Ruiz is directed to an endoluminal stent for regulating the flow of fluids through a body vessel or organ, for example, for regulating blood flow through the pulmonary artery to treat congenital heart defects. The stent may include an expandable mesh having lobed or conical portions joined by a constricted region, which limits flow through the stent. The mesh may comprise longitudinal struts connected by transverse sinusoidal or serpentine connecting members. Ruiz is silent on the treatment of HF or the reduction of left atrial pressure.

U.S. Pat. No. 6,468,303 to Amplatz et al. describes a collapsible medical device and associated method for shunting selected organs and vessels. Amplatz describes that the device may be suitable to shunt a septal defect of a patient's heart, for example, by creating a shunt in the atrial septum of a neonate with hypoplastic left heart syndrome (HLHS). That patent also describes that increasing mixing of pulmonary and systemic venous blood improves oxygen saturation, and that the shunt may later be closed with an occluding device. Amplatz is silent on the treatment of HF or the reduction of left atrial pressure, as well as on means for regulating the rate of blood flow through the device.

Implantable interatrial shunt devices have been successfully used in patients with severe symptomatic heart failure. By diverting or shunting blood from the left atrium (LA) to the right atrium (RA), the pressure in the left atrium is lowered or prevented from elevating as high as it would otherwise (left atrial decompression). Such an accomplishment would be expected to prevent, relieve, or limit the symptoms, signs, and syndromes associated of pulmonary congestion. These include severe shortness of breath, pulmonary edema, hypoxia, the need for acute hospitalization, mechanical ventilation, and death.

Shunt flow is generally governed by the pressure gradient between the atria and the fluid mechanical properties of the shunt device. The latter are typically affected by the shunt's geometry and material composition. For example, the general flow properties of similar shunt designs have been shown to be related to the mean interatrial pressure gradient and the effective orifice diameter.

Percutaneous implantation of interatrial shunts generally requires transseptal catheterization immediately preceding shunt device insertion. The transseptal catheterization system is placed from an entrance site in the femoral vein, across the interatrial septum in the region of fossa ovalis (FO), which is the central and thinnest region of the interatrial septum. The FO in adults is typically 15-20 mm in its major axis dimension and ≤3 mm in thickness, but in certain circumstances may be up to 10 mm thick. LA chamber access may be achieved using a host of different techniques familiar to those skilled in the art, including but not limited to: needle puncture, stylet puncture, screw needle puncture, and radiofrequency ablation. The passageway between the two atria is dilated to facilitate passage of a shunt device having a desired orifice size. Dilation generally is accomplished by advancing a tapered sheath/dilator catheter system or inflation of an angioplasty type balloon across the FO. This is the same general location where a congenital secundum atrial septal defect (ASD) would be located.

U.S. Patent Publication No. 2005/0165344 to Dobak, III describes apparatus for treating heart failure that includes a tubular conduit having a emboli filter or valve, the device configured to be positioned in an opening in the atrial septum of the heart to allow flow from the left atrium into the right atrium. Dobak discloses that shunting of blood may reduce left atrial pressures, thereby preventing pulmonary edema and progressive left ventricular dysfunction, and reducing LVEDP. Dobak describes that the device may include deployable retention struts, such as metallic arms that exert a slight force on the atrial septum on both sides and pinch or clamp the device to the septum.

Two types of percutaneously implantable shunts have been described in the medical and patent literature. In short-term, small-size clinical trials, both types have been shown to be associated with improvements in symptoms, quality of life measurements, and exercise capacity. Both shunts also have observed and theoretical drawbacks, which may limit their effectiveness and use.

The first type of shunt is henceforth referred to as an orifice-plate mesh shunt. Orifice-plate mesh shunts comprise a metallic mesh that wraps around both sides of the septum with a hole in the center and anatomically mimics the location and geometrical characteristics of a small congenital secundum ASD. The shunt geometry generally resembles a thin plate with a hole in it. In most embodiments, the "plate" comprises both mesh material and atrial septal tissue encased by the mesh. One example of such devices, designed by Corvia Medical, Inc., Tewksbury MA, consists of a self-expanding nitinol mesh that forms a pair of disc-like flanges with an open orifice in the center. The maximal diameter of the discs is 19.4 mm and the orifice diameter is 8 mm. Each disc flange has multiple truss-like legs that deploy into a preset configuration that wraps around the LA and RA sides of the interatrial septum and applies a clamping force to the tissue.

Another example of such a mesh type device, developed by Occlutech International AB, Helsingborg, Sweden, resembles a dual-disc occluder used for closing congenital secundum ASDs, which additionally includes a short open barrel orifice in the center that connects the two discs.

A major benefit of the foregoing orifice-plate mesh shunts over other shunt designs is simplicity of manufacture. Although relatively simple in theory and construction, orifice-plate mesh type shunts have several important drawbacks that are expected to reduce their overall potential for clinical safety and effectiveness.

A first drawback of orifice-plate devices is the susceptibility to narrow or close during the post-implantation healing period. For example, neoendocardial tissue ingrowth, referred to as pannus, grows from the underlining tissue to cover the mesh and narrow or partially occlude the shunt orifice. During the period following implantation, local trauma caused by crossing and dilating the FO, plus the chronic effects of continuous pressure applied by the mesh material on the septal tissue, provoke a localized healing response. This response entails activation of an inflammatory process, attracting lymphocytes and macrophages to the area of tissue injury. These inflammatory cells in turn release a variety of cytokines that signal fibroblasts and smooth-muscle cells from the wound margins to dedifferentiate, migrate, proliferate and encapsulate affected portions of the implanted device. The fibroblasts and smooth muscle cells then secrete extracellular matrix material composed of collagen and proteoglycans, which extracellular matrix forms the bulk of the pannus. The duration of this healing phase in humans is typically up to 6-9 months, but may be longer if there is a chronic source for tissue injury such as device compression or erosion of adjacent tissue. Eventually this pannus is covered with neoendothelial cells, causing the pannus growth to stop or stabilize. In the long term, the collagen of the pannus remodels, but generally retains its space occupying properties. Such tissue ingrowth typically spreads over the surfaces of the implant's struts, mesh, or discs, and may substantially narrow the orifice lumen or even entirely occlude the shunt. Narrowing or occlusion of the shunt prevents LA decompression and limits any positive effect for the patient.

The degree of luminal narrowing may be quite variable between patients due to differences in the severity of local injury—the more injury, the more exaggerated the pannus formation. Also, variability results from differences in host wound healing responses. For example, the amount and character of extracellular matrix may affect the duration of healing and amount of material deposited. Thus, for an orifice-plate mesh shunt, the eventual orifice lumen size will be highly variable. These processes will be familiar to one skill in the art as it is generally analogous to the type of late lumen loss that occurs in arteries when bare metal stents are used to treat atherosclerotic stenosis.

In a trial described in the publication, "A Transcatheter Intracardiac Shunt Device for Heart Failure with Preserved Ejection Fraction (REDUCE LAP-HF): A Multicentre, Open-label, Single-arm, Phase 1 Trial" by Hasenfuss, et al., 14 of 64 patients implanted with an orifice-plate mesh shunt device had no demonstrable flow across the shunt on transthoracic echocardiographic Doppler imaging at 6 months after implantation. It has not reported whether the shunts were occluded or if the imaging study was simply too technically difficult to tell for certain. Although additional interventional cardiology procedures may be undertaken to restore lost luminal patency, such procedures may pose unacceptable risks, including death and stroke from embolization of the orifice-clogging material.

A second drawback of an orifice-plate mesh shunt is the potential for paradoxical embolization. Paradoxical embolization refers to thromboembolism originating in the venous vasculature (venous thromboembolism or VTE), such that an embolus traverses right-to-left through a cardiac shunt into the systemic arterial circulation. The most severe complication of paradoxical embolization occurs when an embolus lodges in the cerebral circulation with resulting cerebral infarction (stroke). Similarly, if a paradoxical embolus enters the coronary arterial circulation, myocardial infarction (MI) may ensue. Other embolic syndromes result from embolization to the mesenteric, renal, and peripheral arteries supplying the limbs. These may cause respectively, ischemic bowel syndrome, hematuria with worsening renal function, and gangrene requiring amputation.

Most frequently, VTE in adults is the consequence of in situ thrombosis in the deep veins (deep venous thrombosis or DVT) of the lower extremities or pelvis. For the most part, clinically relevant venous emboli develop in the popliteal veins or more proximally in larger veins of the upper thigh or pelvis. In patients with DVT involving the popliteal vein, the venous diameter averaged 11.4 mm (range from 6.2 mm to 20.1 mm). Often, emboli are described as having the form of a cast of the vein's lumen with a width equal to the diameter of the vein of origin. These thrombi also tend to be elongated, corresponding to the length of the occluded venous segment.

The risk factors associated with thromboembolic disease include a variety of anatomic, physiological, rheological variables and disease states. Heart failure is a well-recognized risk factor for DVT and VTE, especially in patients with reduced left ventricular systolic function. About 3% of deaths in heart failure patients are due to VTE, usually associated with pulmonary embolism. Patients with transvenous endocardial pacing leads and an intracardiac shunt have a 3-fold increased risk of systemic thromboembolism, suggesting that paradoxical embolism is a contributing underlying cause. There is evidence that the risk of paradoxical embolism is directly related to the orifice size of naturally occurring atrial level shunts such as ASD and patent foramen ovale (PFO). The presence of an atrial septal aneurysm is an additional risk factor. For example, as described in the publication "Transcatheter Amplatzer Device Closure of Atrial Septal Defect and Patent Foramen Ovale in Patients with Presumed Paradoxical Embolism" by Khositsth, et al., in a series of 103 adult patients with paradoxical embolization, an ASD was present in 12%, whereas PFO was present in 81%. In patients with clinically significant ASD referred for closure, the incidence of paradoxical embolus has been reported to be up to 14%.

It has been asserted that in order for VTE to enter the systemic circulation, the prevailing LA to RA pressure gradient must be temporarily reduced, eliminated or reversed so that blood will either flow slowly across the shunt, cease to flow across the shunt or flow retrograde across the shunt. Echo/Doppler imaging studies often reveal some amount of shunting in both directions (bi-directional shunting) in patients with congenital ASD, even when LA to RA flow predominates. Bidirectional shunting may be best demonstrated when a subject performs a Valsalva maneuver (straining caused by exhalation against a closed glottis). Valsalva increases intrathoracic pressure, which causes the RA and LA pressures to equalize after several seconds and then for the RA pressure to transiently exceed LA pressure on exhalation. Intermittent bidirectional flow also may be observed at rest when the interatrial pressure gradient is low, or intermittently during the cardiac cycle when LA contraction is delayed compared to RA contraction (interatrial conduction delay). This is seen especially when the atria are enlarged or diseased, such as in heart failure. In this setting, interatrial electrical conduction delay results in retardation of LA contraction. Bidirectional shunting can also be seen transiently during inspiration, when venous return to the RA is increased, during coughing, with abdominal compression, during forced exhalation, or in the presence of severe tricuspid valve regurgitation. Chronically increased pulmonary arterial pressure, as seen in severe pulmonary hypertension, whether primary or secondary to chronic lung disease, recurrent pulmonary embolism, or due to chronic right ventricular volume overload, has been associated with chronic and more severe RA to LA shunting.

Additional phenomena associated with RA to LA shunting are diminished pulmonary blood flow and decreased arterial oxygen saturation due to systemic venous admixing. When these findings are also transient, they are generally well tolerated. Thus, prevention of significant or larger paradoxical emboli is the primary concern rather than preventing reverse shunting per se. As the consequences of paradoxical embolization can be catastrophic, it is desirable particularly in high-risk patients, that an implantable shunt be equipped with mechanism(s) that limit or minimize the chances of paradoxical embolization or minimize the chances of transporting large emboli.

From these data, it seems reasonable to expect that an orifice-plate mesh shunt, by virtue of its anatomic similarities with congenital secundum ASD, would have a similar risk of paradoxical embolization. It is easily understandable that a thin plate-orifice mesh type of artificial shunt might be more susceptible to paradoxical embolization than other types of shunts with longer orifice geometries, e.g., a nozzle. For any given quanta of RA volume (blood or thrombus), the statistical likelihood of traversing retrograde across the shunt and into the LA would be expected to be a complex function of the duration of pressure gradient reversal, flow patterns in the RA, shunt tunnel distance affecting the length of the flow velocity streamlines, and flow velocity and orifice or lumen size.

A third drawback of an orifice-plate mesh shunt is that percutaneous removal from the shunt body is only possible at the time of implantation. Should the shunt become a nidus for infection, develop fatigue or corrosion fractures of its metallic framework, or erode or otherwise impinge on other vital cardiac structures, it cannot be removed by percutaneous retrieval/removal techniques. This is because the shunt, with its large "footprint" on the interatrial septum, is encased in pannus tissue. Attempts at percutaneous removal may result in tearing of the septum, pericardial tamponade, and device embolization into the systemic circulation, resulting in death or the need for emergency surgery. Safe removal would require performing open heart surgery. This entails that the heart be bypassed using an extracorporeal membrane pump oxygenator (cardiopulmonary bypass), so the heart can be opened, the shunt removed, and the septum repaired. Performing such surgical procedures in patients with already established severe heart failure, including its frequently associated co-morbid conditions such as peripheral, cerebrovascular, and coronary artery disease, renal dysfunction, and diabetes, would be expected to have substantial risks for mortality or severe morbidity.

A fourth drawback of an orifice-plate mesh type of shunt is that its geometry renders it relatively inefficient in supporting high flow. For any given pressure gradient across the shunt, the geometry of an orifice plate requires a larger orifice because it has a reduced effective orifice size compared with other geometries, such as a venturi-shaped lumen, or a conical shaped nozzle. This is because with an office-plate, there are more energy losses associated with eddy currents at the edges of the plate. Orifice-plate geometries may be categorized as having a relatively low discharge coefficient, which is a dimensionless fluid-mechanical parameter that relates flow to actual orifice size. For practical purposes, the discharge coefficient is the ratio of areas of the exiting jet vena contracta, which is the narrowest portion of the jet, compared to the shunt orifice. For example, the coefficient of discharge for orifice plates placed in pipes tends to be approximately 0.6, but rarely exceeds 0.65. The discharge coefficient is affected by the orifice and chamber dimensions, the pressure gradient, and the viscosity of blood and/or the Reynolds number of the specific flow condition. This differs from the more efficient passage of flow through a classic venturi type of narrowing, where the discharge coefficient usually exceeds 0.9 and is typically in the range of 0.94 to 0.98. The result is that, in comparison with more efficient shunt lumen geometries, an orifice-plate mesh shunt requires a larger orifice diameter to accommodate the same amount of flow for any given pressure differential across the shunt.

A fifth drawback of an orifice-plate mesh shunt is that it occupies a large area or footprint on the interatrial septum. The flanges of the device that anchor the shunt typically occupy the entire area of the fossa ovalis and may overlap adjoining muscular portions of the interatrial septum. These flanges exert persistent pressure on the septum, causing injuring and stimulating an exaggerated healing response as described above. Also, the rigidity of the mesh may interfere with the normal motion of the muscular septum. The flanges additionally may impinge on adjacent cardiac structures such as the roof of the left atrium, the ostia of the pulmonary veins, and the aorta root and sinuses of Valsalva, where due to chronic rubbing contact or sandwiching compressive forces, they may erode into these vital structures. Such erosion has been associated with severe complications including cardiac tamponade and death. For example, the similarly sized Amplatzer ASD disc occlusion device described above has been occasionally associated with erosion into adjoining tissues with resulting catastrophic outcomes.

Additional issues associated with placing relatively large devices with complex three-dimensional geometries are potential difficulties in positioning the shunts accurately in the FO, obtaining sufficient tissue anchoring to prevent migration, and having devices conform to irregularities of the cardiac anatomy. For example, in a report of attempted implantation of orifice-plate mesh shunts in 66 patients in the above cited publication authored by Hasenfuss, et al., device placement was not possible in two patients. And of the 64 implanted patients, the device had to be removed and re-implanted in another 3 patients due to misplacement, migration, or embolization of the first attempted implant.

Finally, the large footprint on the atrial septum may hinder or render impossible performing other interventional procedures that require transseptal access. The large flange diameter and small mesh pore sizes generally make catheter crossing of the atrial septum possible only through the central shunt orifice itself. Transseptal procedures using small diameter catheters, such as atrial fibrillation RF ablation, may be conducted through the orifice-plate lumen only if it is not obstructed by pannus and the orifice location permits entry into all four pulmonary veins. Other structural heart disease procedures that have large diameter delivery systems and/or require crossing the FO in specific locations may encounter difficulties or simply not be possible. These procedures include left atrial appendage occlusion, mitral valve edge-to-edge ("MitraClip") repair, and transvascular mitral valve replacement. For example, placing of a Mitra-Clip optimally requires crossing the FO in its superior-posterior quadrant. The guiding catheter has a tip inner diameter of 7.7 mm (23 Fr). Similar transseptal access is needed to perform reconstructive mitral annuloplasty with the Cardioband device marketed by Valtech. In these cases, the only alternatives might be higher risk therapeutic approaches involving trans-left ventricular apical access or open heart surgery.

The second type of shunt is referred to as a valved unidirectional shunt. These shunts attempt to overcome some of the drawbacks of orifice-plate devices. For example, valved unidirectional shunts have embodiments containing a one-way or check-valve to limit reverse shunting and paradoxical embolization. Some of the valve configurations are designed to open when the LA-RA pressure gradient exceeds a predefined threshold. Other valve configurations close only when the RA pressure exceeds LA pressure (reversed gradient).

U.S. Pat. No. 9,034,034 to Nitzan, the entire contents of which are incorporated by reference herein, solves many of the drawbacks of plate-like orifice mesh shunts describe above. An embodiment of the Nitzan-type shunt comprises an hourglass or diabolo outer shape, having a small FO footprint minimizing septal injury, which is expected to minimize pannus growth and obliteration of the shunt lumen. Its one-way valve also is designed to reduce the potential for reverse shunting and paradoxical embolization. The relatively small footprint of the shunt in contact with the septum and encapsulated collapsible nitinol frame is designed to facilitate percutaneous extraction from the septum and retrieval from the body using a standard goose-neck snare and large-bore sheath, thus making the device more easily retrieved. The venturi tube-like inner lumen of the diabolo shape provides better bulk flow characteristics, permitting a smaller orifice for the same amount of flow compared to orifice plate shunts. And finally, the small footprint on the FO and the hourglass shape are designed to facilitate accurate placement and retention during implantation. This geometry also minimizes interference with normal motion of the interatrial septum, and the small footprint provides space surrounding the shunt for other potential interventional procedures that require transseptal catheterization.

One embodiment of the Nitzan design, manufactured by V-Wave, Ltd (Caesarea, Israel), designed to support unidirectional left-to-right flow, comprises a self-expanding frame constructed from a laser-cut nitinol tube. The frame includes five sinusoidal circumferential struts interconnected by six longitudinal bars. The frame is heat-set so that it has an asymmetrical hourglass shape or a diabolo shape. The shunt is deployed so that the neck (5.3 mm outer diameter) is placed across the FO and secured in place by its external surface geometry. The shunt's widest portion has a conical shape with an approximately 14.3 mm outer diameter at the LA end of the shunt, which serves as an "entry" port on the distal end of the entry funnel. The entry funnel is deployed in the left atrium, and registers the neck of the shunt to the region of the FO. A second, slightly narrower bell-shaped portion forms the exit portion of the shunt, which expands to a maximum outer diameter of 11.4 mm at the RA end of the shunt. The shunt does not require flanges, discs, or tissue anchors to secure it in place. Septal retention is achieved without applying persistent pressure, tension or rubbing contact on the tissue adjoining the device neck.

The V-Wave shunt has a single inner lumen where flow is entrained into the entry funnel in the LA and passes through the constricted neck having a 5.1 mm inner diameter, which resembles a venturi-type orifice, and then exits through a bioprosthetic valve positioned near the RA end of the shunt. The entry funnel and the central neck region are encapsulated with expanded polytetrafluoroethylene ("ePTFE") to form a skirt or cover over the frame. The skirt is designed to facilitate laminar flow and limit pannus ingrowth during device healing. The exit bell-shaped portion contains three, glutaraldehyde-fixed, porcine pericardial leaflets sutured to the frame at the right atrial extent of the ePTFE encapsulation. The leaflets are designed to create a smooth exit channel and remain in the open position, closing only when the RA pressure exceeds LA pressure by 1-2 mmHg, thus preventing reverse right-to-left shunting.

For deployment, the V-Wave shunt is compressed in a loading tube where it is attached to a triple-latch cable delivery catheter. The loading tube is inserted into a 14F delivery sheath that has been previously placed after a trans septal catheterization from the right femoral vein across the FO. The shunt then is advanced through the sheath until the entry funnel has been deployed in the LA. The entire system is withdrawn as a unit until the LA funnel is in contact with the left side of the FO. The delivery catheter latches are unhooked from the shunt, the delivery catheter withdrawn so the right atrial side of the shunt is held only by its radial force against the delivery sheath. Then the delivery sheath is withdrawn, thereby deploying the exit bell-shaped portion of the shunt on the RA side of the FO. Device placement may be guided and confirmed by fluoroscopy and echocardiography, e.g., intracardiac echo or transesophageal echo.

U.S. Patent Publication Nos. 2017/0348100 and 2020/0188091 to Lane describe systems and methods for deploying a self-expanding cardiac prosthetic device, e.g., a mitral valve prosthesis. However, the deployment procedures described therein require maintaining the position of the delivery catheter, e.g., a mandrel/tether system, after the prosthetic device is unsheathed, rather than permitting the local anatomy to exert a counterforce to position the valve during unsheathing.

Pre-clinical testing on the V-Wave shunt was performed in an established juvenile ovine (sheep) model that created an ischemic cardiomyopathy form of heart failure. The sheep were pre-treated with sequential coronary artery microembolization as described in the publication, "Chronic Heart Failure Induced by Multiple Sequential Coronary Microembolization in Sheep" by Schmitto et al. After several weeks, the sheep manifested evidence of severe left ventricular systolic dysfunction and develop elevated LV, LA, and pulmonary artery pressures. In a 12-week survival study, this V-Wave shunt was associated with significant improvements in LA pressure and left ventricular ejection fraction. All manifestations of worsening heart failure were improved and in some cases reversed with interatrial shunting. Concurrent control animals with established heart failure, but were not implanted with the V-Wave shunt, demonstrated progressive worsening of LV ejection fraction, and intracardiac/pulmonary pressure during 3-month follow-up. The physiological improvements in shunted animals were substantial even though the shunt volume was assessed to be small. The pulmonary blood flow/systemic blood flow ratio (Qp/Qs) was between 1.1 to 1.2, as measured by oximetry, which is consistent with a very small shunt. Naturally occurring ASDs, with a Qp/Qs less than 1.5, are generally left untreated as they are well tolerated for decades by the compliant right heart and pulmonary vasculature, without evidence of worsening right ventricular failure despite mild chronic volume overload. This was confirmed in the sheep model where RA and pulmonary artery pressures decreased to baseline levels with shunting, but progressively worsened in the control animals.

A total of 38 patients were implanted with the V-Wave hourglass-shaped shunt having valve leaflets in two similar feasibility studies. The baseline characteristics of the combined study populations are summarized in Table 1 below.

TABLE 1

Baseline characteristics of 38 patients implanted with valved hourglass-shaped shunt device

| | |
|---|---|
| Age, years | 66 ± 9 |
| Male gender, % | 92 |
| Body mass index, kg/m2 | 30 ± 6 |

TABLE 1-continued

Baseline characteristics of 38 patients implanted
with valved hourglass-shaped shunt device

| | |
|---|---|
| NYHA class, median | III (97%), IV (3%) |
| Ischemic Cardiomyopathy, % | 76 |
| DM/HTN/AFIB, % | 68/84/53 |
| ACEi-ARB/BB/MRA/DIUR, % | 78/100/75/94 |
| CRT-D or ICD/CRT-D or CRT-P, % | 74/39 |
| NT-proBNP, pg/ml | 2640 ± 2301 |
| eGFR, mL · min−1 · 1.73 m−2 | 54 ± 20 |
| 6MWT, m | 282 ± 114 |
| PCWP, mmHg | 20 ± 6 |
| RAP, mmHg | 8 ± 4 |
| PAP mean, mmHg | 30 ± 7 |
| CI, L · min−1 · m−2 | 2.1 ± 0.5 |
| PVR, mmHg/L · min−1 | 2.9 ± 1.4 |
| LVEF (HFrEF, n = 30), % | 26 ± 7 |
| LVEF (HFpEF, n = 8), % | 50 ± 9 |

NYHA = New York Heart Association heart failure classification;
DM = diabetes mellitus;
HTN = hypertension;
AFIB = atrial fibrillation;
ACEi-ARB = receiving angiotensin converting enzyme inhibitor or angiotensin receptor blocker;
BB = receiving beta blocker;
MRA = receiving mineralocorticoid antagonist;
DIUR = receiving loop diuretic;
CRT-D = implanted with combination cardiac resynchronization therapy pacemaker with ICD;
ICD = implantable cardioverter/defibrillator;
CRT-P = implanted with cardiac resynchronization therapy pacemaker without combination ICD;
NT-proBNP = N-terminal pro b-type natriuretic peptide;
eGFR = estimated glomerular filtration rate;
6MWT = 6 minute walk test distance;
PCWP = pulmonary capillary wedge pressure;
RAP = right atrial pressure;
PAP = pulmonary artery pressure;
CI = cardiac index;
PVR = pulmonary vascular resistance;
LVEF = left ventricular ejection fraction;
HFrEF = heart failure with reduced ejection fraction;
HFpEF = heart failure with preserved ejection fraction.
These parameters and abbreviations are well known to one skilled in the art.

All patients had New York Heart Association (NYHA) Class III or ambulatory Class IV heart failure symptoms at the time of study enrollment. Patients with either reduced or preserved left ventricular ejection fraction were included. There was a high frequency of co-morbidities known to be associated with a poorer prognosis including coronary artery disease, diabetes mellitus, atrial fibrillation, and chronic kidney dysfunction. All patients received appropriate guideline-driven medical and device therapies prior to study enrollment. Patients had evidence of elevated levels of natriuretic peptides, reduced exercise capacity, elevated intra-cardiac and pulmonary artery pressures, increased pulmonary vascular resistance, and reduced cardiac output. These factors have also been associated with poor outcomes. Patients were excluded if they had severe right ventricular dysfunction or severe pulmonary hypertension.

Implantation of the V-Wave shunt was successful in all 38 patients and no device replacements were performed. Shunts remained implanted in the atrial septum without dislodgements, migrations or apparent interference with normal septal motion on fluoroscopic or echocardiographic imaging. No shunts have required removal or replacement for infection or strut fracture. Follow-up imaging studies show that there are adjacent locations on the FO, that are available and amenable for performing transseptal procedures to treat other cardiac conditions, including, for example, atrial fibrillation ablation, left atrial appendage occlusion, and mitral valve repair. The valve apparatus, when functioning normally, has been shown to effectively prevent reverse (right-to-left) shunting. Echocardiographic contrast and Doppler studies during rest or Valsalva maneuver show that there is no reverse shunting in the early months after human implantation. Furthermore, no thromboembolic clinical events, including paradoxical embolization, have been observed during the first year of follow-up.

Shunt patency is defined as LA to RA flow through the shunt as observed during transesophageal echo/Doppler study. At 3-months after implantation of the V-Wave shunts, patency was confirmed in all patients. The pulmonary to systemic flow ratio (Qp/Qs), as measured by echocardiography, increased from 1.04±0.22 at baseline to 1.18±0.16 shortly after implantation (p<0.03). In the subgroup of 30 patients with HFrEF presented by Dr. William Abraham, MD at TCT 2016 in Washington DC, there were statistically significant (p<0.05) improvements in clinician-assessed symptoms, patient assessed quality-of-life scores, and exercise capacity as measured by a 6-minute hall walk testing at 3, 6, and 12 months following implantation There was no deterioration in natriuretic hormone levels, echocardiographic, or hemodynamic parameters. Most importantly, the annualized (Poisson) heart failure hospitalization rate with shunting (0.17 heart failure hospitalization per patient year), was substantially reduced in comparison to a well matched historical control groups (CHAMPION trial Control and Treatment groups, 0.90 and 0.67 heart failure hospitalization per patient year, respectively). These data provide adequate proof-of-concept that interatrial shunting is of benefit to patients with severe symptomatic heart failure. Moreover, these data strongly support moving forward with larger-scale clinical trials including randomized clinical trials.

Notwithstanding the initial success observed in the foregoing trial, device occlusion, e.g., shunts having undetectable LA to RA flow, was observed in some valved interatrial shunt devices after long-term implantation, e.g., by 1 year. Further, shunts may develop bidirectional shunting that was not present early on. Bidirectional shunting is indicative of an incompetent valve, e.g., a valve where one or more leaflets do not fully coapt during closure, resulting in an open channel for reversed flow, and depending on the severity of the incompetence, may create a potential path for paradoxical embolus to traverse from the RA to LA.

To assess the effective orifice size of valved shunts over time, transesophageal echo/Doppler measurements of the diameter of the vena contracta, measured on the left-to-right flow jets through the shunt, were found to be consistent with progressive shunt narrowing. The vena contracta diameter monotonically decreased with time after implantation from 4.0±1.1 mm just after implantation, to 3.6±1.0 mm at 3 months, and 2.7±1.4 mm at 6-12 months (p<0.01). This equates, on average, to shunts losing more than half of their orifice area by 12 months. Moreover, some of the left-to-right jets appeared to be exiting the shunt at an angle substantially different from the long axis of the shunt body. This skewing of the jet is consistent with material inside the shunt such as a valve leaflet with impaired mobility, which diverts the direction of the jet. This observation gives rise to concern about a decrease in the clinical effectiveness of the shunts over time Clinical effectiveness also may be measured by the rate of hospitalization for worsening heart failure. In the 38 patients, during the first 6 months after implantation of the V-Wave shunt, the hospitalization rate was 0.16 per patient year, which increased to 0.40 per patient year between months 6-12. These data suggest there may be a loss of shunting benefit consistent with the time course associated with shunt narrowing or occlusion.

There are several possible mechanisms working alone or in combination that could explain these observations.

The least likely cause of shunt occlusion is collapse of the shunt due to external forces applied by the septum. For example, it is possible that contraction of pannus tissue formed during the later stages of healing (remodeling) could result in extrinsic compression of the shunt. However, there is no evidence to support this scenario based on multiple observations of frame geometry seen during pre-clinical studies and during follow-up transesophageal echocardiography (TEE), CT, or fluoroscopic imaging in humans. In all cases, the observed shunt frame has not been observed to be extrinsically compressed or in any other way narrowed, deformed, or fractured.

Another possible mechanism is in situ thrombosis of the shunt. However, all patients were treated with monitored anticoagulation for the first three months, or indefinitely if there were other indications for chronic anticoagulation, which was most commonly required in patients with a history of atrial fibrillation. Subjects were also treated simultaneously with low-dose aspirin, which was continued indefinitely. Having experience with prosthetic cardiac valves as a predicate, valve thrombosis would have been expected to be seen earlier, typically within 30-45 days after implantation, especially in patients with a history of subtherapeutic anticoagulation therapy.

In the 38 patients implanted with the V-Wave valved hourglass-shaped shunt described above, no thrombi were detected on 121 consecutive post-implantation echocardiograms. These studies systematically looked for intracardiac or device thrombus by an independent Echocardiographic Core Laboratory at time points including one day after implantation, and at 1, 3, 6, and 12 months after implantation. None of the patients presented with stroke or other clinical manifestations of thromboembolic events. Of 9 patients with suspected shunt occlusion or incompetent valves, most were taking therapeutic doses of anticoagulants (warfarin or New Oral Anticoagulant agents) at the time the shunt anomaly was discovered. Another reason that thrombosis is unlikely is the observation of progressive vena contracta narrowing over a time course of 6 months or more. Thrombosis would be expected to result in sudden lumen loss, and not progress slowly over a period of months.

A third potential cause of occlusion is neoendocardial tissue overgrowth or pannus formation that narrows the lumen at the neck of the hourglass-shaped shunt. Applicants' earlier ovine studies suggest otherwise. Specifically, the shunt lumen surface at the neck of the hourglass contained only microscopic amounts of cellular material. On gross pathological examination, there was no visible loss of the lumen area in neck region. A human shunt specimen has been examined in an explanted heart from a patient that underwent cardiac transplantation 2.5 years after shunt implantation. The ePTFE surfaces of the shunt including the lumen at the neck contained no pannus formation or narrowing of any kind.

In another example, a left atrial pressure sensor implanted across the FO by transseptal catheterization and used for guiding the medical therapeutic dosing in symptomatic patients with severe heart failure was observed to experience pannus formation. In the original embodiment of the sensor, the sensing diaphragm, located at the distal end of the sensor module body, protruded into the left atrium by 1-mm beyond its three anchoring legs that rested on the left atrial side of the septum. In a later, improved geometry version, the legs were placed more proximal on the sensor module body so that sensing diaphragm protruded into the LA by an additional 1.5 mm.

In a comparative inter-species pathology study, neoendocardial tissue (pannus) formation was observed over the sensing diaphragm in 20 of 31 original sensors compared with only 3 of 40 specimens with the improved geometry sensor. Of the 20 original sensors with tissue coverage, 7 had demonstrable artifacts in the LA pressure waveform. In each case with artifacts, pannus formation over the sensing diaphragm had a thickness >0.3 mm. These data indicate that when tissue coverage exceeds this thickness, the tissue interferes with fluid pressure measurement. None of the improved sensors had waveform artifacts or tissue thickness >0.3 mm.

In addition to producing waveform artifacts, the time course of tissue encapsulation of the sensing diaphragm could be estimated by assessing LA pressure waveforms for baseline drift with or without the development of artifacts. It was hypothesized that as neoendocardial tissue grows over the sensing diaphragm, measured LA pressure increased due to a drifting baseline caused by tension applied from the tissue capsule covering the diaphragm through its contiguous connection with the atrial wall. This healing phenomenon may be initiated as early as several weeks' post implant in animals and starts around 3-4 months in humans. Using the timing of drift to indicate tissue coverage in humans, it was shown that in a group of 46 heart failure patients with the original sensor design geometry, about 25% developed the characteristic drift pattern associated with tissue coverage of the sensing diaphragm during the first year after implantation. Of 41 similar patients implanted with the improved geometry sensor, none developed drift.

Pannus formation on devices that traverse the interatrial septum has been observed to start at the portions of the device in contact with the septum in the region of local tissue injury. Tissue growth progresses contiguously, extending translationally along the external surfaces of the device that protrude into each atrial chamber. This pannus growth thins as a function of distance from the sites of cardiac contact until it becomes essentially a monolayer of neoendothelial cells. The process naturally stops after about 6-12 months in humans. Thereafter, the remaining tissue may remodel but active growth of pannus is completed. From these data, Applicants observed that tissue coverage typically grows a distance of about 3 mm from its starting place on the septal wall before stopping or becoming thin enough so as not to impede device function.

Thus, for pannus to cause narrowing of the lumen at the shunt neck, it would have to extend contiguously from the site of injury on the septum for some distance to reach the neck. Applicants have determined that translational tissue growth over a distance of 3 or more millimeters becomes much less likely.

Pannus formation affecting the valve leaflets is the most likely stand-alone mechanism that explains all of the untoward observations seen in human subjects implanted with V-Wave shunts, including progressive shunt narrowing, incompetence of the valve with bidirectional flow, and eventual loss of shunt flow with associated loss of clinical efficacy.

Tissue overgrowth affecting the valve leaflets bases and commissures was the predominant histopathological finding in the ovine pre-clinical study described above. Gross pathological examination of shunts implanted for 3 months showed pannus infiltration extending from the adjacent FO into the valve leaflet bases with thickening of the leaflet bodies in 5 out of 6 shunts. In 4 shunts, there was fusion of at least 2 of the 3 valve commissures where the leaflet edges were sutured to the shunt frame. Fusion of all 3 commissures was observed in 3 shunts. One case showed severe narrowing at the commissures with a luminal area of 4 mm$^2$ or a 75% area stenosis in comparison to the normal 19.6 mm$^2$ lumen at the device neck. The leaflets were described as semi-pliable or stiffened in 4 out of 6 shunts. In two of the devices, commissural fusion and leaflet thickening were so pronounced that complete leaflet coaptation could not likely occur during valve closure. In none of these cases has pannus formation been seen to narrow the shunt neck.

On examination of microscopic sections, pannus thickness tends to be greater on the side of the leaflets facing the atrial septum where the ePTFE/leaflet junction was infiltrated with pannus that was contiguous with the adjoining atrial tissue. Pannus extended from the atrial septum on and around the right atrial edge of the ePTFE skirt and into the base and commissures of the valve leaflets. At 3 months, the pericardial leaflets showed varying degrees of pannus coverage ranging from mild to marked. In general, pannus is thickest at the leaflet bases and commissures, and tapers toward the free edges. In 2 sheep, the pannus on the leaflets measured 2 to 3 times the original thickness of the leaflets.

The pannus was generally well healed or organized by 3 months. It was composed of collagen and proteoglycan matrix surrounding smooth muscle cells, fibroblasts and rare focal areas of inflammation with lymphocytes, macrophages, and occasional multinucleated (foreign body type) giant cells. The pannus tissue was mostly covered with neoendothelium consistent with near complete healing. No leaflet calcification or thrombi were observed.

Although animal models of cardiovascular devices are limited in their ability to represent human tissue healing responses, the major differences are characteristically limited to the temporal duration of the response. For example, in a comparative pathology study described in the publication, "Comparative Pathology of an Implantable Left Atrial Pressure Sensor" by Roberts, et al., of a percutaneously implantable titanium/nitinol-enclosed LA pressure sensor, implanted on the interatrial septum, it was found that sheep at 1.5 to 8 months and canines implanted for 1 to 25 months, closely approximated the pathological findings seen in humans implants of 3 to 56 months duration. Histology had a similar appearance in humans and animals, and confirmed that the tissue covering the device was composed of a neoendocardium lined with a neoendothelium. The appearance of the neoendocardial tissue covering the sensor described above was similar to what is observed with ASD closure devices.

This mechanism of pannus formation preferentially affecting the bioprosthetic valve material compared to the ePTFE encapsulated portions of the shunt was observed in the human explanted specimen referred to earlier. After 2.5 year of implantation in heart, the 3 pericardial leaflets were severely thickened, immobile, infiltrated at their bases and commissures with pannus resulting in valvular stenosis with a reduction in outflow area of 52% relative to the non-obstructed shunt neck. Although this shunt was patent, it would have been incompetent, allowing bidirectional flow, and would have shunted less than half of the flow expected for any given pressure gradient.

To further evaluate the tendency of this bioprosthetic valve to become infiltrated with pannus, valved and valveless designs of the V-Wave shunt were implanted by applicants in a non-diseased juvenile ovine (n=9) model. Specifically, this study was designed to highlight the resistance of a valveless, ePTFE encapsulated shunt (n=6) to pannus formation, narrowing and occlusion, relative to the legacy valved version previously used in humans (n=3), by creating a highly proliferative model expected in healthy juvenile sheep where the left-to-right interatrial pressure gradient was expected to be small. In the valveless design, the bioprosthetic valve material and its attaching polypropylene suture were removed and the ePTFE encapsulation was extended to cover the entire nitinol frame of the shunt except for the last 1.5 mm on the RA side where the shunt was coupled to its delivery system for deployment. The ePTFE used had an internodal distance of up to 30 microns. At 12 weeks the sheep where euthanized. The gross pathology findings showed that the 3 valved shunts were heavily infiltrated with pannus formation, extending from the septum into the regions containing the bioprosthetic leaflets. The leaflets were fused, immobile and highly stenotic leaving only a pinhole opening. The degree of pannus formation was much exaggeration versus prior experience in the ovine heart failure model. Thick pannus extended retrograde contiguously from the leaflet bases toward the hourglass neck of the shunts. The pannus growth from the original septal site of injury to the tips of the valve leaflets exceeded 3 mm in distance. Pannus appeared to grow through the valve commissures and through the suture holes attaching the porcine pericardial leaflets to the frame and the ePTFE skirt. Pannus formation was associated with mononuclear inflammatory cell infiltrates and multinucleated giant cells.

All 6 of the valveless, ePTFE encapsulated shunts were widely patent with only minimal pannus formation attaching the FO tissue to the external surface of the device. Applicants observed no pannus growing translationally more than 3 mm along the external surface of the ePTFE from the septum. No visible pannus reached from the septum all the way into the lumen portion of either the left atrial entry cone or right atrial exit cone of the device. The lumina at the necks of all of the shunts were widely patent on gross and microscopic examination. There was no evidence of pannus formation permeating through the ePTFE encapsulation into the shunt lumen.

From these combined observations, applicants have determined that length of translational pannus growth from the site of healing may be dependent on the type of biomaterial surface. In the case of the ePTFE encapsulated shunt, pannus formation severe enough to interfere with device function tends to translate a maximum of about 3 mm from the site of injury, whereas in the case of the bioprosthetic valve material tested, the amount of pannus formation and translational length of pannus tissue growth were exaggerated.

Also, from these data, it is reasonable to expect that the near complete shunt healing seen after 3 months in the juvenile ovine model will be predictive of the histopathological findings in humans at 9-12 months. Moreover, these gross and microscopic observations, with their anticipated species-to-species conservation of findings, leads to the conclusion that the healing response in sheep is likely indicative of the mechanism causing shunt closure, valvular incompetence, and progressive stenosis in humans. Thus, there exists a need for a more durable shunt configuration that maintains luminal patency for extended periods of time.

It further would be desirable to provide a shunt for redistributing atrial blood volumes and reducing interatrial pressure imbalances that reduces the risk of paradoxical embolism caused by emboli transfer from the right to left atria.

It also would be desirable to provide an interatrial shunt configuration that reduces the risk of pannus formation after a prolonged period of implantation, where the degree of pannus formation and tissue ingrowth is not strongly dependent on the manner or location in which the shunt is implanted in the FO.

SUMMARY

In view of the foregoing drawbacks of previously-known interatrial shunts, a shunt constructed in accordance with the principles of the present disclosure provides a more durable configuration that maintains luminal patency for extended periods of time. The inventive shunt further enables redistribution of interatrial blood volumes and pressure imbalances while reducing a risk of paradoxical embolism caused by emboli moving through the shunt from the right to left atria.

Shunts constructed in accordance with the principles of the present disclosure also provide greater safety by enhancing long-term patency and reducing the risk of pannus formation after a prolonged period of implantation by reducing the impact of the manner in which the shunt is implanted in the interatrial septum.

In accordance with the principles of the present disclosure, shunts having an anchor and conduit are provided for redistributing atrial blood volumes, in which the shunt dimensions, contours and materials maintain long-term patency while reducing the risk of paradoxical embolism. It is hypothesized that such shunt designs will provide reductions in left atrial pressure, relieve pulmonary congestion, and lower pulmonary artery pressure, among other benefits. The inventive devices are configured for implantation through the atrial septum, and preferably through the fossa ovalis.

In particular, shunts designed in accordance with the principles of the present disclosure are designed to control LAP by transferring a small portion of the blood normally flowing from the left atrium to the left ventricle and diverting it instead to the right atrium, thereby modestly reducing LV end-diastolic filling volume. When the LAP is elevated, the LV operates on a steeper portion of its diastolic compliance curve. Accordingly, even a modest reduction in LV end-diastolic volume leads to a substantial fall in LV end-diastolic pressure. That reduction causes a commensurate reduction in upstream filling pressures including LAP, pulmonary venous pressure, and pulmonary artery pressure. The anticipated clinical result of these pressure reductions is to relieve or even prevent pulmonary congestive symptoms. At smaller interatrial gradients with less shunting, the effect on LV volume and filling pressures becomes progressively smaller until it is negligible. As interatrial shunting primarily affects LV filling and not afterload, beneficial effects on lowering end-diastolic pressure are expected, regardless of LV systolic function, for patients with heart failure associated with reduced ejection fraction (HFrEF) and patients with heart failure and preserved ejection fraction (HFpEF).

In accordance with one aspect of the present disclosure, the inventive devices include an anchor configured to be implanted in the interatrial septum, preferably the FO, and a conduit affixed to the anchor. The conduit includes a luminal wall defining a lumen, such that the luminal wall comprises a biocompatible material that is resistant to transmural tissue growth, and that limits translational tissue growth to 3 mm or less from the site of contact to the nearest cardiac structure. In one preferred embodiment, that anchor may have an hourglass or "diabolo" shaped frame with a neck region adjoining flared end regions, and the conduit may comprise a biocompatible material that encapsulates the frame. The frame may be formed of a biocompatible elastically or plastically deformable material, or shape memory material. The device may be implanted by forming a puncture through the atrial septum, particularly through the FO, and then percutaneously inserting the device therethrough, such that the neck region lodges in the puncture, the first end region extends into the left atrium, and the second end region extends into the right atrium.

The biocompatible material that may be a polymer, such as expanded polytetrafluoroethylene (ePTFE), polyurethane, DACRON (polyethylene terephthalate), silicone, polycarbonate urethane, Ultra High Molecular Weight Polyethylene (UHMWPE) or PTFE. The biocompatible material may also be a metal, ceramic, carbon nanotube array or any other suitable material known to those familiar with the art that provides the shunt with the following properties. One purpose of the biocompatible covering is to form a conduit, with the biocompatible material serving as a barrier to isolate the shunt lumen from the exterior of the conduit. Additionally, the biocompatible material isolates the lumen from penetration by cellular proliferation (pannus formation) occurring on the exterior surface of the conduit, where it contacts the septum or FO, which result from the processes associated with device healing. The biocompatible material should also impede translational growth of pannus along the outer wall of the conduit for more than about 3 mm from the site of contact with any cardiac structure.

The concept of having a separate anchor to provide shape and a conduit to provide isolation, which when combined comprise the shunt, is solely for the general convenience of developing practical device embodiments. It will be apparent to one skilled in the art that a shunt device with the requisite shape, expansion and covering characteristics could be constructed from a single unitary material that serves as both anchor and conduit. For example, one such embodiment may comprise injection molded silicone rubber that forms a single piece self-expanding shunt. Also, superelastic polymers are under development that have mechanical and biocompatible properties comparable to nitinol alloys. Thus, the anchor or frame used interchangeably throughout this specification should be considered in the general sense to refer to any composition of linked physical members that contribute in substantial part to the shunt device's shape and other physical properties that govern the shunt's transition from pre-deployment constrainment to the expanded and deployed state where it is in contact with tissue. All of the shunt device embodiments described in this patent application can be understood in terms of component parts (anchor and conduit) or as a unitary device with certain specified physical properties including shape geometry in pre-and post-deployment states and biocompatible surface properties.

The cross-sectional profile of shunt lumen perpendicular to its axis of flow may be round, oval, rectangular, or any other regular or irregular polygonal shape. The cross-sectional profile may vary from one shape to another along the axis of flow, which may be a straight line or may be curvilinear. The cross-sectional profile may rotate along the axis of flow. The shunt may have a single lumen or there may be a plurality of lumina.

In one aspect of the present disclosure, a device for regulating blood distribution between a patient's left atrium and right atrium comprises an anchor having a neck region joining first and second end regions, the neck region configured to engage the fossa ovalis of the patient's atrial septum; and a conduit affixed to the anchor so that the conduit extends into the right atrium by a distance selected to reduce the risk of paradoxical embolism. The conduit preferably comprises a biocompatible material that limits (or inhibits excessive) tissue ingrowth into the lumen of the conduit. The anchor and conduit are configured to accommodate endothelial or neointima layer growth up to a thickness of about 0.6 mm or less, so as to render such material inert, inhibit hyperplasia, and substantially inhibit obstruction of the flow path through the device.

In one preferred embodiment, the anchor comprises hourglass-shaped frame having a plurality of circumferential struts interconnected by longitudinal struts that, when deployed, form first and second flared end regions connected by a neck. In some embodiments, when the shunt is deployed across the patient's atrial septum, the first flared end region protrudes 3 to 10 mm into the left atrium beyond the surface of the left septal wall. The second flared end region may protrude 5 to 10 mm into the right atrium beyond the surface of the right septal wall. The neck has an inner diameter of 4 to 8 mm, where preferably the inner diameter is in a range of 5 to 6.5 mm. The first flared end region preferably has a diameter selected in the range of between 10 and 20 mm, and the second flared end region preferably has a diameter selected in the range of between 9 and 15 mm. The first and second flared end regions each preferably flare outward from the longitudinal axis of the shunt by an amount selected from between about 25 to 60 degrees, although such angles may be different for each of the first and second flared regions. For example, in one embodiment, the steepest part of the outer surface of the first flared end region is at an angle of approximately 40 degrees relative to the longitudinal axis of the device, while the steepest part of the outer surface of the second flared end region may be at an angle of approximately 37.5 degrees relative to the longitudinal axis of the device.

In preferred embodiments, the shunt is configured to transition between a collapsed state suitable for percutaneous delivery and an expanded state when deployed across the patient's fossa ovalis, such that the shunt assumes an hourglass configuration in the expanded state. The hourglass configuration may be asymmetric. The shunt may be configured for implantation through a portion of the fossa ovalis, away from the surrounding limbus, inferior vena cava, and atrial wall.

Methods of treating a subject with heart pathology also are provided, including providing a shunt having first and second end regions and a neck region disposed therebetween; deploying the shunt across a puncture through the subject's interatrial septum, preferably through the FO, such that the neck region is positioned in the puncture with the first end region disposed in the left atrium, and the second end region disposed in the right atrium, such that flow through the device redistributes blood between the left atrium and the right atrium through the device when the left atrial pressure exceeds the right atrial pressure.

Subjects with a variety of heart pathologies may be treated with, and may benefit from, the inventive device. For example, for subjects with heart failure and pulmonary congestion, reducing the left atrial pressure and left ventricular end diastolic pressure may provide a variety of benefits, including but not limited to decreasing pulmonary congestion; decreasing pulmonary artery pressure; increasing ejection fraction; increasing fractional shortening; and decreasing left ventricle internal diameter in systole. Other heart pathologies that may be treated include myocardial infarction, which may be treated by deploying the device during a period immediately following the myocardial infarction, e.g., within six months after the myocardial infarction, or within two weeks following the myocardial infarction, to reduce myocardial remodeling.

Patients with pulmonary arterial hypertension (PAH) due to idiopathic cause or associated with other disorders such as connective tissue diseases, drugs or toxins, HIV infection, portal hypertension, or congenital heart disease have been shown to benefit from atrial septostomy procedures that cause interatrial shunting from the right to the left atrium (right to left shunt). These procedures include blade or balloon septostomy or placement of devices such as uncovered diabolo stents or fenestrated atrial septal occlusion devices. It will be apparent to persons of skill in the art that the embodiments already described and other preferred embodiments described in this patent specification are applicable to treating patients with PAH.

In accordance with another aspect of the present disclosure, a system for treating a heart condition is provided. The system may include a sheath having a lumen and distal end sized and shaped to be positioned through an opening of an atrial septum of a patient, and a shunt including an anchor and a conduit, e.g., a biocompatible material that encapsulates at least a portion of the anchor. The anchor may have a first region, a second region, and a neck region joining the first and second regions, and the conduit may be affixed to the anchor to define a passageway through the shunt. The shunt may transition from a contracted delivery state within the lumen of the sheath to an expanded state. In addition, the system may include a delivery catheter movably disposed within the lumen of the sheath that may advance the shunt through the lumen of the sheath until the first region protrudes from the distal end of the sheath and transitions from the contracted delivery state to the expanded state within a first atrium. The shunt and the sheath may be retracted towards the atrial septum until the first region in the expanded state engages with the atrial septum within the first atrium, and the sheath may further be retracted until the second region of the anchor is exposed from the distal end of the sheath and transitions from the contracted delivery state to the expanded state within a second atrium to implant the neck region at the atrial septum.

The force required to retract the sheath over the second region in the contracted delivery state is less than a force required to transition the first region from the expanded state to the contract delivery state. Moreover, the force required to retract the sheath over the second region in the contracted delivery state is less than a yield stress of the atrial septum. The anchor may form a diabolo shape in the expanded state. The first and second regions may be formed of a superelastic or a shape memory material. In addition, the passageway may maintain a continuous opening across the atrial septum in the expanded state. The delivery catheter may be detachably coupled to the shunt in the contracted delivery state within the lumen of the sheath.

Moreover, the delivery catheter may advance the shunt through the lumen of the sheath until the delivery catheter reaches a stopping point such that the first region protrudes from the distal end of the sheath a predetermined distance. Additionally, the delivery catheter may be retracted from the stopping point such that the sheath causes the first region to transition from the expanded state to the contracted delivery state for retrieval of the shunt. The system further may include a guidewire that may be positioned through the opening of the atrial septum of the patient, such that the sheath may be positioned through the opening of the atrial septum over the guidewire. Further, the system may include a dilator that may be advanced over the guidewire to dilate the opening of the atrial septum, and may be removed through the lumen of the sheath.

In accordance with another aspect of the present disclosure, a method for redistributing blood across a patient's interatrial septum is provided. The method may include: positioning the distal end of the sheath through an opening of the atrial septum; advancing the shunt through the lumen of the sheath via the delivery catheter until the first region of the anchor protrudes from the distal end of the sheath and transitions from the contracted delivery state within the lumen of the sheath to the expanded state within the first atrium; retracting the shunt and the sheath towards the atrial septum until the first region in the expanded state contacts the atrial septum within the first atrium; further retracting the sheath until the second region of the anchor is exposed from the distal end of the sheath and transitions from the contracted delivery state to the expanded state within the second atrium to thereby lock the shunt within the atrial septum; and shunting blood via the passageway of the conduit between the first and second atria.

For example, advancing the shunt through the lumen of the sheath via the delivery catheter may include advancing the delivery catheter until the delivery catheter reaches a first stopping point wherein the shunt is within 1 to 5 cm from the distal end of the sheath, and advancing the delivery catheter to a second stopping point such that the first region protrudes from the distal end of the sheath a predetermined distance. The method further may include verifying that the distal end of the sheath is positioned within 1 to 3 cm beyond the atrial septum prior to advancing the delivery catheter to the second stopping point.

Moreover, retracting the shunt and the sheath may include retracting the shunt and the sheath towards the atrial septum until contact with the atrial septum is observed. In addition, further retracting the sheath until the second region is exposed from the distal end of the sheath may include further retracting the sheath until a counterforce exerted by shunt tension on the atrial septum overcomes a friction of the second region in the contracted delivery state within the sheath. The method further may include decoupling the delivery catheter from the shunt prior to further retracting the sheath until the second region is exposed from the distal end of the sheath.

Further, the method may include injecting an agitated saline via the delivery catheter, and observing where microbubbles of the agitated saline exit the distal end of the sheath via ultrasonic imaging to confirm a position of the distal end of the sheath within the first atrium. Additionally or alternatively, the method may include injecting radiographic contrast material via the delivery catheter, and observing where the radiographic contrast material exits the distal end of the sheath via fluoroscopy to confirm a position of the distal end of the sheath within the first atrium.

BRIEF DESCRIPTION OF DRAWINGS

FIGS. 16A and 16B are, respectively, side and end views of anchor suitable for a further alternative shunt embodiment having self-expanding flexible arms that form a filter over the right atrial side of the conduit.

FIG. 17 is a graph comparing theoretical flows through shunt designs constructed in accordance with the principles of the present disclosure compared to a previously known valved shunt design.

FIGS. 20A to 20D schematically illustrate steps taken during the method of FIG. 19, in accordance with the principles of the present disclosure.

DETAILED DESCRIPTION

Interatrial shunts are provided for redistributing interatrial blood volumes and reducing left atrial pressure, which may be advantageous in treating subjects suffering from heart failure (HF) or other disorders associated with elevated left atrial pressure. A preferred embodiment of the inventive device includes an anchor, which may be an hourglass or "diabolo" shaped stent or frame, and a conduit, formed by encapsulating the frame in a synthetic biocompatible material. The shunt is configured to be lodged securely within a passage formed in the atrial septum, preferably the fossa ovalis, and provides one-way blood flow from the left atrium to the right atrium, when blood pressure in the left atrium exceeds that on the right.

Figure 1A:
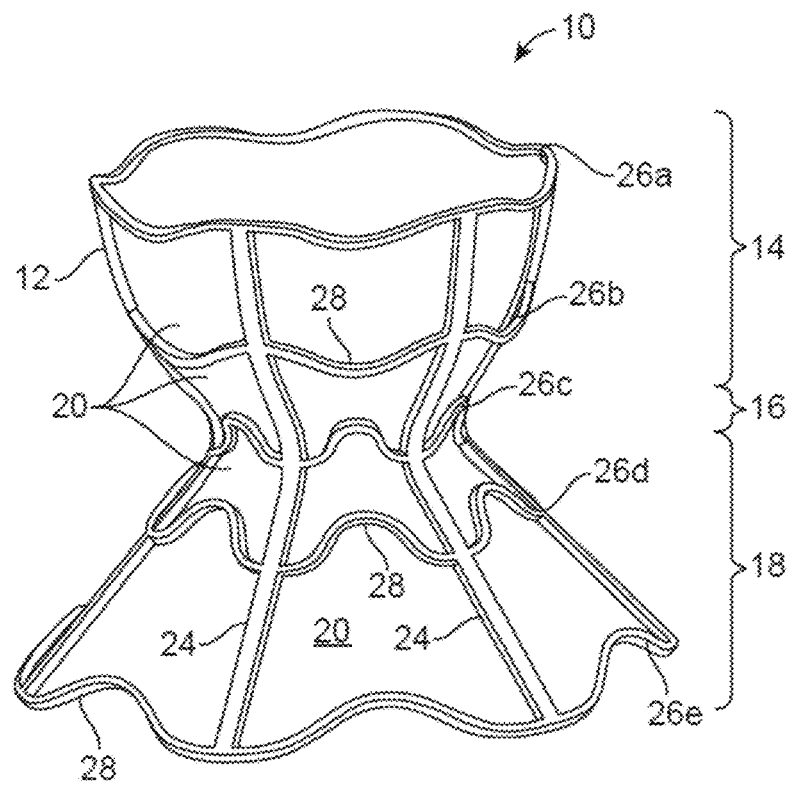
FIGS. 1A to 1C are, respectively, perspective, end and side views of a preferred embodiment of a shunt constructed in accordance with the principles of the present disclosure.
Figure 1B:
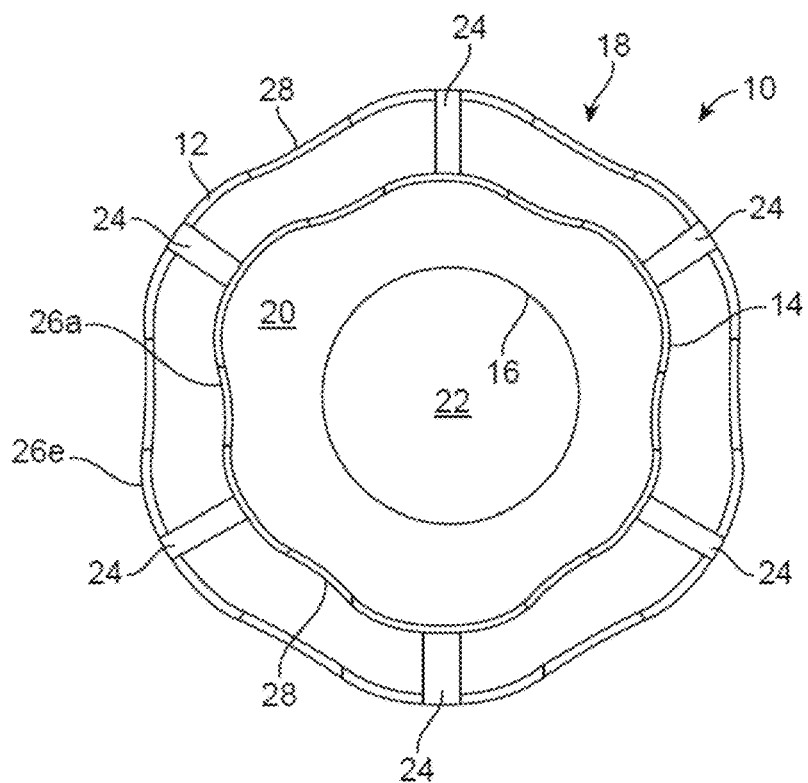
Figure 1C:
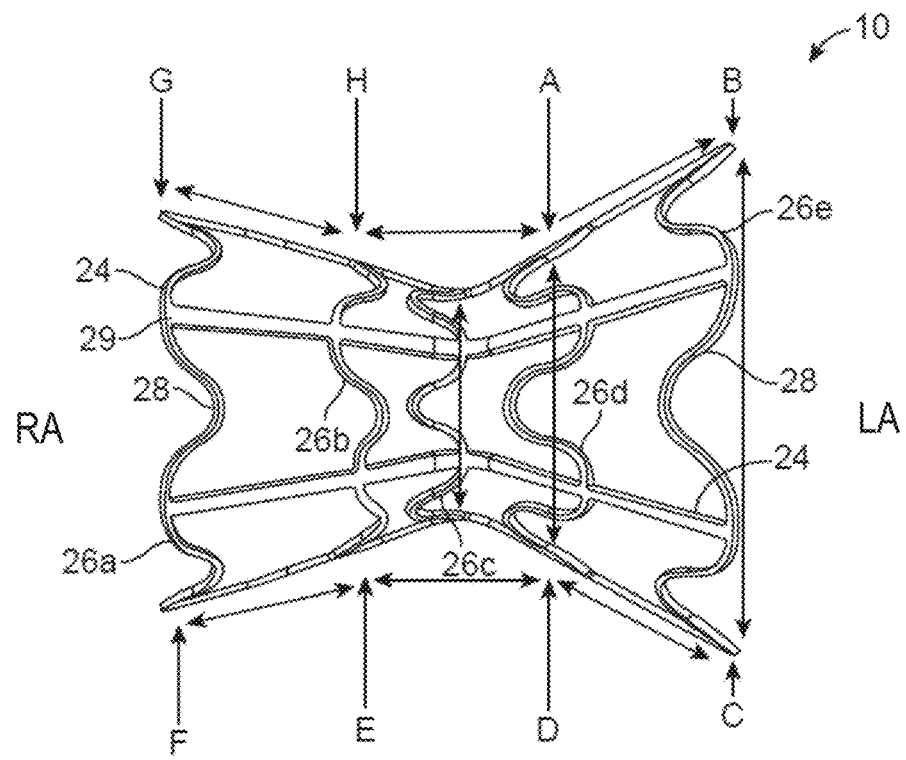

Referring now to FIGS. 1A to 1C, an illustrative embodiment of shunt 10 of the present disclosure is described. Shunt 10 generally comprises anchor 12 having three regions: flared or funnel-shaped end region 14, flared or funnel-shaped end region 18, and neck region 16 disposed between end regions 14 and 18. Neck region 16 is configured to lodge in a puncture formed in the atrial septum, preferably in the fossa ovalis. Flared end regions 14 and 18 are configured to partially engage and protrude beyond the right and left sides, respectively, of the atrial septum when implanted. Shunt 10 further comprises a conduit, illustratively formed by encapsulating anchor 12 with biocompatible material 20 that covers all or substantially all of anchor 12 to form a conduit defining a lumen or interior passageway 22.

Flared region 14 is configured to be disposed in the right atrium, while flared region 18 is configured to be disposed in the left atrium. In one embodiment, anchor 12 includes six longitudinal struts 24 interconnected by five circumferential struts 26a-26e. Longitudinal struts 24 prevent foreshortening of the anchor during expansion, while the sinusoidal or serpentine bends in circumferential struts 26a-26e permit the anchor to transition between a radially collapsed substantially cylindrical delivery state to an expanded, flared, deployed state as illustrated in FIGS. 1A to 1C. As depicted in the figures, a conduit is formed by biocompatible material 20 that encapsulates the entirety of neck 16, flared end region 18, and flared end region 14. Biocompatible material 20 preferably is affixed to anchor 12 using a suitable biocompatible adhesive or by sandwiching the anchor between inner and outer layers of biocompatible material using sintering techniques.

In a preferred embodiment, anchor 12 comprises a self-expanding material, such as a shape memory alloy, and circumferential struts 26a-26e are treated to expand a predetermined amount when deployed, so that together with encapsulation 20, lumen 22 has a contour that permits substantially laminar flow between flared end section 18 (in the left atrium) and flared end section 14 (in the right atrium). Sinusoidal or serpentine bends 28 in circumferential struts on flared end region 14 preferably are 180 degrees out of phase with the sinusoidal or serpentine bends 28 in neck region 16 and flared end region 18, so that the sinusoidal or serpentine bends do not extend beyond the ends of longitudinal struts 24 in either the collapsed delivery state or deployed state.

Anchor 12 may comprise a biocompatible metal framework or laser-cut solid metallic tube made from nitinol, titanium alloy, cobalt chromium alloy, MP35n, 316 stainless steel, L605, Phynox/Elgiloy, platinum chromium or other biocompatible metal such as are known to persons of skill in the art. While a preferred embodiment employs a shape memory self-expanding alloy, anchor 12 alternatively may comprise an elastically or plastically deformable material, e.g., balloon expandable, or may be a shape memory alloy that responds to temperature changes to transition between contracted delivery and expanded deployed states. The surface finish applied to the material of the anchor may be selected to control the distance, thickness, composition and/or growth pattern of pannus formation, e.g., the external surfaces of anchor 12 may be electro-polished.

In accordance with the principles of the present disclosure, the radial dimensions, axial lengths and contours of neck region 16 and flared end regions 14 and 18 preferably are selected to provide laminar flow through the interior of the shunt, to reduce the formation of eddy currents when implanted, and thus inhibit thrombus formation; to inhibit pannus formation that could obstruct the neck region; to promote tissue ingrowth around the exterior of the neck region to secure the shunt against migration; to provide a desired rate of blood flow between the left and right atria at physiological pressure differentials; and to prevent retrograde paradoxical embolization.

Biocompatible material 20 forming the conduit preferably is resistant to the transmural and translational ingrowth of pannus material having a tissue thickness greater than 0.6 mm. For example, in experimental ePTFE vascular grafts, those with a 60-micron internodal distance showed rapid, transmural infiltration with proliferating smooth muscle cells and granulation tissue, whereas ePTFE grafts with a 30-micron internodal distance were observed to develop only a slow growing, thin sheet of endothelium that advanced only a few millimeters into the graft lumen from the adjacent artery. Porous polyester fabric coverings employed on some atrial septal defect ("ASD") occlusion devices would be poor choices for use in the shunt of the present disclosure, because such materials become completely enmeshed with penetrating fibrotic tissue. It is expected that when shunt 10 comprises anchor 12 made of, for example, electro polished nitinol, and biocompatible material 20 may be an inert polymer such as ePTFE with an internodal distance of 30 microns or less, or is PTFE, such that pannus will grow to a thickness no greater than about 0.6 mm after extending translationally a distance of 3 mm from the site of contact with the Foramen Ovalis ("FO") tissue. In such cases, interior lumen of the conduit is not expected to narrow beyond a total of 1.2 mm from its original diameter and the neck. For the purposes of this patent the term "luminal narrowing" shall be defined as a loss of minimal shunt lumen diameter of greater than 25% and the term "luminal obstruction" is defined as total (100% loss of lumen diameter) blockage of the lumen to the flow of blood.

In the preferred embodiment depicted in FIGS. 1A to 1C, anchor 12 has an hourglass shape formed of a shape memory metal, e.g., nitinol, or any other suitable material known in the art. Circumferential struts 26a-26e and longitudinal struts 24 preferably comprise a unitary construction, that is, entire anchor 12 is laser cut from a tube of shape memory metal. Biocompatible material 20 may comprise, for example, a sheet of a polymer such as expanded polytetrafluoroethylene ("ePTFE"), polytetrafluoroethylene ("PTFE",) silicone, polycarbonate urethane, DACRON (polyethylene terephthalate), Ultra High Molecular Weight Polyethylene (UHMWPE), or polyurethane. The biocompatible material may also be a metal, ceramic, carbon nanotube array or any other suitable biocompatible material. For example, biocompatible material 20 may comprise ePTFE with an up to 30-micron internodal distance, and may be applied as inner and outer layers sintered together to form a unitary conduit. Alternatively, biocompatible material 20 may be applied to the inner lumen and the outside of the anchor using electrospinning techniques. Other methods of encapsulation and other suitable polymers that prevent transmural ingrowth of pannus tissue may alternatively be used, as will be understood by one skilled in the art. Bare metal regions of anchor 12, and any other regions of the anchor, optionally may be electropolished or otherwise treated to inhibit thrombus formation using known methods.

As noted above, neck 16 of shunt 10 preferably is configured for implantation through the fossa ovalis of the atrial septum, and more preferably near or at the central portion of the fossa ovalis. As known to those skilled in the art, the fossa ovalis is a thinned portion of the atrial septum formed during fetal development of the heart, which appears as an indent in the right side of the atrial septum and is surrounded by a thicker portion of the atrial septum. While the atrial septum itself may be several millimeters thick and muscular, the fossa ovalis may be only approximately one millimeter thick, and is formed primarily of fibrous tissue.

In some embodiments of the present disclosure, shunt 10 may be asymmetrically shaped to take advantage of the natural features of the atrial septum near the fossa ovalis, and to provide suitable flow characteristics. For example, in a preferred embodiment, the anchor comprises an hourglass or diabolo shape where a LA entry funnel resembles a conical-shaped nozzle and a RA exit funnel is "bell" shaped, with the wide mouth lumen of the bell at the RA exit port in the RA. The narrow entrance to the bell-shaped exit funnel connected to the orifice of the neck region may be configured to approximate the curved surface of a parabola. This type of convergent-divergent nozzle resembles the shape of a classical de Laval nozzle used in rocket engines. Left to right flow is largely governed by the smooth convergence of streamlines in the entry cone and the divergence of streamlines exiting the bell. Such a nozzle configuration is very efficient in the forward flow direction having a discharge coefficient resembling a classic venturi tube, e.g., 0.95-0.98.

Referring now to FIG. 1C, points B and C are located on the leftmost circumferential strut 26e, which defines the LA entry port. Points A and D are located on circumferential strut 26d along the LA entry funnel proximal to strut 26e. Points H and E are located on circumferential strut 26b along the RA exit funnel, and points G and F are located on circumferential strut 26a, which defines the RA exit port. In preferred embodiments, the diameter of lumen 22 in the neck region of the shunt orifice ranges from 5 to 6.5 mm. The portion of the shunt crossing the FO, bounded by points ADEH may be 3 mm in axial length but may be extended up to 10 mm in patients with a thicker FO. The diagonal length between points AB, CD, EF, and/or GH is preferably ≥3 mm so that pannus cannot grow translationally inward from the ends of the shunt and thus obstruct neck region 16. In addition, the horizontal component length between points AB, CD, EF, and/or GH is preferably ≤15 mm, to avoid interference with existing cardiac structures when implanted. In accordance with another aspect of the disclosure, it has been determined that providing a length of segments EF and GH generally greater than 5 mm is expected to ensure that the end region that extends into the right atrium is disposed generally out of the flow path of blood returning from the inferior vena cava, which is most likely to have entrained emboli that could cause paradoxical embolization. Truncated funnel cones bounded by ABCD and/or EFGH may have volumes ≤2 ml.

Other embodiments of the shunt of the present disclosure may include anchors with different combinations and configurations of circumferential ring and axial strut elements. Specifically, such embodiments, may have more or less than 6 longitudinal struts 24 and more or less than five circumferential struts 26a-26e. These configurations may yield other shunt lumen geometries. In another embodiment, anchor 12 may be made of a self-expanding polymer. Alternatively, the anchor need not be self-expanding, and may be made from a plastically deformable biocompatible metal such as 316 L stainless steel, cobalt chromium alloys, or any other such suitable materials known to those skilled in the art. Such a deformable shunt anchor may be delivered by an expanding member, such as a balloon, that is configured to achieve the desired luminal geometry. The deformable anchor may be designed to expand prismatically or at certain localized sites where ductile hinges are configured for more selected expansion as taught by U.S. Pat. No. 6,242,762 to Shanley, the contents of which are incorporated by reference herein.

Figure 2:
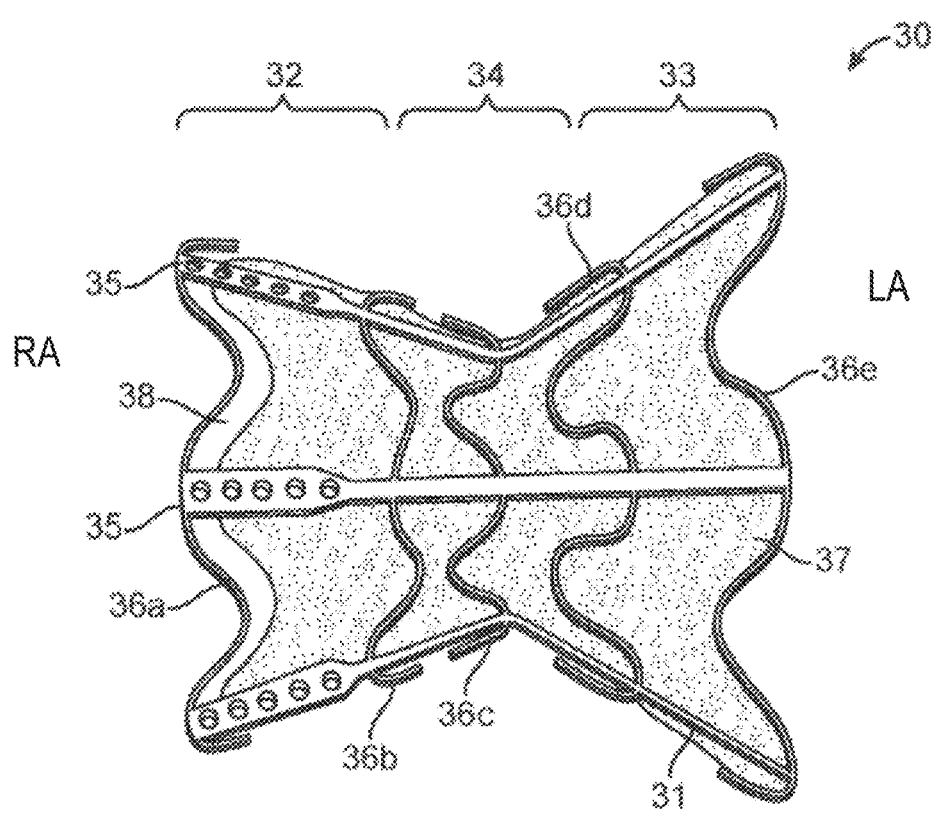
FIG. 2 is a side view of an alternative embodiment of a shunt of the present disclosure having a cutout in its polymeric encapsulation to secure the shunt to a delivery system.

Referring now to FIG. 2, an alternative embodiment of a shunt constructed in accordance with the principles of the present disclosure is described. Shunt 30 includes anchor 31 is similar in construction to that described for the embodiment of FIGS. 1A-1C, and has flared end regions 32 and 33 and neck region 34. When implanted in a patient's interatrial septum, flared end region 32 is disposed in the patient's right atrium, while flared end region 33 is disposed in the patient's left atrium, with neck region 34 situated in a passage formed in the interatrial septum. Anchor 31 includes longitudinal struts 35 and circumferential struts 36a-36e, and is encapsulated by biocompatible material 37. Anchor 31 may comprise a self-expanding or plastically deformable material as described herein above.

Shunt 30 of FIG. 2 differs from the previous embodiment in that biocompatible material 37, for example ePTFE, includes cutout 38 adjacent to circumferential strut 36a. Cutout 38 may extend proximally from circumferential strut 36a for a distance of 0.5 mm to 2 mm, and more preferably about 1 mm, to permit circumferential strut 36a to be releasably engaged with a delivery system during deployment, for example, hooks, as described by Yacoby in U.S. Pat. No. 9,713,696, the entire contents of which are incorporated herein by reference. Biocompatible material 37 may be trimmed manually or mechanically from circumferential strut 36a to create cutout 38 or by laser-cutting. In this manner, shunt 30 may be positioned and repositioned in a passage formed in the interatrial septum until the clinician is satisfied with the device placement, before being released.

As shown in FIG. 2, each of longitudinal struts 35 optionally may include one or more holes adjacent to circumferential strut 36a, e.g., to permit longitudinal struts 35 to be releasably engaged with a delivery system during deployment. Although FIG. 2 illustrates each of longitudinal struts 35 having one or more holes, not every longitudinal strut may include the one or more. For example, if six longitudinal struts 35 form anchor 31, only three longitudinal struts may include one or more holes adjacent to circumferential strut 36a. Accordingly, the longitudinal struts without one or more holes may be narrower.

In a preferred embodiment, the conduit formed by biocompatible material 37 extends a distance of at least 3 mm beyond neck region 34 into flared end region 32, to ensure that pannus cannot grow translationally along luminal wall far enough to partially occlude the flow area of neck region 34. Additionally, flared end region 32 extends a distance of at least 5 mm into the right atrium when implanted in the interatrial septum to ensure that the entry of flared end region 34 is generally not aligned with flow paths generated by blood entering the right atrium from the inferior vena cava, thereby reducing the risk that emboli carried from the lower extremities into the right atrium will cause paradoxical embolism by passing through shunt 30.

Figure 3:
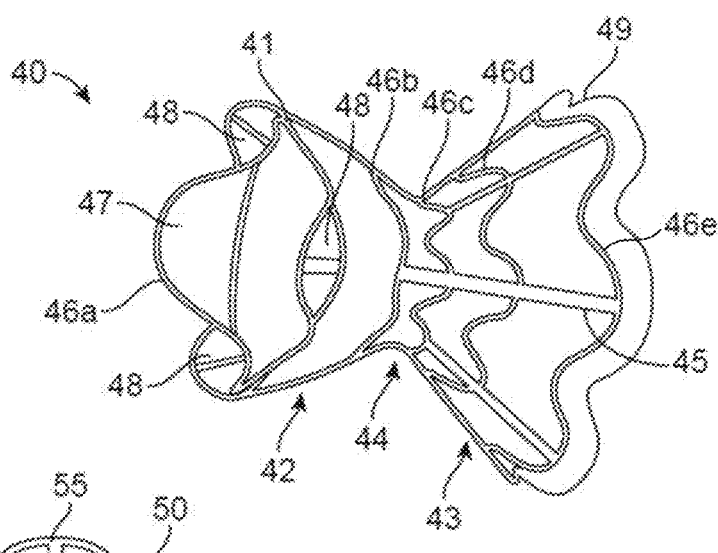
FIG. 3 is a perspective view of another alternative embodiment of a shunt of the present disclosure having an alternative cutout in its encapsulation.

With respect to FIG. 3, another alternative embodiment of inventive shunt is described. Shunt 40 includes anchor 41 having flared end regions 42 and 43 joined by neck region 44, as described for the preceding embodiments. Anchor 41 includes longitudinal struts 45 joined by circumferential struts 46a-46e and biocompatible material 47, for example a thin layer of ePTFE or other suitable material as described above. Shunt 40 differs from the embodiment of FIGS. 1A to 1C in that the polymeric encapsulation includes cutouts 48 on alternating peaks of the sinusoidal bends formed by circumferential strut 46a that permit a delivery device to releasably engage shunt 40. Shunt 40 also includes skirt 49 of biocompatible material that extends beyond circumferential strut 46e. In a preferred embodiment, cutouts 48 include circular sectors having angles in the range of 60° to 180°, more preferably 120°, such that largest distance between the edge of the polymeric encapsulation and circumferential strut 46a is in the range of 0.5 to 2 mm, and more preferably 1 mm. The configuration of cutouts 48 of shunt 40, which may be laser cut, advantageously maximize the encapsulated area of the shunt while still enabling proper engagement to the delivery system hooking mechanism. As will be apparent to those skilled in the art, other possible cutting patterns or methods may be employed.

Figure 4A:
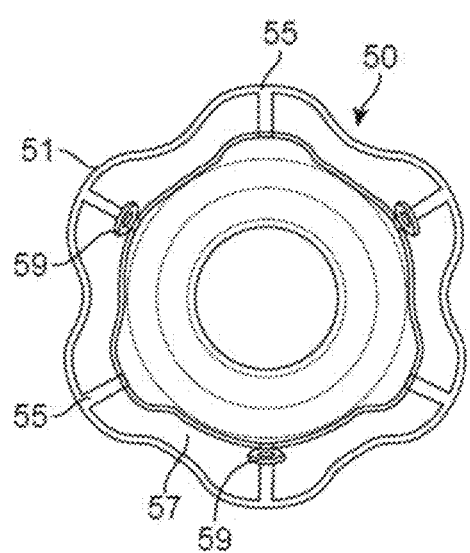
FIGS. 4A and 4B are, respectively, end and side views of a further alternative embodiment of a shunt constructed in accordance with the principles of the present disclosure having eyelets that engage a delivery system.
Figure 4B:
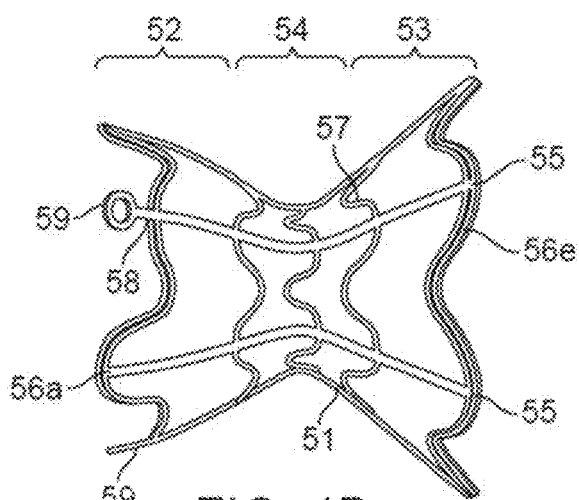

Referring now to FIGS. 4A and 4B, another embodiment of a fully encapsulated hourglass shunt constructed in accordance with the principles of the present disclosure is described. Shunt 50 includes anchor 51 having end regions 52 and 53 joined by neck region 54. Anchor 51 has longitudinal struts 55 coupled to circumferential struts 56a-56e as described for preceding embodiments, and includes a conduit formed of biocompatible material 57 as also described hereinabove. Shunt 50 differs from the embodiment of FIGS. 1A to 1C in that alternating longitudinal struts 55 include elongated portions 58 having eyelets 59 for engagement with a delivery system extending from right atrial end region 52. Shunt 50 may have between 2 to 6, and preferably 3 elongated portions 58 and eyelets 59 left as bare-metal, i.e., without polymeric encapsulation. Elongated portions 58 preferably are short, protruding a minimum additional distance into the right atrium or alternatively are constructed to bend into the right atrium RA exit port on release from the delivery system to serve as filter to block paradoxical emboli from passing into the lumen of the conduit at end region 52. An alternative approach that also filters the size of emboli is to construct the shunt with a plurality of passageways or lumina that transport blood in parallel such that the total cross-sectional area of all the of the passageways conserves the flow characteristics needed for adequate shunting to achieve the redistribution of blood between the atria as desired.

Figure 5A:
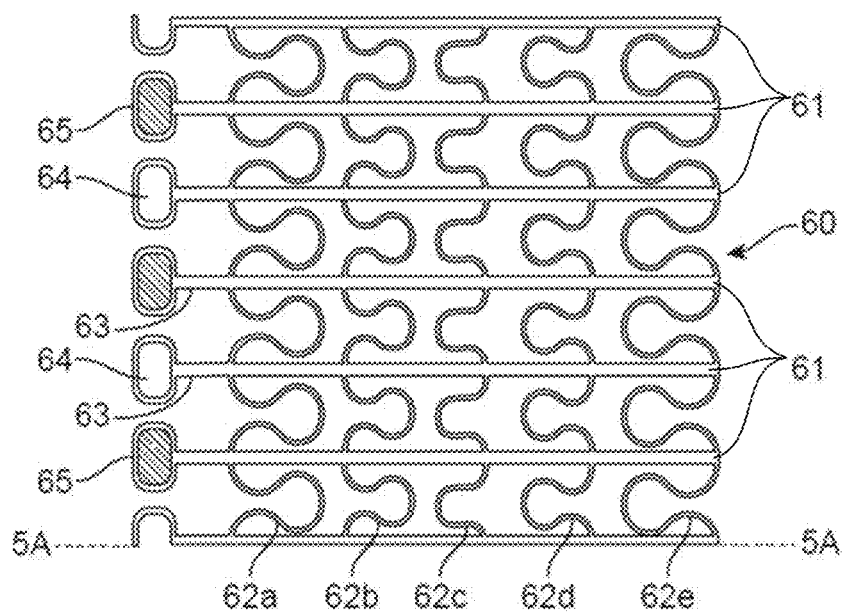
FIGS. 5A and 5B are plan views of further alternative embodiments of anchors suitable for use in the inventive shunt, cut along line 5A-5A and 5B-5B, and unrolled to a flat configuration.
Figure 5B:
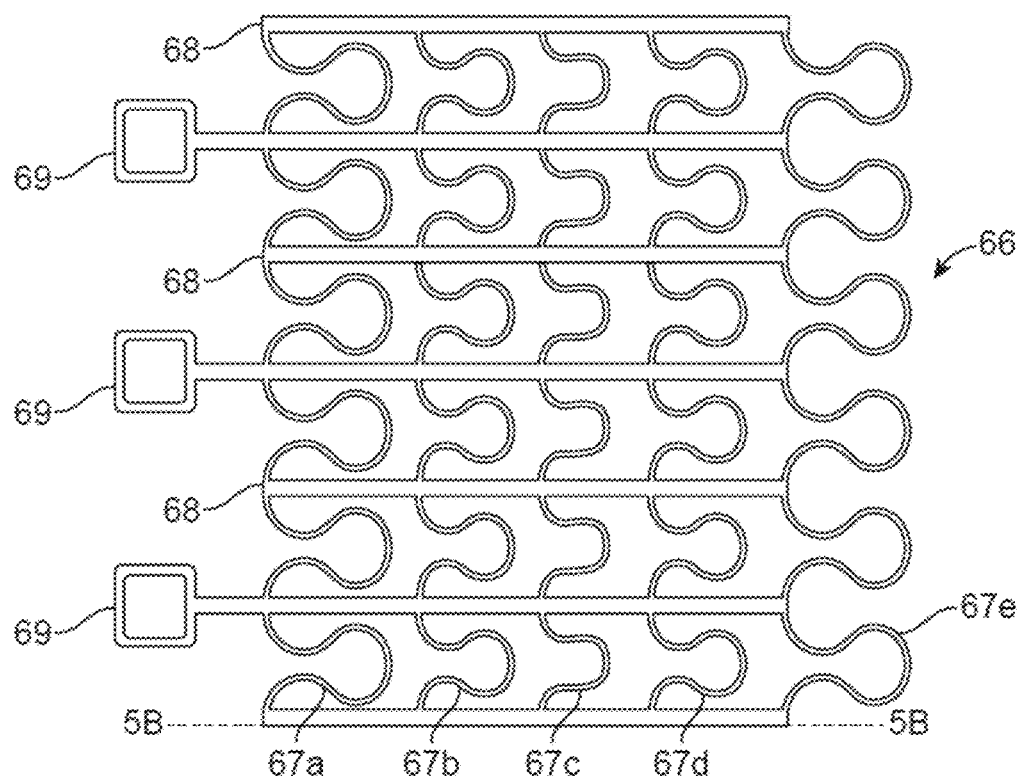

With respect to FIGS. 5A and 5B, further alternative embodiments of an anchor suitable for constructing a shunt in accordance with one aspect of the present disclosure are described. Anchor 60 is similar in design to anchor 51 of the embodiment of FIGS. 4A and 4B, and includes longitudinal struts 61 joined to circumferential struts 62a-62e, which include sinusoidal bends. Accordingly, anchor 60 when expanded includes flared end regions joined by a neck region to form a generally hourglass shape, while longitudinal struts 61 prevent, or otherwise minimize, foreshortening, i.e., axial shrinkage, during deployment. For purposes of illustration, anchor 60 as depicted in FIG. 5A is shown cut along one of longitudinal struts 61 (along line 5A-5A) and flattened, although the anchor preferably is cut from a tubular material. As for preceding embodiments, anchor 60 includes a polymeric encapsulation that forms a conduit, omitted for clarity from FIG. 5A, that covers the anchor between circumferential struts 62a and 62e. Anchor 60 includes elongated portions 63 and eyelets 64 that extend into the right atrium when the shunt is deployed. In accordance with one aspect of the disclosure, alternating eyelets 64 include radiopaque markers 65, for example made of platinum iridium, gold, tantalum, or any other similar suitable material, which enhance visualization of the shunt under fluoroscopy. Eyelets 64 that do not accommodate radiopaque markers 65 permit the shunt to be releasable engaged by a delivery system for percutaneous transluminal delivery.

In FIG. 5B, anchor 66 is similar in design to anchor 60 of the embodiment of FIG. 5A, except that in this embodiment circumferential struts 67a-67e having sinusoidal bends that extend between longitudinal struts 68 all face in the same direction. Anchor 66 additionally includes eyelets 69 that extend from alternating longitudinal struts 68 for use in releasably coupling the shunt to a percutaneous transluminal delivery system. One advantage of this design is that retrieval of a self-expanding shunt using anchor 66 by its delivery system when halfway deployed or fully deployed, requires less pull-back force to collapse the shunt than the embodiment of FIG. 5A. As in preceding embodiments, anchor 66 when expanded includes flared end regions joined by a neck region to form a generally hourglass shape, while longitudinal struts 68 prevent, or otherwise minimize, foreshortening during deployment. For purposes of illustration, anchor 66 as depicted in FIG. 5B is shown cut along one of longitudinal struts 68 (along line 5B-5B) and flattened, although the anchor preferably is cut from a tubular material. Anchor 66 further includes a conduit formed by encapsulating the anchor with a biocompatible material, omitted for clarity from FIG. 5B, that covers the anchor between struts 67a and 67e.

Figure 6:
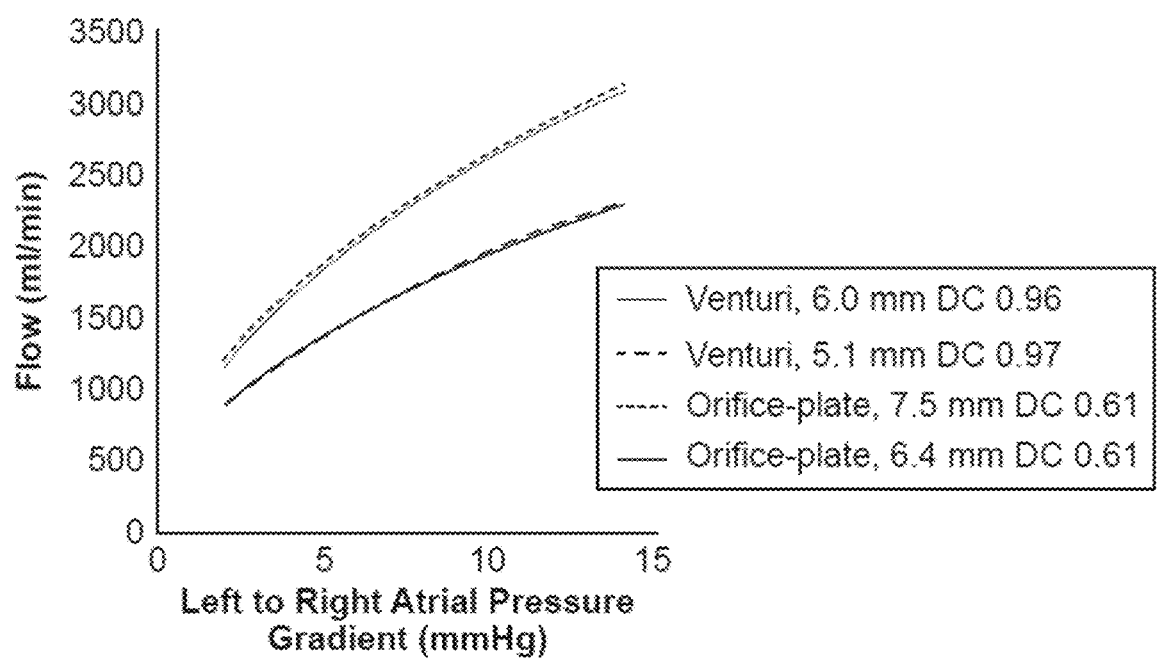
FIG. 6 is a graph comparing theoretical flows through a shunt design having a Venturi contour with 5 mm and 6 mm diameter orifices compared to theoretical flows obtained using orifice plate-type devices.

In accordance with one aspect of the present disclosure, an interatrial hourglass-shaped shunt with flow characteristics resembling a venturi tube and a discharge coefficient of approximately 0.96-0.97 may have a minimal neck orifice inner diameter ranging from 5 mm to approximately 6.5 mm. Having a somewhat larger orifice diameter, within this range, e.g. 6.0 mm, will support approximately 35% more flow for any given pressure gradient compared with a 5.1 mm shunt, as shown in FIG. 6. This may create improved hemodynamic conditions and may provide additional benefit in maintaining shunt flow should some shunt narrowing due to pannus ingrowth occur during device healing.

In accordance with another aspect of the disclosure, various nozzle geometries with high discharge coefficients relative to an orifice-plate geometry advantageously may be used to provide laminar flow through the shunt. These include but are not limited to various variations of venturi tubes, conical convergent nozzles (with convergence angles from 20 to 80 degrees), cylindrical convergent nozzles, and the Addy type nozzle with a convergent curved entrance wall leading to a length of cylindrical tubing having a diameter equivalent to the orifice diameter. The latter two appear similar in appearance to the horn of a trumpet. In another preferred embodiment, the shunt lumen may be a cylindrical tube with no or minimal dilation at the entry or exit ports.

The cross-section of lumen 22 (see FIG. 1B) need not be circular and/or the lumen need not be coaxial with a straight horizontal line axis when viewed longitudinally. Although these latter geometries may be difficult to deliver through catheters with circular luminal cross-sections, they may be constrained to such catheter lumens and expand into non-circular cross-sectional or curved longitudinal geometries upon deployment. Other preferred embodiments include any combination of entry, orifice, and exit geometries where the exiting jet vena contracta cross-sectional area is 70% or greater compared with the minimal orifice area, over the range of physiological interatrial pressure gradients, thereby having a higher discharge coefficient than an orifice-plate.

A shunt with a single LA conical entry funnel, with an hourglass-shaped lumen, or with a tubular lumen, having a discharge coefficient of 0.70 or larger, generally has a longer tunnel of entrained flow by nature of its longer length, typically 6 to 30 mm long, versus an orifice-plate mesh type shunt, which may be defined by the thickness of the FO itself and is typically shorter than 6 mm, e.g., 3 mm or less. For paradoxical embolization to occur, i.e., for a paradoxical embolus to embolize from the heart into the systemic arterial circulation, the paradoxical embolus must pass completely or nearly completely through the shunt. Emboli may be propagated by their momentum against a left-to right gradient or when there is no gradient, or may be carried along when a reversed pressure gradient creates right to left bulk flow. Depending on the relative magnitude of the kinetic energy of the embolus and the bulk flow directional status, a longer lumen shunt will tend to pass fewer emboli compared to an orifice-plate shunt with a shorter lumen. This is likely to be the case in the presence of normal left to right bulk flow or when there is zero net flow. This is also likely to be true during very transient pressure gradient reversals, such as during coughing, sneezing, squatting, defecation, or micturition. Therefore, in another preferred embodiment, a shunt with a flow lumen length of 6 to 30 mm, or more typically 10 to 15 mm, by virtue of its increased lumen length, will have less tendency for paradoxical embolization than an orifice-plate mesh shunt.

Figure 7A:
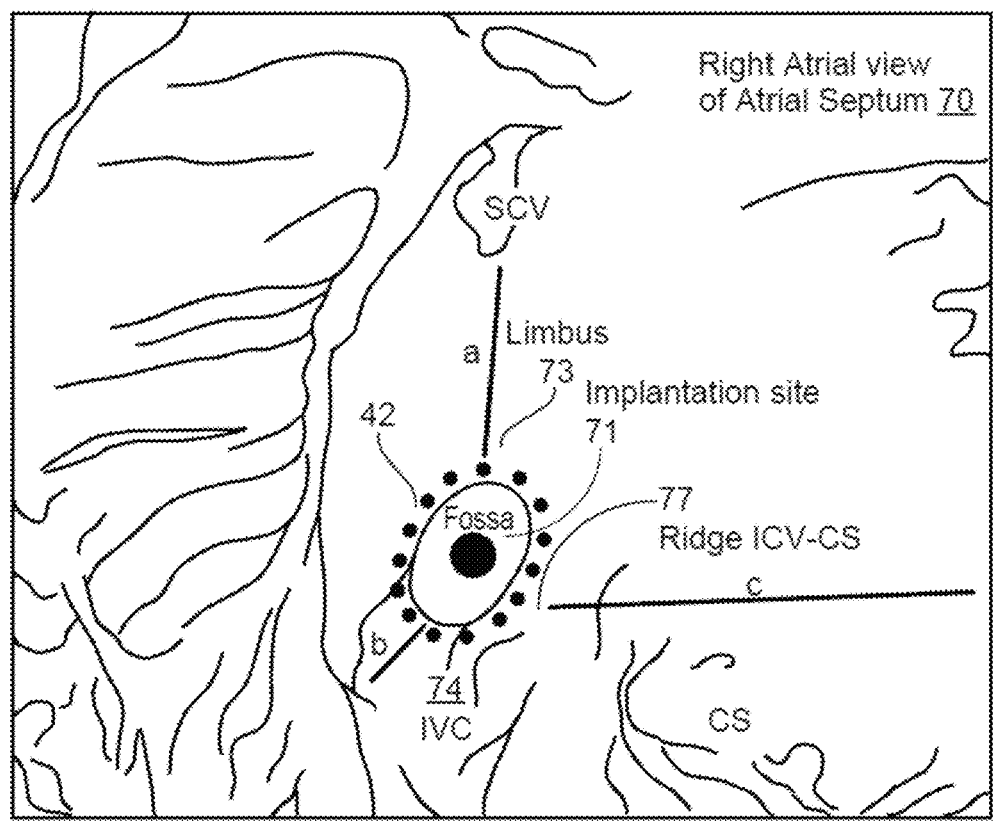
FIGS. 7A and 7B are, respectively, a plan view of the right atrial side of the atrial septum, illustrating implantation of a shunt through a portion of the fossa ovalis, and a perspective view of an embodiment of the shunt of FIGS. 1A-1C positioned in the fossa ovalis of the atrial septum.
Figure 7B:
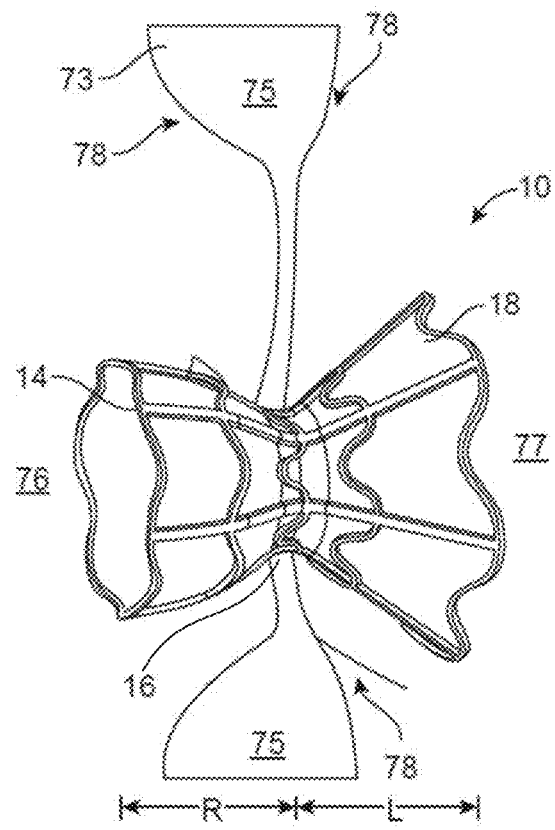

Referring now to FIG. 7A, a preferred location for implanting shunt 10 of FIGS. 1A-1C of the present disclosure is described. FIG. 7A is a plan view of the right atrial side of atrial septum 70, including implantation site 71 located at a central position of fossa ovalis 72. Preferably, implantation site 71 is selected so that the shunt may be implanted spaced apart from the surrounding limbus 73, inferior vena cava (IVC) 74, and atrial septum 75. For example, as shown in FIG. 7B, flared end region 14 is configured to be implanted in right atrium 76 and may be tapered so as to have a more cylindrical shape than does flared end region 18, which is configured to be implanted in left atrium 77. The more cylindrical shape of flared end region 14 may reduce or inhibit contact between flared end region 14 and limbus 73 of fossa ovalis 72, that is, between flared end region 14 and the prominent margin of the fossa ovalis, while still anchoring device 10 across atrial septum 75. The more cylindrical shape of flared end region 14 further may reduce or inhibit contact between flared end region 14, and the right side of atrial septum 70, as well as ridge 77 separating the coronary sinus from the IVC 74 (shown in FIG. 7A but not FIG. 7B).

Still with respect to FIG. 7A, a preferred location for shunt implantation may be slightly anterior to the centerline of the long axis of the fossa ovalis, i.e., located on the right hand side of the ovale. This location leaves potential space in the upper left quadrant (posterior-superior) of the fossa, which has been found to be optimal for crossing the fossa to perform structural heart disease procedures on the mitral valve, including edge-to-edge repair with MitraClip® transcatheter mitral valve repair system offered by Abbott, Abbott Park, IL and mitral annuloplasty with Cardioband, offered by Valtech Cardio, Or Yehuda, Israel. This preferred location also leaves potential space in the lower left quadrant (posterior-inferior) of the fossa, which has been found to be optimal for crossing the fossa to perform structural heart disease procedures to occlude the left atrial appendage. A shunt with an hourglass shape that occupies the smallest possible location on the fossa, as described herein, facilitates these other procedures.

Again, referring to FIG. 7B, shunt 10 preferably is configured so as to avoid imposing significant mechanical forces on atrial septum 75, thus allowing the septum to naturally deform as the heart beats. For example, the thicknesses of muscular areas of septum 75 may change by over 20% between systole and diastole. It is believed that any significant mechanical constraints on the motion of atrial septum 75 in such areas would lead to the development of relatively large forces acting on the septum and/or on atrial tissue that contacts shunt 10. Such forces could invoke an inflammatory response and/or hyperplasia in the atrial septum tissue, and possibly cause shunt 10 to eventually lose patency. However, by configuring shunt 10 so that neck region 16 may be implanted entirely or predominantly in the fibrous tissue of the fossa ovalis 72 with a small footprint, the hourglass shape of shunt 10 is expected to be sufficiently stable so as to be retained in the septum, while reducing mechanical loads on the surrounding atrial septum 75. Tissue ingrowth from atrial septum 75 in regions 78 may further enhance binding of shunt 10 to the septum. Preferably, there should be a substantial rim of fossa around the shunt after implantation, e.g., for a thickness of 1-2 mm, as depicted in FIG. 7B.

Also, because neck region 16 of shunt 10 is significantly narrower than flared end regions 14 and 18, shunt 10 will "self-locate" in a puncture through atrial septum 75, particularly when implanted through the fossa ovalis, with a tendency to assume an orientation where its longitudinal axis is substantially orthogonal to the FO. In some embodiments, neck region 16 may have a diameter suitable for implantation in the fossa ovalis, e.g., that is smaller than the fossa ovalis, and that also is selected to inhibit blood flow rates exceeding a predetermined threshold. Neck region 16 preferably provides a passage having a diameter between about 4 and about 7 mm, and more preferably between about 5 mm and about 6.5 mm. For example, diameters of less than about 4 mm may in some circumstances not allow sufficient blood flow through the shunt to decompress the left atrium, and may reduce long-term patency of the shunt. Conversely, diameters of greater than about 7 mm may allow too much blood flow, resulting in right ventricular volume overload and pulmonary hypertension. Preferably, the effective diameter at the narrowest point in shunt 10 is about 5 mm to 6.5 mm.

The diameters of flared end regions 14 and 18 further may be selected to stabilize shunt 10 in the puncture through atrial septum 45, e.g., in the puncture through fossa ovalis 72. For example, flared end region 18 may have a diameter of 10 to 20 mm at its widest point, e.g., about 13 to 15 mm; and flared end region 14 may have a diameter of 9 to 15 mm at its widest point, e.g., about 9 to 13 mm. The largest diameter of flared end region 14 may be selected so as to avoid mechanically loading the limbus of the fossa ovalis 72, which might otherwise cause inflammation. The largest diameter of flared end region 18 may be selected so as to provide a sufficient angle between flared end regions 14 and 18 to stabilize shunt 10 in the atrial septum, while limiting the extent to which flared end region 18 protrudes into the left atrium (e.g., inhibiting interference with flow from the pulmonary veins), and providing sufficient blood flow from the left atrium through neck region 16.

In accordance with the principles of the present disclosure, the length of end region 14 is selected to protrude into the right atrium by a distance sufficient to inhibit tissue ingrowth that may otherwise interfere with the operation of shunt 10. Applicants have observed that tissue ingrowth inwards along an impermeably membranes of specified biomaterials from the end that contacts tissue generally stops after about 3 mm. Accordingly, to ensure that tissue ingrowth from the ends of the conduit does not extend into and partially occlude the flow area of neck region 16, the distance R between the narrowest portion of neck region 16 and the end of region 14 should be at least 3 mm plus half of the thickness of the septal region, i.e., fossa ovalis, contacting the exterior of shunt 10. Assuming that the fossa ovalis has a thickness of about 3.0 mm, then the minimum distance R should be about 4.5 mm, based on applicants' observations. Likewise, end region 18 preferably does not significantly engage the left side of atrial septum 75, so that distance L also preferably is at least 4.5 mm. Due to patient-to-patient variability in the thickness of the FO, e.g., due to the patient's general health and age, and because neck region 16 may not be precisely aligned with the mid-point of the FO, each distances R and L preferably fall within a range of 3 to 6 mm. Accordingly, for some embodiments, the overall dimensions of shunt 10 may be about 9-12 mm long (L+R, in FIG. 7B) to prevent tissue ingrowth from the ends of the conduit, i.e., end regions 14 and 18, from partially occluding neck region 16.

In another preferred embodiment, regardless of the geometrical shape of the conduit, there should be a minimum of 3 mm of material resistant to translational tissue growth, i.e., extending inward from the ends of the end regions to accommodate neoendocardial tissue growth over the shunt surfaces starting from a location in contact with the atrial septum, such that tissue growth cannot reach the orifice (site of minimal diameter of the shunt lumen or cross-sectional area of lumen 22 shown in FIG. 1B). With this preferred embodiment, the minimal orifice diameter of an interatrial shunt device will be rendered largely unaffected by pannus formation. In another preferred embodiment, there should be a minimum of 3 mm of conduit length for neoendocardial tissue to grow over the shunt luminal surfaces starting from a location in contact with the atrial septum, before reaching the entrance or exit port sites of the shunt lumen. With such an embodiment, there is even less potential for pannus to encroach the shunt lumen.

Figure 8A:
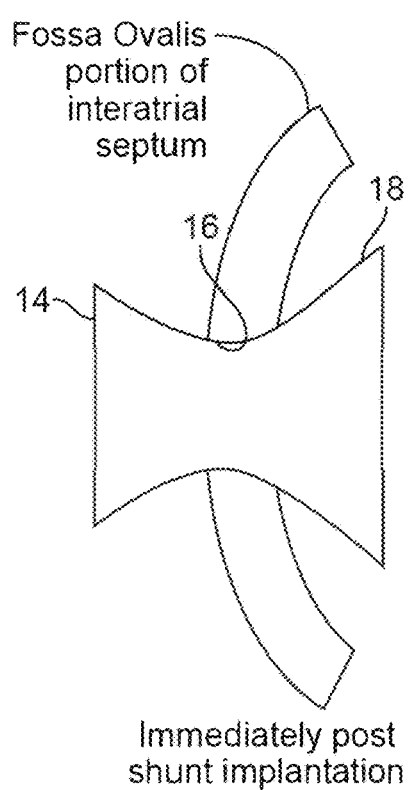
FIGS. 8A and 8B schematically depict pannus formation on an hourglass-shaped embodiment of the shunt of the present disclosure positioned in the fossa ovalis orthogonal to the atrial septum wall, immediately after implantation and after pannus formation.
Figure 8B:
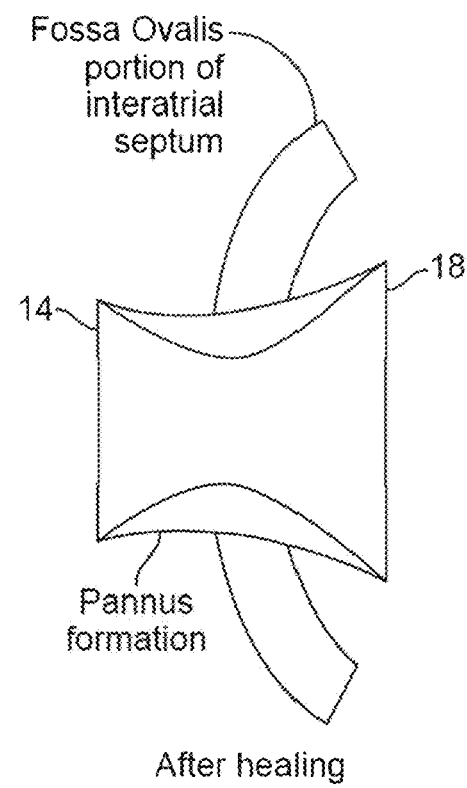
Figure 9A:
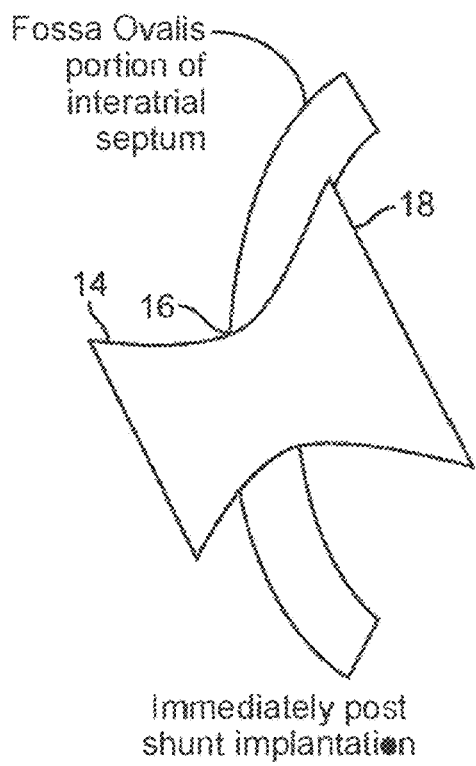
FIGS. 9A and 9B schematically depict pannus formation on an hourglass-shaped embodiment of the shunt of the present disclosure positioned in the fossa ovalis non-orthogonal to the atrial septum wall, immediately after implantation and after pannus formation.
Figure 9B:
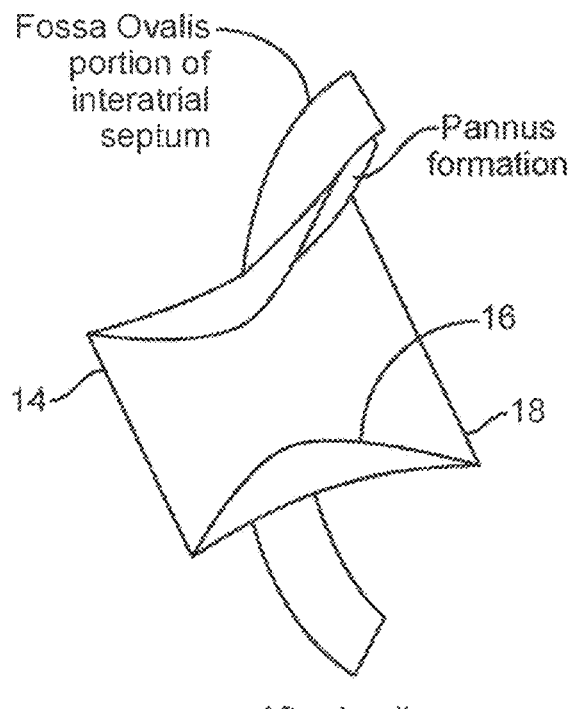

Referring now to FIGS. 8A and 8B, the expected healing response invoked by implanting shunt 10 of FIGS. 1A-1C orthogonally across the FO is described, while FIGS. 9A and 9B correspond to implantation of the shunt non-orthogonally so that an outer surface of the LA entry cone contacts the atrial septal tissue. FIGS. 8A and 9A depict positioning of the shunts immediately post implantation, while FIGS. 8B and 9B depict shunt positioning after the completion of the healing phase.

In each of FIGS. 8A and 8B, the FO is shown as bowed towards the RA and concave towards the LA. In patients with dilated cardiomyopathy or restrictive physiology, including most patients with left ventricular failure, regardless of etiology, the FO portion of the interatrial septum generally is bowed toward the right atrium. This gives the LA a generally concave or near hemispherical shape in the region centered on the FO. Conversely, the RA side of the FO is generally convex in shape. This orientation of the FO was confirmed by echocardiography (n=178 examinations) in the 38 patients implanted with the V-Wave Nitzan-type valved shunt discussed in the Background portion of this specification. In measurements of more than 100 patients exhibiting heart failure with preserved ejection fraction (HFpEF), the LA volume generally averaged 85 ml with a minimum volume of 54 ml, while for a like number of patients exhibiting heart failure with reduced ejection fraction (HFrEF), the LA volume generally averaged 104 ml with a minimum volume of 71 ml. Although the LA is often approximated by a sphere or an ellipsoid, there are frequently exceptions to this, for example, where the LA appears squashed when viewed in its anterior-posterior dimension. Although not specifically quantified, the RA appeared to be similar in size to the LA.

Although exceptions to RA bowing of septal anatomy occur, they generally do so in the presence of isolated right ventricular failure or severe pulmonary hypertension in the absence of left ventricular dysfunction or mitral valve disease, e.g. as occurs in pulmonary arterial hypertension (PAH). In those instances, RA pressure tends to exceed LA pressure causing the FO to bow in the opposite direction toward the LA. Such patients generally would derive no clinical benefit from left-to-right interatrial shunting. However, patients with severe pulmonary hypertension in the absence of left-sided heart failure may benefit from right-to-left shunting as a means to improve low systemic cardiac output. Several of the embodiments described in this disclosure would provide improved performance compared to right-to-left shunts currently available to that population of patients.

Another geometrical constraint is the frequent presence or need to place transvenous endocardial electrical pacing or defibrillation leads in or through the RA of heart failure patients. In the 38-patient feasibility study conducted with the V-Wave Nitzan-type shunt, 74% of patients had already been implanted with cardiac rhythm management devices prior to interatrial shunting. Most of these patients had 2 or 3 such electrical leads placed. Leads most often enter the RA from the superior vena cava (SVC). Right atrial pacing leads usually loop up and terminate anterio-laterally in the RA appendage, but in some circumstances, they are attached to a muscular portion of the interatrial septum. RV pacing and defibrillation leads usually course along the lateral wall of the RA, then cross the tricuspid valve, and terminate in the interventricular septum, RV apex, or pulmonary outflow tract. LV leads enter the coronary sinus, which is just below and anterior to the FO. Occasionally, leads must be placed from unusual sites of origin and may enter the RA from the inferior vena cava ("IVC"). Leads are usually left with enough slack so that they do not put tension on their terminal ends when the heart moves or changes position. Much of this slack results in a web of excess lead body material that is often concentrated in the RA.

The observations of septal bowing, the range of chamber dimensions observed and the consequences of multiple transvenous endocardial lead placement have important implications for interatrial shunt device design. If a shunt protrudes into the LA chamber, it preferably is placed so that it generally projects orthogonally with respect to the FO as shown in FIG. 8A. Orthogonal placement is expected to minimize impingement on other adjacent or nearby critical cardiac structures, such as the aortic root, the mitral valve annulus, the roof and the posterior wall of the LA, and the pulmonary veins. Alternatively, if not placed substantially orthogonally, as shown in FIG. 9A, the shunt geometry should be selected to prevent the shunt from interacting with these structures. Proper accounting for such design considerations will prevent erosion of the shunt into critical cardiac structures, and prevent blockage of flow through the shunt by luminal impingement by adjacent cardiac structures. Ideally, the shunt should also occupy minimal space within the LA and only minimally disturb its normal flow pattern. The LA fills from the pulmonary veins during ventricular systole and drains into the left ventricle when the mitral valve opens during diastole. Blood coming from the right superior pulmonary veins tends to course along and hug the interatrial septum preventing stasis near the FO.

In a preferred embodiment of shunt 10, the volume of blood displaced by the portion of the shunt protruding into the LA, i.e., the volume of blood in the portion of the shunt lumen protruding into the LA, should be less than or equal to 5% of the LA diastolic volume expected in the patient population. This is typically 2.0 ml or less in adult patients with heart failure. Moreover, the shunt should not protrude into the LA by more than 15 mm, or more typically 3 to 10 mm. These dimensional considerations may also be accomplished in conjunction with other shunt features that facilitate a substantially orthogonal orientation, such as an LA entry funnel.

Similar considerations exist for the RA side of the FO. The shunt should occupy a minimal volume and have only a small effect on normal flow patterns. In a preferred embodiment, the same occupying volume and protrusion distance considerations, apply to the RA side of the shunt, that is, the device and its lumen should occupy less than or equal to 5% of the RA diastolic volume, e.g., 2.0 ml or less in adult patients with heart failure, and protrude into the RA by no more than, for example, 15 mm, or more typically 3 to 10 mm. These dimensional considerations can also be accomplished in conjunction with other shunt features that facilitate a substantially orthogonal orientation, such as RA exit funnel. These same criteria apply when the shunt is used in an application where RA to LA shunting is desirable, e.g., pulmonary arterial hypertension (PAH). The shunt should protrude in the RA the least amount necessary so that it does not foul pacing leads or abrade their electrical insulation.

As described earlier, the propensity for venous thromboembolism ("VTE") to cross in the retrograde direction through a shunt is expected to be a function of not only the amount and duration of retrograde shunt flow from the RA to the LA, but also a result of the flow patterns in the RA. The path of flow in the adult RA is complex because blood enters the chamber from multiple sources which include the inferior vena cava (IVC), the superior vena cava (SVC), the coronary sinus and from the LA through the shunt. These flow paths include directional changes and asymmetries whose topology has been assessed by color flow Doppler imaging and more recently from magnetic resonance velocity mapping.

Since the overwhelming majority of VTE in adult patients originate from the lower extremities and pelvic veins, the path traveled by paradoxical emboli are most likely similar to the flow vectors for blood coming from the IVC. Flow from the inferior vena cava courses along the posterior wall of the RA chamber before looping around the roof, where it is directed toward the tricuspid valve by coursing along the interatrial septum. The rest of the cavity generally contains pooled blood. Thus, blood entering the RA from the IVC forms a clockwise vortex descending along the RA side of the interatrial septum in most patients with normal anatomy. Advantageously, this flow pattern of blood downwards from the roof of the RA and along the interatrial septum reduces the risk of blood pooling in the vicinity of neck region 16 of the inventive shunt 10, thus reducing the risk of local thrombus formation due to blood stasis. Further, these flow pathway observations suggest that a thrombus originating from inferior vena cava will a have a trajectory that passes very close to the RA orifice of a naturally occurring secundum type atrial septal defect or an orifice-plate mesh type shunt. As a result, any thrombus arriving from the inferior vena cava is essentially delivered to such a septal orifice by the flow path within the RA, so that even a small reversal of shunt flow could embolize the thrombus across the orifice into the LA.

In accordance with another aspect of the present disclosure, a preferred embodiment of an inventive shunt includes an exit port (end region 14) that extends a distance into the RA, e.g., 3 to 15 mm, or more typically 5 to 10 mm, sufficient to place the orifice of the exit port out of the naturally occurring flow paths in the RA. In particular, the exit port projects partially or completely through the stream of blood originating from the IVC that loops down across the interatrial septum. Such a shunt geometry thus will be expected to have a lower risk of paradoxical embolization compared with an orifice-plate mesh type shunt where the exit port is directed at the passing looped IVC flow stream.

Figure 10:
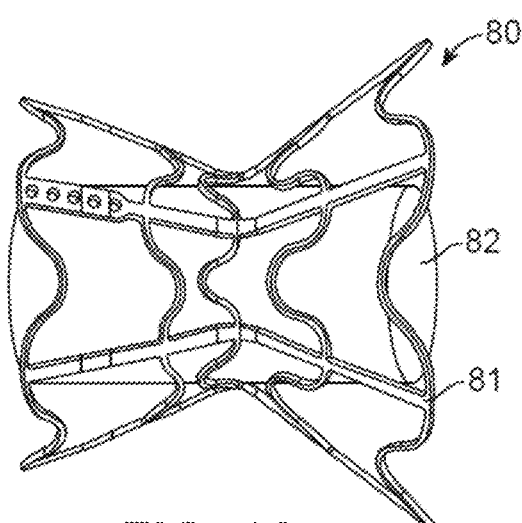
FIGS. 10 through 15 depict various alternative embodiments of shunts constructed in accordance with the principles of the present disclosure.
Figure 11:
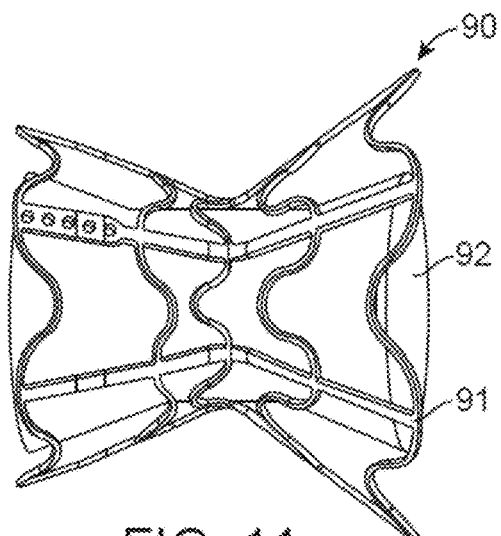

Referring now to FIGS. 10 and 11, additional alternative embodiments are described, where a conduit is registered with respect to the fossa ovalis of the interatrial septum by an external, unencapsulated bare metal anchor similar to anchor 12 of the embodiment of FIGS. 1A-1C. Specifically, shunt 80 of FIG. 10 includes anchor 81, which may be employed to register conduit 82 within the interatrial septum. Conduit 82 may include a separate encapsulated tubular frame or may comprise a tube of solid material, and may include a variety of geometries to achieve specific characteristics as previously described. Anchor 81 and conduit 82 may be physically affixed to each other prior to insertion in the body by mechanical interference, welding, adhesives, or other well-known means, and preferably includes a skirt that prevents bypass flow between anchor 81 and conduit 82. Alternatively, anchor 81 may be delivered across the septum deployed, and then conduit 82 may be inserted through and deployed within anchor 81 and held in place by mechanical interference or expansion with a balloon. The advantages of such a two-part design are two-fold. First, pannus will grow thick only on the outside surface of anchor 81 because the LA and RA ends of conduit 82 are offset from, and thus do not contact, adjacent cardiac structures. Second, the design creates a longest straight channel for high velocity flow, but limits the ability of paradoxical emboli to transit conduit 82 during a transient pressure gradient reversal. The dimensional aspects noted above with respect to the description of shunt 10 of FIG. 1C above may be applied to shunt 80.

FIG. 11 illustrates another preferred embodiment with benefits similar to that of the shunt of FIG. 10. More specifically, shunt 90 may include anchor 91 as described above with the respect to frame 12 of the embodiment of FIGS. 1A-1C. Conduit 92 may include flared end regions as described above, e.g., to form an hourglass shape in the deployed state. One of ordinary skill in the art will appreciate that the specific shape of the flared end regions may be conical, parabolic, or horned shaped, and may be present at either or both ends of the shunt device depending on the desired hydraulic properties. The dimensional aspects noted above with respect to the description of shunt 10 of FIG. 1C above may be applied to shunt 90.

The shunt types depicted in FIG. 10 and FIG. 11, or shunts with similar characteristics that would be apparent to one of ordinary skill in the art, may be particularly applicable to the clinical situation where too large an aperture defect has been created in the FO and where interatrial shunting to treat heart failure is required. Consider the case of a patient with severe mitral regurgitation and poor left ventricular function, where it would be clinically desirable to first perform a repair procedure on the mitral valve, e.g. MitraClip® of mitral annuloplasty by the percutaneous transseptal approach, followed by interatrial shunt placement. These mitral valve procedures currently use a 23Fr I.D. (~8 mm O.D) guiding catheter to cross the FO. After mitral repair, an anchor with an outer minimal diameter matching the larger aperture defect caused by the prior procedure may be implanted, wherein the conduit as a smaller diameter desirable for shunting (e.g. 5.0 to 6.5 mm). Likewise, such shunts advantageously may be used where, during the transseptal procedure, the fossa ovalis has been torn, thus creating a larger aperture defect than required for various shunt embodiments described with respect to FIGS. 1 to 5. Again, a shunt of the kind described with respect to FIG. 10 or 11 could be used to address such a situation.

Figure 12:
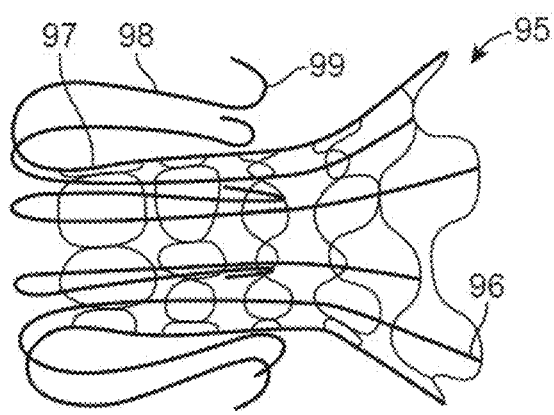

FIGS. 12-15 show further alternative shunt embodiments 95, 100, 110 and 120, respectively that use different shunt geometries in combination with anchors and anchoring tabs. The conduits of these shunts may be cylindrical, conical or have other lumen geometries as previously described herein. More specifically, in FIG. 12 anchor 95 suitable for use in an inventive shunt includes flared region 96 configured for deployment in the left atrium and substantially cylindrical region 97 that extends through the atrial septum and into the right atrium. Flexible struts 98 bend distally, i.e., towards the septum when the anchor is released from its delivery sheath, and preferably include U-shaped inverted ends that contact, but do not penetrate, the right atrial wall in the fully deployed position, as depicted in FIG. 12. Preferably, anchor 95, other than flexible struts 98 includes a conduit formed by encapsulating the anchor with polymeric material that prevents tissue ingrowth from obstructing the lumen of cylindrical region 97, and may be made of a biocompatible shape memory alloy, as described for preceding embodiments.

Figure 13:
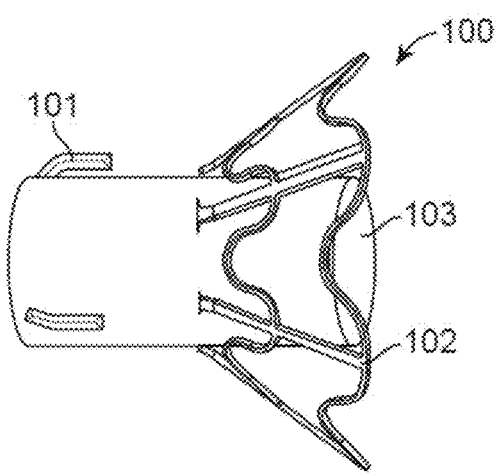

Shunt 100 of FIG. 13 may include a plurality of collapsible tab-like retention elements 101 disposed on the RA region of a cylindrical shunt. Retention elements 101 are designed to engage the FO to prevent migration/embolization of shunt 100 into the LA or beyond. With a much-thickened FO, retention elements 101 may become buried within the FO wall itself. In addition, shunt 100 may include conical anchor 102 extending at an angle into the LA from the LA side 103 of shunt 100, similar in construction to flared end region 18 of frame 12 of the embodiment of FIGS. 1A-1C. The advantage of this configuration is that it may be deployed in an FO that has any wall thickness (typically up to 10 mm). The other dimensional aspects noted above with respect to the description of shunt 10 of FIG. 1C above may be applied to shunt 100.

Figure 14:
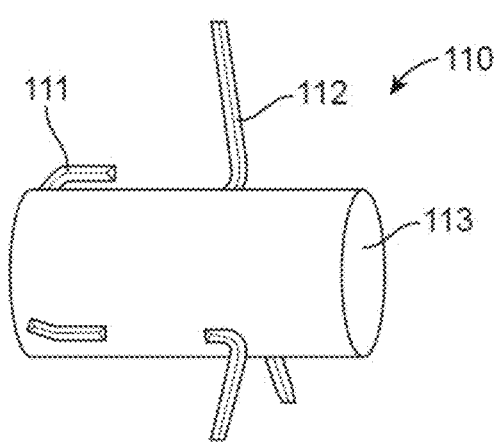

In FIG. 14, shunt 110 is similar in construction to shunt 100 and includes retention elements 111 on the RA side, but omits conical anchor 102 on the LA side. Instead, shunt 110 may include plurality of collapsible tabs 112 on LA side 113 of the shunt designed to offset cylindrical shunt 110 from the FO or other cardiac structures. An advantage of this configuration is that there is less structure occupying the free space in the LA. The other dimensional aspects of shunt 10 of FIG. 1C above may be applied to shunt 110.

Figure 15:
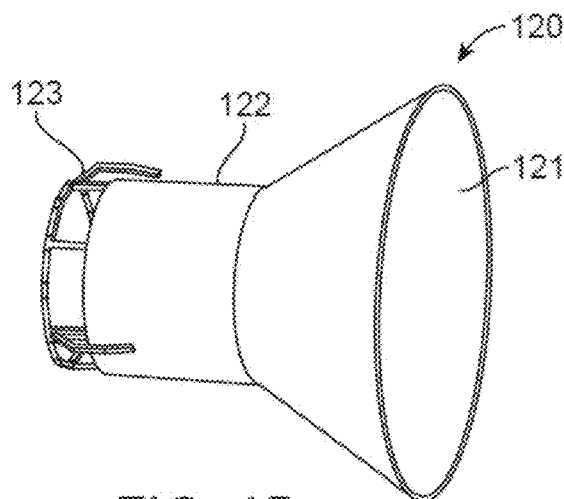

In FIG. 15, shunt 120 comprises an encapsulated expanded LA side 121, and a simple cylinder on RA side 122 that includes a plurality of retention elements 123. An advantage of this configuration is that shunt 120 may be constructed from a singular tubular frame. The other dimensional aspects of shunt 10 of FIG. 1C above may be applied to shunt 120.

Referring now to FIGS. 16A and 16B, anchor 130 of an alternative embodiment of a shunt constructed in accordance with the principles of the present disclosure is described. Anchor 100 is similar to anchor 12 of the embodiment of FIGS. 1A-1C, but further includes a plurality of flexible arms 131 attached to the circumferential strut nearest the exit port in the right atrium. Flexible arms 131 self-expand when the shunt is deployed to form a meshwork or filter that partially obstructs the exit port of the shunt. In particular, upon deployment, flexible arms 131 unfold to extend across the lumen in the vicinity of the lumen of the RA exit port, ideally near the location of its widest opening, to form a filter that prevents larger paradoxical emboli from passing into the left atrium. Flexible arms 131 permit blood to pass in either direction with minimal resistance while excluding the passage of paradoxical emboli that are generally larger than the mesh size, e.g., venous thromboemboli above a certain size, which may be on a paradoxical trajectory. In this case, the size of the emboli excluded is determined by the geometry of mesh. Prior to deployment, these arms may also serve as locations of attachment of the shunt to its delivery system. While in the embodiment depicted in FIGS. 16A and 16B, flexible arms 131 comprise struts that fold across the exit port of anchor 130 upon deployment, in alternative embodiments, flexible arms 130 may take any of a number of configurations, including a plurality or multiplicity of bars or arches that fold across the exit port to create a filter. In an alternative embodiment, as already described, larger paradoxical emboli could be excluded by having a plurality of passageways or lumina through the shunt device.

FIG. 17 is a graph depicting the effects of orifice size on the flow characteristics, e.g., bench testing quantified flow vs. pressure relationships, of two types of V-Wave Nitzan-type shunts as described in the above-incorporated application. Measurements were made in saline at 37 degrees Celsius, under constant pressure gradient conditions over the expected range of left-to-right pressure gradients. Flow was measured for the V-Wave 5.1 mm inner diameter orifice Nitzan-type hourglass-shaped valveless shunt and for a 6-mm inner diameter orifice valveless version of the shunt built upon the same nitinol frame. As depicted in FIG. 17, the 6-mm shunt has about 35% more flow than the 5 mm valved shunt. Also shown in FIG. 17, is the simulated flow for venturi tubes with orifice inner diameters of 5.1 and 6 mm with discharge coefficients of 0.97 and 0.96 respectively. These data suggest that the performance of the valveless hourglass shunts is closely approximated by a classical venturi. Simulations of a conical convergent nozzle (not shown) with a convergence angle of 37 and 36 degrees and a discharge coefficient of 0.92 for the 5.1 and 6 mm orifice inner diameters, respectively, showed similar predictive accuracy with actual shunts.

Referring again to FIG. 6, that figure depicts theoretical flows for a 5.1 mm and 6.0 mm venturi tube (discharge coefficient 0.97 and 0.96, respectively), as described above, along with flows through 6.4 mm and 7.5 mm orifice plates (discharge coefficient 0.61), respectively. As shown in FIG. 6, an orifice plate device requires an inner diameter of 7.5 mm to have flow characteristics similar to a 6 mm venturi tube. Similarly, an orifice plate device requires an inner diameter of about 6.4 mm to have flow characteristics similar to f a 5.1 mm venturi tube. These measured data and simulations show that the valveless lumen of the hourglass-shaped V-Wave Nitzan-type shunt is more efficient at supporting bulk flow over the expected physiological range of pressure gradients than an orifice-plate shunt.

In particular, an hourglass-shaped shunt permits a smaller orifice than an orifice-plate shunt with similar bulk flow capacity (7-8 mm in diameter). The smaller orifice, in turn, prevents proportionally larger thrombi from passing retrograde through the shunt and into the systemic circulation. Since ischemic damage from the lodging of embolus is limited to the watershed organ territory supplied by the occluded vessel, larger emboli tend to cause more damage and have more associated dangerous consequences, especially when the occluding vessel supplies the brain. Thus, with a smaller orifice size, paradoxical embolic strokes, if they occur, are likely to be smaller than with an orifice-plate mesh type shunt. Accordingly, in a preferred embodiment, a shunt having a discharge coefficient of 0.70 or greater will, by virtue of its smaller diameter or area orifice, have less tendency for paradoxical embolization than an orifice-plate mesh shunt with similar flow characteristics.

Clinical studies conducted using a orifice-plate mesh shunt offered by Corvia Medical, Inc., Tewksbury, MA, indicate that a 8-mm Corvia orifice-plate mesh shunt had a Qp/Qs=1.27±0.20 at 6 months compared to 1.06±0.32 just prior to implantation. This ratio was likely higher just after implantation due to some degree of shunt narrowing as a result of pannus formation that would be expected by 6 months. By comparison, for the V-Wave Nitzan-type valved shunt with a 5 mm orifice inner diameter, Qp/Qs derived from echo/Doppler analysis in the aforementioned patient cohort was relatively small at 1.18±0.16 shortly after implant compared to 1.04±0.22 at baseline (p<0.03). Qp/Qs decreased slightly to 1.12±0.14 by 6-12 months (p=0.10), consistent with the observed narrowing of the shunts over this same time period. These data suggest that the V-Wave Nitzan-type valved shunt, that was shown to have substantial early clinical benefit, was associated with a very small Qp/Qs ratio, and no evidence of worsening right heart failure or pulmonary hypertension. The data also suggest that a shunt of similar geometry can be made with a larger inner diameter, e.g., 6.5 mm inner diameter, without exceeding a Qp/Qs ratio of 1.5:1.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination.

The self-expanding shunts described herein may be implanted using a variety of delivery methods. Typically, the percutaneous placement of self-expanding devices across the atrial septum, or for that matter, across any cardiovascular structure that forms a barrier or wall with or without a pre-existing naturally occurring defect or orifice or a procedurally created defect dividing one hollow viscus from another, requires device-specific delivery systems that may cross the dividing barrier or orifice while keeping the device constrained and which may control the expansion of the device in the correct location in a secure way so as to minimize the risk of device misplacement or free embolization of the device.

For example, the desired barrier, e.g., the fossa ovalis of the atrial septum, may be percutaneously crossed using a transseptal needle/dilator system. The transseptal catheterization procedure may be performed from any suitable venous access site and may be guided by echocardiographic and/or fluoroscopic imaging. A guidewire may then be positioned to cross into the hollow viscus, e.g., the left atrium, distal to the barrier. The transseptal system may then be exchanged over the guidewire and replaced with the device-specific delivery system. For example, an outer introducer sheath having a conical shaped dilator protruding distally therefrom may be delivered across the atrial septum to enlarge the defect created by the transseptal crossing. In some embodiments, the dilator may be withdrawn. Alternatively, the dilator may be extended. Moreover, in some embodiments, the guidewire may be withdrawn, or alternatively, the guidewire may remain positioned across the atrial septum.

The self-expanding shunt may be constrained and advanced through the lumen of the introducer sheath, e.g., a cylindrical sleeve, with a reduced diameter so that it may easily be advanced across the atrial septum. For example, the shunt may be pre-constrained within the sheath at the time of manufacture or may be loaded into the sheath at the time of the delivery/deployment procedure. Further, the shunt may be mechanically coupled to a delivery catheter, e.g., a flexible tether having an inner mandrel on which the shunt is concentrically constrained. The mandrel/tether may be used either to advance the shunt or retract it, or both, depending on the deployment procedure or the need to recover a partially or fully expanded device. The mechanical coupling apparatus preferably is reversible to allow for decoupling of the mandrel/tether from the shunt at the desired time. For example, coupling mechanisms may include screw type threaded couplings, ball and releasable socket couplings, moveable hook/eyelet couplings, or any other suitable type of mechanical interference couplings that may be controlled remotely to maintain the shunt in a constrained configuration within the outer introducer sheath. The delivery catheter may be coupled at its proximal end to a control handle external to the patient that allows the operator to independently manipulate the sheath, mandrel/tether, and coupling mechanism in the desired sequence needed for delivery.

Figure 18A:
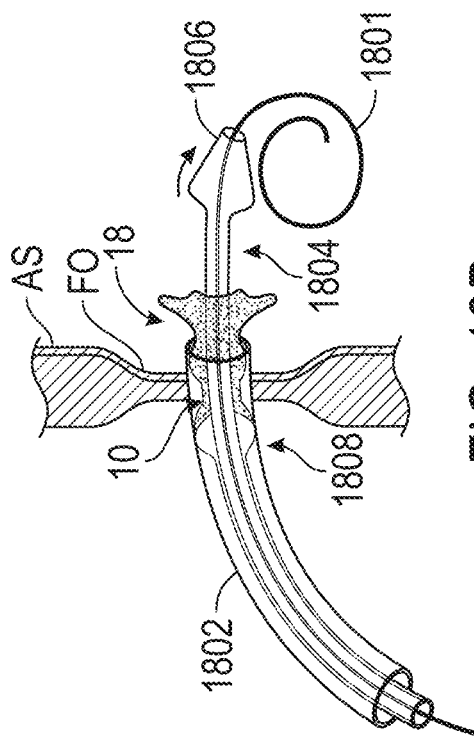
FIGS. 18A to 18D illustrate steps taken during an exemplary method of implanting an hourglass-shaped shunt of the present disclosure in accordance with the principles of the present disclosure.

Referring now to FIGS. 18A to 18D, an exemplary method for implanting an hourglass-shaped shunt, e.g., shunt 10, is provided. Prior to implanting shunt 10, a transseptal puncture may be created, e.g., via a transseptal needle, resulting in a procedurally created defect across atrial septum AS, e.g., at the location of fossa ovalis FO. As shown in FIG. 18A, guidewire 1801 may be placed across the orifice into the left atrium. Moreover, the delivery apparatus may include outer catheter sleeve/introducer sheath 1802, delivery catheter 1804, e.g., a mandrel/tether combination apparatus having distal conical dilator tip 1806 and coupling mechanism 1808, slidably moveable within the lumen of sheath 1802, and shunt 10 removably coupled to coupling mechanism 1808 of delivery catheter 1804 in a collapsed delivery state. For example, shunt 10 may be coupled to coupling mechanism 1808 by interference fit, such that delivery catheter 1804 may advance and/or retract shunt 10 within the lumen of sheath 1802.

As shown in FIG. 18A, the delivery apparatus may be advanced from the site of venous access over guidewire 1801 until the distal end of sheath 1802 is disposed within the left atrium. Delivery catheter 1804 may then be advanced into the left atrium (in the direction of the arrow) while sheath 1802 is maintained in position relative to atrial septum AS, to create sufficient space between the proximal end of conical dilator tip 1806 and the distal end of sheath 1802, as shown in FIG. 18A.

Figure 18B:
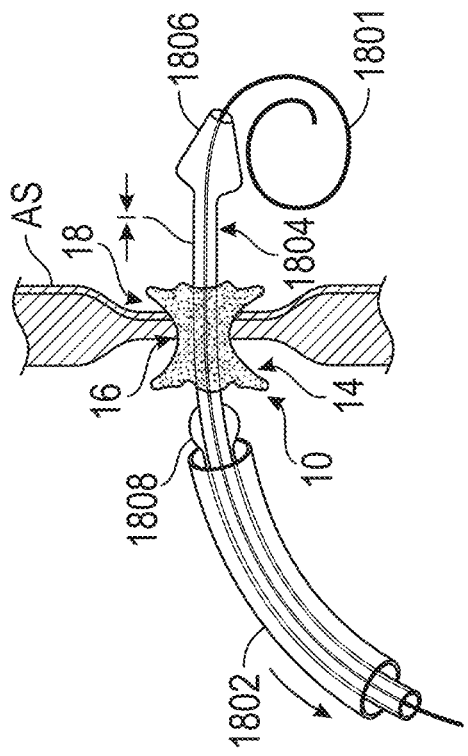

As shown in FIG. 18B, delivery catheter 1804 may be further advanced into the left atrium (in the direction of the arrow) while sheath 1802 is maintained in position relative to atrial septum AS, by a specific displacement amount relative to sheath 1802. As shown in FIG. 18B, this displacement amount advances shunt 10 within the lumen of sheath 1802 such that flared end region 18 of anchor 12 of shunt 10 is exposed beyond the distal end of sheath 1802 within the left atrium. Once no longer constrained by sheath 1802, flared end region 18 self-expands from the collapsed delivery state to an expanded deployed state within the left atrium. The specific displacement amount may be limited by a control mechanism in the region of the control handle (not shown). Alternatively, the operator may manually control the amount of displacement of the shunt, via coupling mechanism 1808 of delivery catheter 1804. Thus, shunt 10 may be retracted into the lumen of sheath 1802 via coupling mechanism 1808 of delivery catheter 1804 if delivery catheter 1804 is advanced too far relative to sheath 1802.

Figure 18C:
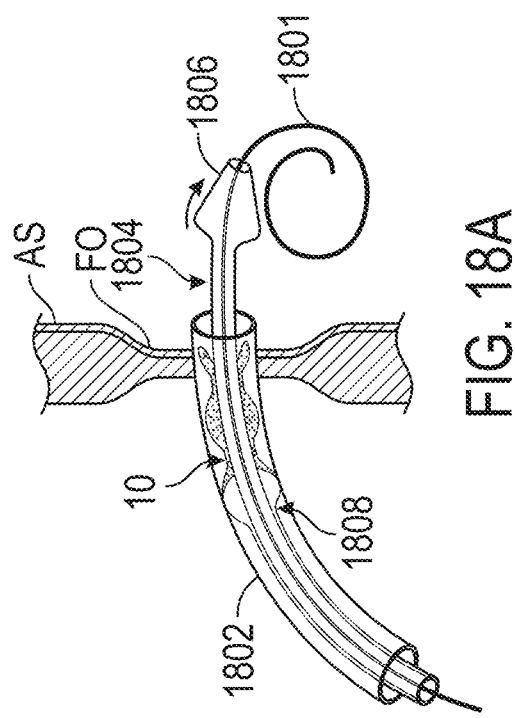

As shown in FIG. 18C, while guidewire 1801 is maintained stationary relative to atrial septum AS, sheath 1802 and delivery catheter 1804 coupled to shunt 10, may be withdrawn as a unit (in the direction of the arrow) proximally until flared end region 18 contacts the left atrial side of fossa ovalis FO.

Figure 18D:
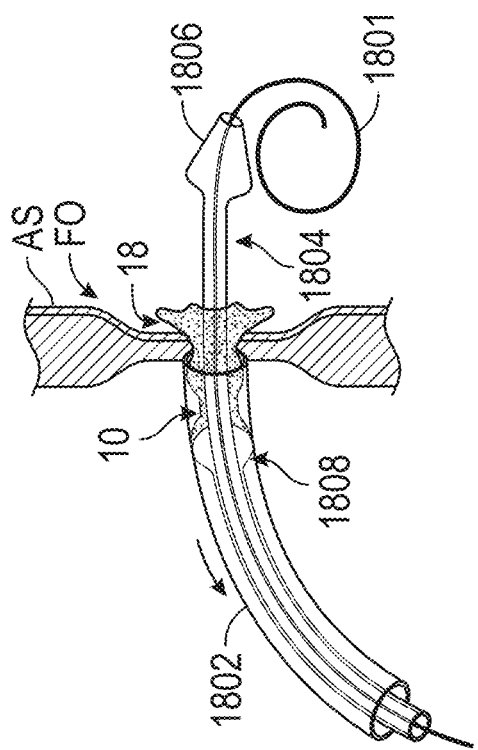

FIG. 18D illustrates the final stage of shunt deployment. While the operator maintains strict stationary positioning of guidewire 1801 and delivery catheter 1804 (indicated by the opposing arrows), sheath 1802 is retracted proximally (in the direction of the arrow) exposing flared end region 14 of anchor 12 of shunt 10. Once correct positioning of shunt 10 at atrial septum AS is confirmed via, e.g., echocardiographic or fluoroscopic imaging, coupling mechanism 1808 may be decoupled from flared end region 14, such that flared end region 14 self-expands from the collapsed delivery state to an expanded deployed state within the right atrium. Thus, neck region 16 of anchor 16 of shunt 10 will be lodged with the orifice of fossa ovalis FO. Conical dilator tip 1806 of delivery catheter 1804 and guidewire 1801 may then be withdrawn towards the right atrium through the passageway of shunt 10, and sheath 1802, delivery catheter 1804, and guidewire 1801 may be removed from the patient's body.

Figure 19:
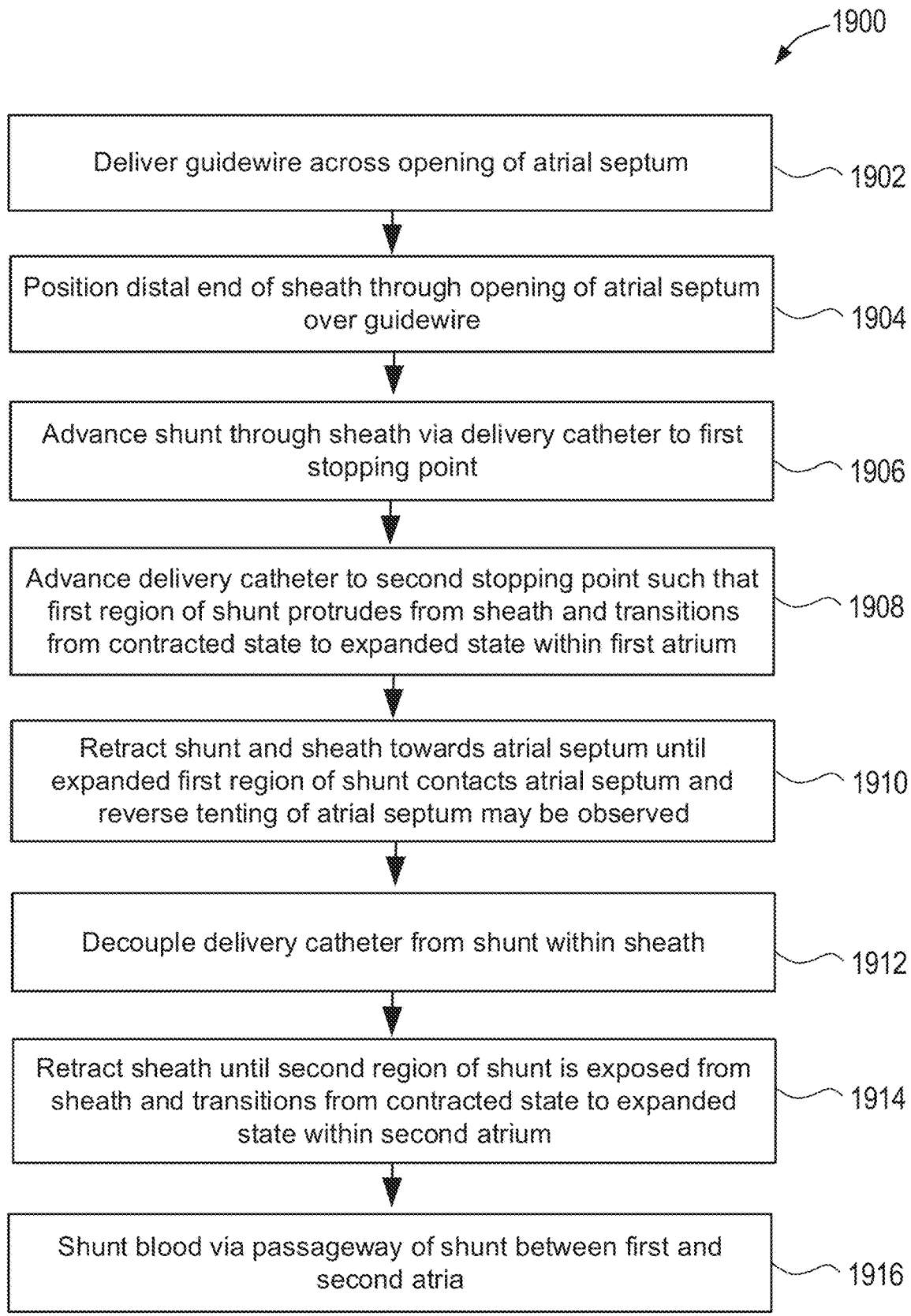
FIG. 19 is a flow chart of steps in an alternative exemplary method of implanting an hourglass-shaped shunt of the present disclosure in accordance with the principles of the present disclosure.

Referring now to FIG. 19, exemplary method 1900 for implanting an hourglass-shaped shunt, e.g., shunt 10, is provided. Some of the steps of method 1900 may be further elaborated by referring to FIGS. 20A to 20D. Prior to implanting shunt 10, a transseptal puncture may be created, e.g., via a transseptal needle, resulting in a procedurally created defect across atrial septum AS, e.g., at the location of fossa ovalis FO. At step 1902, guidewire 2001 may be placed across the orifice into the left atrium. The delivery apparatus may include outer catheter sleeve/introducer sheath 2002, delivery catheter 2004, e.g., a mandrel/tether combination apparatus having coupling mechanism 2006, slidably moveable within the lumen of sheath 2002, and shunt 10 removably coupled to coupling mechanism 2006 of delivery catheter 2004 in a collapsed delivery state. For example, shunt 10 may be coupled to coupling mechanism 2006 by interference fit, such that delivery catheter 2004 may advance and/or retract shunt 10 within the lumen of sheath 2002. Additionally or alternatively, coupling mechanism 2006 may include a plurality of retractable hooks for releasably engaging with shunt 10, as described in, for example, U.S. Pat. No. 9,713,696 to Yacoby and/or U.S. Patent Publication No. 2020/0315599 to Nae, the entire contents of each of which are incorporated herein by reference.

At step 1904, sheath 2002 may be advanced over guidewire 2001 across the orifice into the left atrium such that the distal end of sheath 2002 is disposed within the left atrium. Sheath 2002 may be advanced across the orifice of fossa ovalis FO with a removable conical tip dilator (not shown) to dilate the orifice, and the dilator tip may be removed through the lumen of sheath 2002. A loading apparatus may be used to constrain the diameter of shunt 10 within sheath 2002. At step 1906, delivery catheter 2004 coupled to shunt 10 may be advanced through the lumen of sheath 2002, e.g., over guidewire 2001. For example, delivery catheter 2004 may be advanced to first stopping point A within the lumen of sheath 2002, as shown in FIG. 20A. At first stopping point A, the distal end of shunt 10 may be within 1 to 5 cm proximal to the distal end of sheath 2002. Correct positioning of delivery catheter 2004 at first stopping point A may be determined by the operator based on, e.g., fluoroscopic or echocardiographic visualization of shunt 10 relative to the distal end of sheath 10. Alternatively, correct positioning of delivery catheter 2004 at first stopping point A may be determined by fiducial markings on delivery catheter 2004, or by some portion of delivery catheter 2004 reaching a mechanical stopper. As shown in FIG. 20A, at first stopping point A, shunt 10 is fully constrained within sheath 2002 such that the distal end of shunt 10 is positioned within 1 to 5 cm, or preferably 1 to 3 cm, from the distal end of sheath 2002.

After positioning delivery catheter 2004 at first stopping point A, the operator may confirm that the distal end of sheath 2002 is positioned a predetermined distance, e.g., 1 to 3 cm, beyond the barrier, e.g., fossa ovalis FO within the left atrium, such that the distal end of sheath 2002 is not in proximity to more distal cardiac structures, e.g., the pulmonary veins, the left atrial appendage, the mitral valve or the left ventricular cavity. Moreover, the operator may further confirm that the distal end of sheath 2002 has not been inadvertently withdrawn back across fossa ovalis FO into the right atrium, or more proximally. For example, this may be determined by injecting agitated saline through a proximal port of delivery catheter 2004 or of sheath 2002, and observing the location of microbubbles exiting the distal end of sheath 2002, e.g., via 2-dimensional ultrasonic imaging, or alternatively, by injecting radiographic contrast material through a proximal port of delivery catheter 2004 or of sheath 2002, and observing the location of radiographic contrast material exiting the distal end of sheath 2002, e.g., by fluoroscopy.

At step 1908, delivery catheter 2004 may be advanced to second stopping point B within the lumen of sheath 2002, as shown in FIG. 20B. At second stopping point B, flared end region 18 of anchor 12 of shunt 10 protrudes beyond the distal end of sheath 2002. Once no longer constrained by sheath 2002, flared end region 18 self-expands from the collapsed delivery state to an expanded deployed state within the left atrium. The specific displacement amount may be limited by a control mechanism in the region of the control handle (not shown). Alternatively, the operator may manually control the amount of displacement of the shunt, via coupling mechanism 2006 of delivery catheter 2004. Accordingly, shunt 10 may be retracted into the lumen of sheath 2002 via coupling mechanism 2006 of delivery catheter 2004 if delivery catheter 2004 is advanced too far relative to sheath 2002.

At step 1910, while guidewire 2001 is maintained stationary relative to atrial septum AS, sheath 2002 and delivery catheter 2004 coupled to shunt 10, are withdrawn as a unit proximally, e.g., to third stopping point C, until flared end region 18 contacts the left atrial side of fossa ovalis FO, as shown in FIG. 20C. Tension applied to the left atrial side of fossa ovalis FO by flared end region 18 of shunt 10 may be observed, e.g., by ultrasonic imaging, as bowing of fossa ovalis FO toward the right atrium, also known as "reverse tenting." At step 1912, coupling mechanism 2006 of delivery catheter 2004 may be decoupled from shunt 10. Optionally, decoupling from the shunt, the operator may retract delivery catheter 2004 proximally a predetermined distance (in the direction of the arrow) while sheath 2002 remains stationary relative to atrial septum AS to confirm that the decoupling between coupling mechanism 2006 and shunt 10 is successful.

FIG. 20D illustrates the final stage of shunt deployment. At step 1914, while the operator maintains positioning of guidewire 2001 within the left atrium, sheath 2002 may be retracted (in the direction of the arrow) until the counterforce exerted by shunt tension on fossa ovalis OA and septal tissues overcomes the friction of neck region 16 and flared end region 14 of shunt 10 retained within sheath 10, effectively pulling the retained portions of shunt 10 out of sheath 2002. Advantageously, only guidewire 2001 needs to be maintained in position (indicated by the opposing arrows), while sheath 2002 and delivery catheter 2004 may be moved relative to atrial septum AS. Thus, the operator need not maintain the position of shunt 10 via delivery catheter 2004 during shunt deployment.

The force (F1) required to unsheathe neck region 16 and flared end region 14 of the shunt 10 must be less than the force (F2) required to retract and re-constrain flared end region 18 of shunt 10 within sheath 2002, e.g., cause flared end region 18 to transition from the expanded state to the contracted state. For example, F1 may range from 0.8 to 8.3 Newtons, and F2 may range from 12 to 16 Newtons. This allows flared end region 18 to remain in its expanded deployed state such that shunt 10 is anchored on the left side of fossa ovalis FO and flared end region 18 does not get pulled through the orifice of fossa ovalis FO into the right atrium. In addition, the yield stress of fossa ovalis FO and atrial septum AS must also exceed F1. Accordingly, the septal anatomy in close proximity to the orifice of fossa ovalis FO accurately registers the optimal positioning of flared end region 18 at all times during the deployment of flared end region 14 of shunt 10, thereby assuring safe and accurate shunt deployment.

Thus, at step 1914, flared end region 14 of shunt 10 will be exposed from the distal end of sheath 2002, such that flared end region 14 self-expands from the collapsed delivery state to an expanded deployed state within the right atrium. Accordingly, neck region 16 of shunt 10 will be lodged within the orifice of fossa ovalis FO. This "drag-and-drop" delivery procedure provides reliable, repeatable shunt deployment. Upon confirmation of correct positioning of shunt 10 across fossa ovalis FO, e.g., via imaging, guidewire 2001 may then be withdrawn towards the right atrium through the passageway of shunt 10, and sheath 2002, delivery catheter 2004, and guidewire 2001 may be removed from the patient's body. At step 1916, blood may be shunted via the passageway of shunt 10 between the left and right atria, e.g., responsive to a pressure differential across atrial septum AS.

It is to be appreciated that certain features of the invention, which are, for clarity, described in the context of separate embodiments, also may be provided in combination in a single embodiment. Conversely, various features of the invention, which for brevity are described in the context of a single embodiment, also may be provided separately or in any suitable subcombination. While various illustrative embodiments of the invention are described above, it will be apparent to one with ordinary skill in the art that various changes and modifications may be made herein without departing from the invention. Therefore, the full scope of the invention must be ascertained by reference to the appended claims, along with the full scope of equivalents to which those claims are legally entitled.

While various illustrative embodiments of the disclosure are described above, it will be apparent to one skilled in the art that various changes and modifications may be made herein without departing from the disclosure.

What is claimed is:

1. An interatrial shunt for regulating blood volume distribution configured for placement in an interatrial septum between a patient's left atrium and the patient's right atrium, the interatrial shunt comprising:
    an hourglass-shaped anchor having a first region, a second region, a neck region joining the first region to the second region, the hourglass-shaped anchor configured to transition from a collapsed delivery state to an expanded deployed state in which the first region extends into the patient's left atrium, the second region extends into the patient's right atrium, and the neck region is disposed at the interatrial septum, the expanded deployed state exhibiting the hourglass-shape; and
    an expanded-polytetrafluoroethylene (ePTFE) conduit affixed to the hourglass-shaped anchor and defining a lumen that permits blood to flow across the interatrial septum via the interatrial shunt, wherein the lumen at a narrow portion of the neck region has a diameter of 4-6 mm in the expanded deployed state, and wherein the first region is configured to protrude 2.5-7 mm into the left atrium and the second region is configured to protrude 5-9 mm into the right atrium in the expanded deployed state.

2. The interatrial shunt of claim 1, wherein the lumen of the interatrial shunt is sized and shaped to permit an amount of blood to flow across the interatrial septum to treat the patient's heart failure.

3. The interatrial shunt of claim 1, wherein the lumen of the interatrial shunt is sized and shaped to permit an amount of blood to flow across the interatrial septum to treat the patient's pulmonary hypertension.

4. The interatrial shunt of claim 1, wherein the lumen of the interatrial shunt is sized and shaped to permit an amount of blood to flow across the interatrial septum while preventing right ventricle (RV) overload.

5. The interatrial shunt of claim 1, wherein the lumen of the interatrial shunt is sized and shaped to permit an amount of blood to flow across the interatrial septum to lower blood pressure in the left atrium.

6. The interatrial shunt of claim 1, wherein the hourglass-shaped anchor is configured to self-expand to the expanded deployed state.

7. The interatrial shunt of claim 1, wherein the hourglass-shaped anchor is formed of superelastic material.

8. The interatrial shunt of claim 1, wherein the hourglass-shaped anchor is formed of nitinol.

9. The interatrial shunt of claim 1, wherein the hourglass-shaped anchor is laser cut from a single tube of nitinol.

10. The interatrial shunt of claim 1, wherein the hourglass-shaped anchor is a diabolo-shaped body.

11. The interatrial shunt of claim 1, wherein the interatrial shunt is configured for percutaneous delivery to the interatrial septum through a sheath while in the collapsed delivery state.

12. The interatrial shunt of claim 11, wherein the interatrial shunt is configured to be pushed through, and out of, the sheath via a delivery catheter.

13. The interatrial shunt of claim 1, wherein the diameter is 4-5.5 mm.

14. The interatrial shunt of claim 1, wherein the interatrial shunt has a length of 10-20 mm.

15. The interatrial shunt of claim 1, wherein the interatrial shunt has a length of 10-18 mm in the collapsed delivery state.

16. The interatrial shunt of claim 1, wherein the first and second regions have a maximal diameter of 10-16 mm in the expanded deployed state.

17. The interatrial shunt of claim 1, further comprising a valve for controlling flow through the interatrial shunt.

18. The interatrial shunt of claim 1, wherein the interatrial shunt remains patent post-implantation.

19. The interatrial shunt of claim 1, wherein the ePTFE conduit defines a lumen wall that is resistant to transmural and translational tissue growth.

20. The interatrial shunt of claim 1, wherein the ePTFE conduit has a first end that is configured to extend from the neck region a first distance of at least 3 mm into the patient's left atrium and a second end that is configured to extend from the neck region a second distance of at least 3 mm into the patient's right atrium, thereby preventing pannus formation from narrowing the lumen in the neck region.

21. The interatrial shunt of claim 20, wherein the ePTFE conduit is configured so that when implanted the second end of the ePTFE conduit is located out of a natural circulation flow path of blood entering into the patient's right atrium from an inferior vena cava, thereby reducing a risk of emboli entrained in flow from the inferior vena cava being directed into the second end of the ePTFE conduit.

22. The interatrial shunt of claim 1, wherein the hourglass-shaped anchor comprises a plurality of circumferential sinusoidal struts interconnecting longitudinal struts.

23. The interatrial shunt of claim 1, wherein the ePTFE conduit encapsulates the hourglass-shaped anchor except for a portion defining cutouts adjacent to an end of the ePTFE conduit.

24. The interatrial shunt of claim 1, wherein the ePTFE conduit has an exterior surface that is impermeable to transmural tissue growth and resistant to translational tissue growth.

25. The interatrial shunt of claim 1, wherein the hourglass-shaped anchor, in the expanded deployed state, forms a filter that prevents emboli from entering an end of the ePTFE conduit.

26. A method for regulating blood volume distribution between a patient's left atrium and the patient's right atrium, the method comprising:
   implanting an interatrial shunt to treat a heart condition, the interatrial shunt comprising:
      an hourglass-shaped anchor having a first region, a second region, a neck region joining the first region to the second region, the hourglass-shaped anchor configured to transition from a collapsed delivery state to an expanded deployed state in which the first region extends into the patient's left atrium, the second region extends into the patient's right atrium, and the neck region is disposed at the interatrial septum, the expanded deployed state exhibiting the hourglass-shape; and
      an expanded-polytetrafluoroethylene (ePTFE) conduit affixed to the hourglass-shaped anchor and defining a lumen that permits blood to flow across the interatrial septum via the interatrial shunt, wherein the lumen at a narrow portion of the neck region has a diameter of 4-6 mm in the expanded deployed state, and wherein the first region is configured to protrude 2.5-7 mm into the left atrium and the second region is configured to protrude 5-9 mm into the right atrium in the expanded deployed state.

* * * * *